(12) United States Patent
Brown et al.

(10) Patent No.: US 7,528,170 B2
(45) Date of Patent: *May 5, 2009

(54) SULFONAMIDE DERIVATIVES FOR THE TREATMENT OF DISEASES

(75) Inventors: Alan Daniel Brown, Sandwich (GB); Mark Edward Bunnage, Sandwich (GB); Paul Alan Glossop, Sandwich (GB); Kim James, Sandwich (GB); Charlotte Alice Louise Lane, Sandwich (GB); Russel Andrew Lewthwaite, Sandwich (GB); Ian Brian Moses, Sandwich (GB); David Anthony Price, Sandwich (GB); Nicholas Murray Thomson, Sandwich (GB)

(73) Assignee: Pfizer Inc., New York, NY (US)

( * ) Notice: Subject to any disclaimer, the term of this patent is extended or adjusted under 35 U.S.C. 154(b) by 19 days.

This patent is subject to a terminal disclaimer.

(21) Appl. No.: 11/772,995

(22) Filed: Jul. 3, 2007

(65) Prior Publication Data

US 2008/0267970 A1 Oct. 30, 2008

Related U.S. Application Data

(63) Continuation of application No. 11/038,452, filed on Jan. 19, 2005, now Pat. No. 7,244,766.

(60) Provisional application No. 60/600,260, filed on Aug. 9, 2004.

(30) Foreign Application Priority Data

| Jan. 22, 2004 | (EP) | .................................. 04290169 |
| Mar. 22, 2004 | (GB) | .................................. 0406387.1 |
| Jan. 12, 2005 | (EP) | .................................. 05702252 |
| Jan. 12, 2005 | (WO) | ....................... PCT/IB05/00086 |

(51) Int. Cl.
*A61K 31/18* (2006.01)
*A61K 31/472* (2006.01)

(52) U.S. Cl. ...................... 514/605; 514/307; 514/330; 514/357

(58) Field of Classification Search ................. 514/605, 514/307, 330, 357
See application file for complete search history.

(56) References Cited

U.S. PATENT DOCUMENTS

| 4,540,581 | A | 9/1985 | Nair et al. ................... 514/415 |
| 5,776,983 | A | 7/1998 | Washburn et al. ........... 514/605 |
| 7,244,766 | B2 * | 7/2007 | Brown et al. ................. 514/605 |
| 2002/0143034 | A1 | 10/2002 | Taniguchi et al. ........... 514/332 |
| 2003/0165700 | A1 | 9/2003 | Kosuge et al. .............. 428/483 |
| 2003/0229058 | A1 | 12/2003 | Moran et al. ................. 514/171 |
| 2004/0039204 | A1 | 2/2004 | Dumic et al ................... 546/1 |
| 2004/0180947 | A1 | 9/2004 | Kayakiri et al. ............. 514/444 |

FOREIGN PATENT DOCUMENTS

| EP | 0080595 | 5/1985 |
| EP | 0569737 | 11/1993 |
| JP | 10218861 | 8/1998 |
| WO | WO 9111172 | 8/1991 |
| WO | WO 9402518 | 2/1994 |
| WO | WO 9855148 | 12/1998 |
| WO | WO 9964035 | 12/1999 |
| WO | WO 0200622 | 1/2002 |
| WO | WO 0206258 | 1/2002 |
| WO | WO 03099764 | 12/2003 |
| WO | WO 2004100950 | 11/2004 |

OTHER PUBLICATIONS

* US 2004/0039204 is an English Equivalent to WO 02/328186.
** US 2004/0180947 is an English Equivalent to WO 99/00372.
Barnes, P. J. Chest, 111:2, pp. 17S-26S, 1997.
Bryan et al., Expert Opinion on Investigational Drugs, 9:1, pp. 25-42, 2000.
Haleblian, J. Pharm Sci, 64:8, pp. 1269-1288, 1975.
Finnin and Morgan, J. Pharm Sci, 88:10, pp. 955-958, 1999.

* cited by examiner

*Primary Examiner*—Charanjit S Aulakh
(74) *Attorney, Agent, or Firm*—Gregg C. Benson; Robert T. Ronau

(57) ABSTRACT

The invention relates to compounds of formula (1)

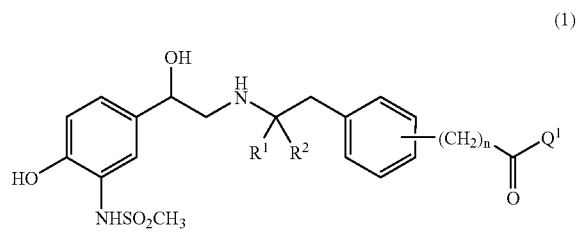

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

2 Claims, No Drawings

SULFONAMIDE DERIVATIVES FOR THE TREATMENT OF DISEASES

This invention relates to β2 agonists of general formula:

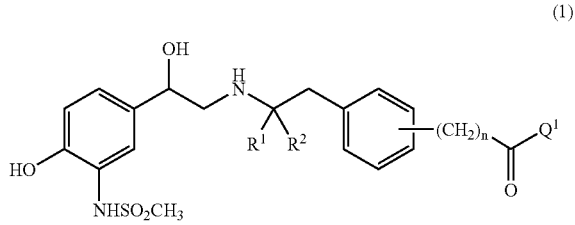

in which $R^1$, $R^2$, n and $Q^1$ have the meanings indicated below, and to processes for the preparation of, compositions containing and the uses of such derivatives.

Adrenoceptors are members of the large G-protein coupled receptor super-family. The adrenoceptor subfamily is itself divided into the α and β subfamilies with the p sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S-26S and Bryan, S. A. et al, Expert Opinion on investigational drugs, 2000, 9:1, pp 2542) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency, pharmacokinetics or duration of action. In this context, the present invention relates to novel β2 agonists.

Various Sulfonamide derivatives have already been disclosed. For example, WO02066250 discloses compounds active as $β_3$ agonist, selective over β2, of formula

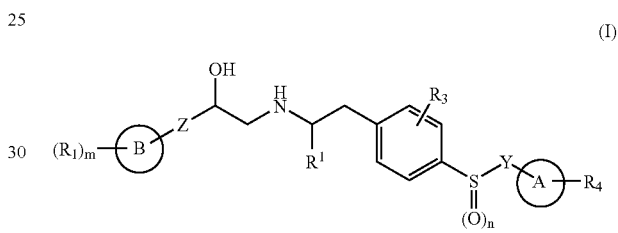

wherein m may be 2, $R_1$ may be H, OH or $NR_5SO_2R_5$ ($R_5$ being H or $C_1$-$C_6$ alkyl), Z may be a bond, $R_2$ may be H or $C_1$-$C_6$ alkyl, $R_4$ may be $C_1$-$C_6$ alkyl, B may be phenyl, Y is $C_1$-$C_6$ alkyl and A may be phenyl.

WO02/000622 discloses selective β3 agonists of formula:

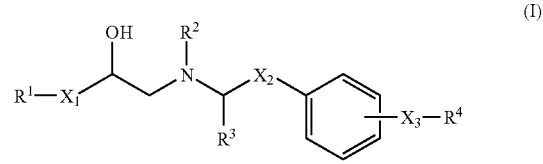

wherein $R^1$ may be phenyl substituted with hydroxy and alkylsulfonylamino, $X_1$ may be a bond, $R^2$ may be hydrogen, $R^3$ is hydrogen or hydroxyalkyl, $X_2$ may be $CH_2$, $X_3$ is a bond, O or NH and $R^4$ is cyclic group.

Other sulfonamide derivatives are also disclosed in U.S. Pat. No. 5,776,983 as β3 agonists They are more specifically of formula:

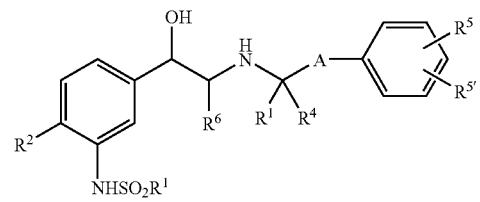

wherein $R^1$ may be $CH_3$, $R^2$ may be OH, $R^6$ may be H, $R^3$ may be H or alkyl, $R^4$ may be H, alkyl, $R^5$ may be H, $R^{5'}$ may be $C(O)NR^6R^{6'}$ wherein $R^6$ and $R^{6'}$ may be H or lower alkyl.

However, none of the above sulfonamide derivatives have shown a β2 agonist activity and a pharmacological profile allowing them to be used as efficient drugs in the treatment of the β2-mediated diseases and/or conditions, in particular allergic and non-allergic airways diseases or other diseases such as those previously cited.

The invention relates to the compounds of general formula (1):

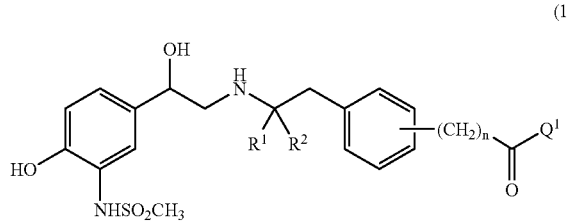
(1)

wherein the $(CH_2)_n$—$C(=O)Q^1$ group is in the meta or para position, $R^1$ and $R^2$ are independently selected from H and $C_1$-$C_4$ alkyl, n is 0, 1 or 2 and $Q^1$ is a group selected from:

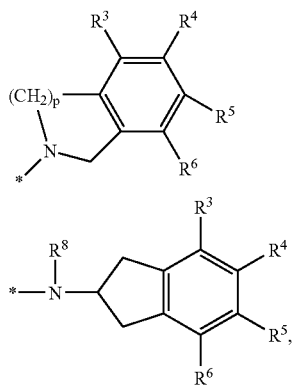

and a group *—$NR^8$-$Q^2$-A, wherein p is 1 or 2, $Q^2$ is a $C_1$-$C_4$ alkylene optionally substituted with OH, $R^8$ is H or $C_1$-$C_4$ alkyl and A is pyridyl optionally substituted with OH, $C_3$-$C_7$ cycloalkyl optionally substituted with OH or a group

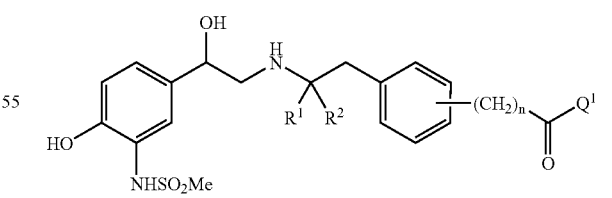

wherein $R^3$, $R^4$, $R^5$, $R^6$ and $R^7$ are the same or different and are selected from H, $C_1$-$C_4$ alkyl, $OR^9$, $SR^9$, halo, CN, $CF_3$, $OCF_3$, $COOR^9$, $SO_2NR^9R^{10}$, $CONR^9R^{10}$, $NR^9R^{10}$, $NHCOR^{10}$ and phenyl optionally substituted with 1 to 3 groups selected from $OR^9$, halo and $C_1$-$C_4$ alkyl;

wherein $R^9$ and $R^{10}$ are the same or different and are selected from H or $C_1$-$C_4$ alkyl and the * represent the attachment point to the carbonyl group;

wherein the group $Q^1$ is substituted at least with one hydroxy group;

or, if appropriate, their pharmaceutically acceptable salts and/or isomers, tautomers, solvates or isotopic variations thereof.

The compounds of formula (1) are agonists of the β2 receptors, that are particularly useful for the treatment of β2-mediated diseases and/or conditions, by showing excellent potency, in particular when administered via the inhalation route.

In the here above general formula (1), $C_1$-$C_4$ alkyl and $C_1$-$C_4$ alkylene denote a straight-chain or branched group containing 1, 2, 3 or 4 carbon atoms. This also applies if they carry substituents or occur as substituents of other radicals, for example in O—($C_1$-$C_4$)alkyl radicals, S—($C_1$-$C_4$)alkyl radicals etc. . . . Examples of suitable ($C_1$-$C_4$)alkyl radicals are methyl, ethyl, n-propyl, isopropyl, n-butyl, isobutyl, sec-butyl, tert-butyl. . . . Examples of suitable ($C_1$-$C_4$)alkoxy radicals are methoxy, ethoxy, n-propyloxy, isopropyloxy, n-butyloxy, iso-butyloxy, sec-butyloxy and tert-butyloxy . . . .

The $C_3$-$C_7$ cycloalkyl include cyclopropyl, cyclobutyl, cyclopentyl, cyclohexyl and cycloheptyl. Preferred $C_3$-$C_7$ cycloalkyl are substituted with OH.

Finally, halo denotes a halogen atom selected from the group consisting of fluoro, chloro, bromo and iodo in particular fluoro or chloro.

In the following, the free bond on the phenyl group such as in the structure below,

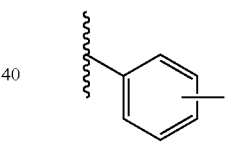

means that the phenyl can be substituted in the meta or para position.

The compounds of the formula (1)

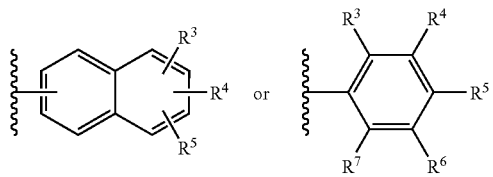
(1)

can be prepared using conventional procedures such as by the following illustrative methods in which $R^1$, $R^2$, $Q^1$, and n are as previously defined for the compounds of the formula (1) unless otherwise stated.

The amide derivatives of the formula (1) may be prepared by coupling an acid of formula (2) or a salt thereof:

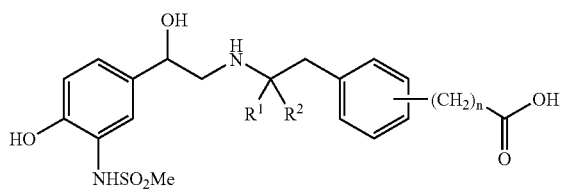

with an amine of formula NHR⁸-Q²-A (3),

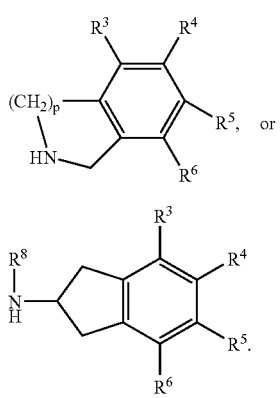

The coupling is generally carried out in an excess of said amine as an acid receptor, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane or ethyl acetate, and at temperature comprised between 10° C. and 40° C. (room temperature) for a period of 1-24 hours.

Said amine (3), (3') or (3") is either commercially available or may be prepared by conventional methods well known to the one skilled in the art (e.g. reduction, oxidation, alkylation, transition metal-mediated coupling, protection, deprotection etc. . . . ) from commercially available material.

The acid of formula (2) may be prepared from the corresponding ester of formula (4):

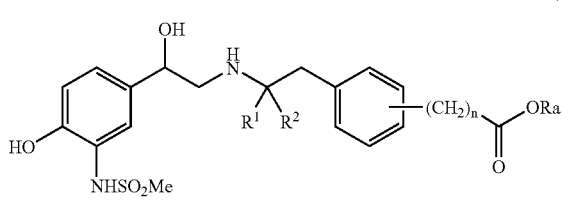

wherein Ra is a suitable acid protecting group, preferably a $(C_1-C_4)$alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, propionitrile, 1,4-dioxan, tetrahydrofuran/water), at a temperature comprised between 20° C. and 100° C., for a period of 1 to 40 hours.

The ester of formula (4) may be prepared by reaction of an amine of formula (5):

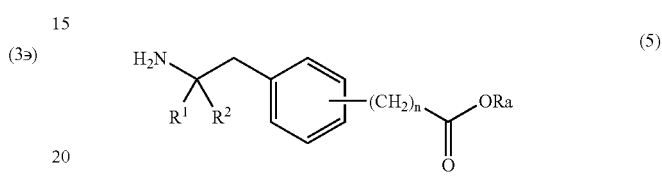

wherein Ra and n are as previously defined, with a bromide of formula (6):

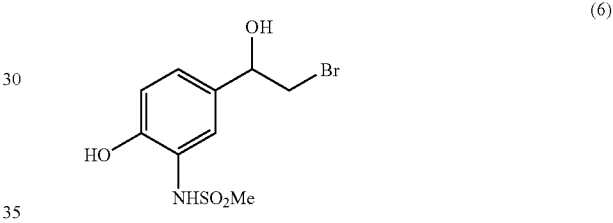

In a typical procedure, the amine of formula (5) is reacted with a bromide of formula (6) optionally in the presence of a solvent or mixture of solvents (e.g. dimethyl sulphoxide, toluene, N,N-dimethylformamide, propionitrile, acetonitrile), optionally in the presence of a suitable base (e.g. triethylamine, diisopropylethylamine, potassium carbonate, potassium hydrogen carbonate) at a temperature comprised between 80° C. and 120° C., for 12 to 48 hours.

The bromide of formula (6) may be prepared according to the method of WO 02/06258 (pg. 36, example 14a).

Alternatively, the ester of formula (4) where n=1 may be prepared from the bromide of formula (7):

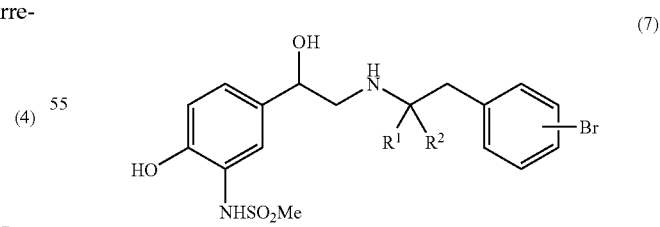

In a typical procedure the bromide (7) is treated with a suitable palladium catalyst (e.g. [1,1'-bis(diphenylphosphino)ferrocene]dichloro palladium(II)) under an atmosphere of carbon monoxide using RaOH as solvent (e.g. MeOH, EtOH) at elevated temperature (100° C.) and pressure (up to 100 psi) to give the ester of formula (4).

The amine of formula (5), where $R_1$ is Me and $R_2$ is H, may be prepared as either the (R) or (S) enantiomer from the corresponding protected amine of formula (8):

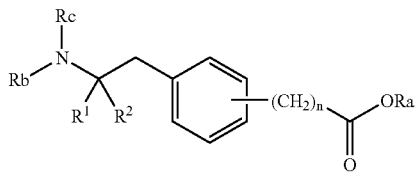

(8)

wherein Ra and n are as previously defined and Rb and Rc represent any suitable substituents so that HNRbRc is a chiral amine (for example, Rb may be hydrogen and Rc may be α-methylbenzyl), provided that the bonds between N and Rb and N and Rc can be easily cleaved to give the free amine of formula (5) using standard methodology for cleaving nitrogen protecting groups, such as those found in the text book T. W. GREENE, Protective Groups in Organic Synthesis, A. Wiley-Interscience Publication, 1981.

The amine of formula (8) may be prepared as a single diastereomer by reaction of an amine of formula HNRbRc with a ketone of formula (9):

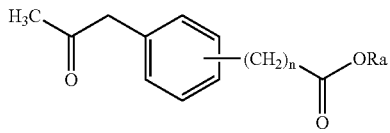

(9)

wherein Ra, Rb, Rc and n are as previously defined.

In a typical procedure, the reaction of the ketone of formula (9) with the amine of formula HNRbRc leads to a chiral intermediate which is in turn reduced by a suitable reducing agent (e.g. sodium cyanoborohydride of formula $NaCNBH_3$ or sodium triacetoxyborohydride of formula $Na(OAc)_3BH$) optionally in the presence of a drying agent (e.g. molecular sieves, magnesium sulfate) and optionally in the presence of an acid catalyst (e.g. acetic acid) to give the amine of formula (8) as a mixture of diastereomers. The reaction is generally done in a solvent such as tetrahydrofuran or dichloromethane at a temperature comprised between 20° C. and 80° C. for 3 to 72 hours. The resulting product is then converted to the hydrochloride salt and selectively crystallised from a suitable solvent or mixture of solvents (e.g. isopropanol, ethanol, methanol, diisopropyl ether or diisopropyl ether/methanol) to give (8) as a single diastereomer.

The ketone of formula (9) where n=1 may be prepared by palladium mediated coupling of an aryl halide of formula (10):

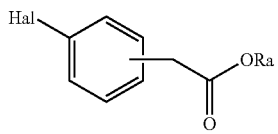

(10)

wherein Ra is as previously defined and Hal represents an halogen atom, which includes, but is not limited to bromo and iodo, with an enolate or enolate equivalent.

In a typical procedure, the aryl halide of formula (10) is reacted with a tin enolate generated in-situ by treatment of isoprenyl acetate with tri-n-butyltin methoxide of formula $Bu_3SnOMe$ in the presence of a suitable palladium catalyst (palladium acetate/tri-ortho-tolylphosphine of formula $Pd(OAc)_2/P(o-Tol)_3$) in a non-polar solvent (e.g. toluene, benzene, hexane). Preferably, the reaction is carried out at a temperature comprised between 80° C. and 110° C. for 6 to 16 hours.

The aryl halide of formula (10) may be obtained by esterification of the corresponding acid of formula (11):

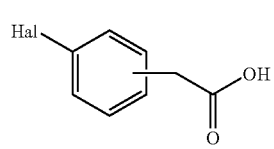

(10)

wherein Hal is as previously defined, according to any method well-known to the one skilled in the art to prepare an ester from an acid, without modifying the rest of the molecule.

In a typical procedure, the acid of formula (11) is reacted with an alcoholic solvent of formula RaOH, wherein Ra is as previously defined, in the presence of an acid such as hydrogen chloride at a temperature between 10° C. and 40° C. (room temperature) for 8 to 16 hours.

The acid of formula (11) is a commercial product.

The amine of formula (5), where $R_1=R_2=$alkyl, may be prepared according to the following scheme:

Scheme 1

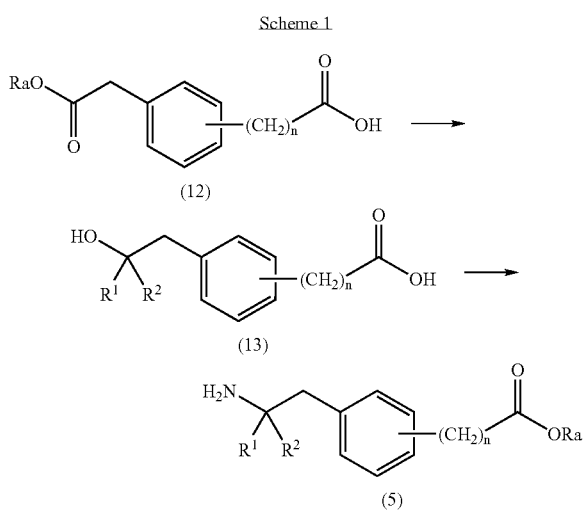

wherein $R^1$, $R^2$ and Ra are as previously defined.

In a typical procedure, the ester of formula (12) is reacted with an "activated" alkyl (organometallic alkyl such as $R^2MgBr$, $R^2MgCl$ or $R^2Li$) to give the corresponding tertiary alcohol of formula (13) using the method described above.

Said tertiary alcohol of formula (13) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting aminoacid is then esterified using the method described herein to give the amine of formula (5).

Alternatively, the amine of formula (5), where $R^1=R^2=C_1-C_4$ alkyl and n=0, may be prepared according to the following scheme:

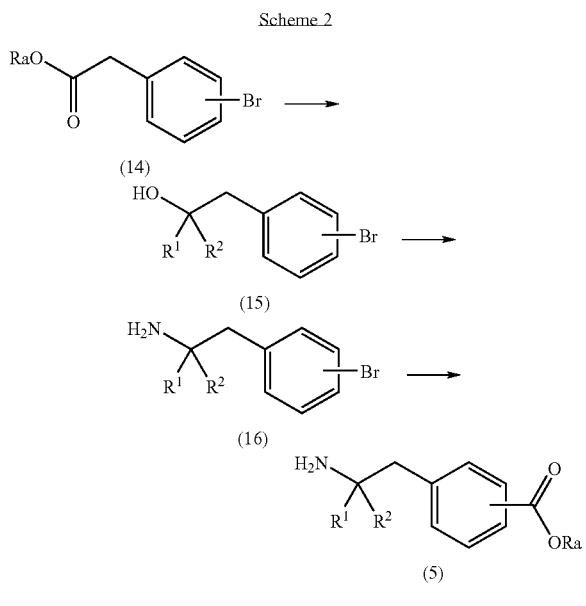

wherein $R^1$, $R^2$ and Ra are as previously defined.

In a typical procedure, the ester of formula (14) is reacted with an "activated" alkyl (organometallic alkyl such as $R^2MgBr$, $R^2MgCl$ or $R^2Li$) to give the corresponding tertiary alcohol of formula (15) using the method described above.

Said tertiary alcohol of formula (15) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks to give the bromo amine (16).

The resulting bromo amine (16) is treated with a suitable palladium catalyst (e.g. [1,1'-bis(diphenylphosphino)ferrocene]dichloropalladium(II)) under an atmosphere of carbon monoxide using RaOH as solvent (e.g. MeOH, EtOH) at elevated temperature (100° C.) and pressure (100 psi) to give the ester of formula (5).

The ketone of formula (9) where n=2 may be prepared by reduction of an alkene of formula (17):

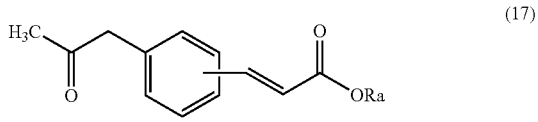

In a typical procedure, a solution of the olefin of formula (17) in a suitable solvent (e.g. methanol, ethanol, ethyl acetate) is treated with a palladium catalyst (e.g. 10% palladium on charcoal) and stirred under an atmosphere of hydrogen, optionally at elevated pressure (e.g. 60 psi), at temperature between room temperature and 60° C. for 8-24 hours.

The alkene of formula (17) may be prepared by a palladium mediated coupling of an activated olefin with an aryl halide of formula (18):

In a typical procedure, the aryl halide (18) is coupled with a vinyl ester (e.g. methyl acrylate) in the presence of a suitable palladium catalyst (e.g. tetrakis(triphenylphosphine)palladium(0) of formula $Pd(PPh_3)_4$, palladium acetate/tri-ortho-tolylphosphine of formula $Pd(OAc)_2/P(o\text{-}tol)_3$ or (diphenylphosphino)ferrocenyl palladium chloride of formula $dppfPdCl_2$) in a suitable solvent (e.g. acetonitrile, N,N-dimethylformamide, toluene), optionally in the presence of a base such as triethylamine at a temperature between 40° C. and 110° C. for 8 to 24 hours.

The ketone of formula (18) is a commercial product.

The amine of formula (5), where $R^1$ and $R^2$ are both H, may be prepared according to the following scheme:

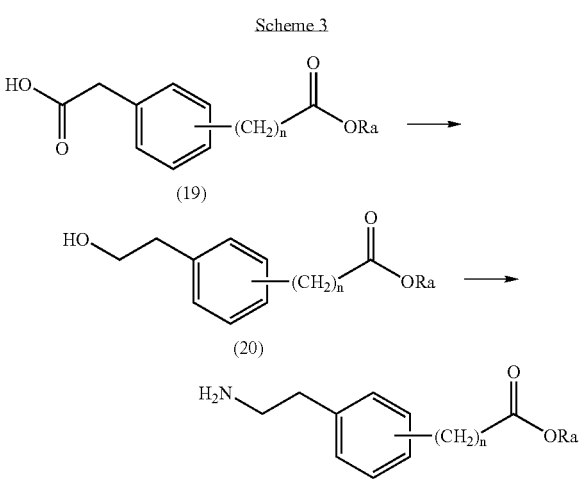

wherein $R^1$, $R^2$ and Ra are as previously defined.

In a typical procedure, the acid of formula (19) is preferentially reduced to the corresponding alcohol (20) in the presence of the ester. This may be performed by formation of the acyl imidazole or mixed anhydride and subsequent reduction with sodium borohydride or another suitable reducing agent.

Said primary alcohol of formula (20) is then converted into a leaving group such as mesylate, tosylate, bromide or iodide and displaced with appropriate amine nucleophile. The preferred nucleophile is azide ion which can then be reduced to the primary amine via hydrogenation or triphenylphosphine. Alternative nucleophiles could include ammonia or alkylamines such as benzylamine or allylamine and subsequent cleavage of the alkyl group to furnish the amine.

In a typical procedure, the compounds of formula (I) wherein $R^1$ and $R^2$ are both methyl and n is 1, may be prepared by reacting a compound of formula (21)

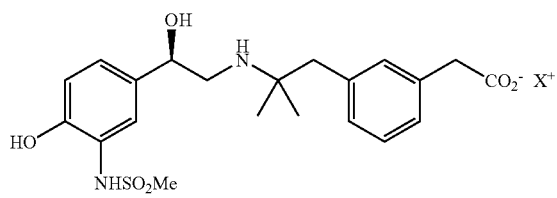
(21)

where X is H, K, Na, Li and potentially an organic amine base or other metal salt, with a suitable amine of formula NHR$^8$-Q$^2$-A (3)

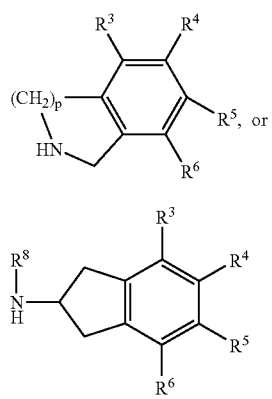
(3')

(3'')

in the presence of a conventional coupling agent such as 1-(3-dimethylaminopropyl)-3-ethylcarbodiimide hydrochloride or dicyclohexylcarbodiimide in a suitable solvent such as pyridine dimethylformamide and dimethylacetamide optionally in the presence of an organic base (such as Hunig's base) and an additive (such as 1-hydroxybenzotriazole) in order to obtain a compound of formula (1):

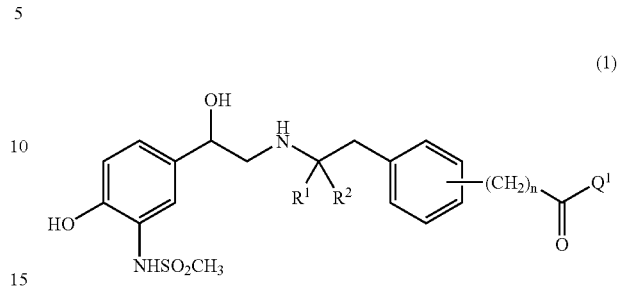
(1)

wherein R$^1$ and R$^2$ are methyl and n is 1.

Said compound of formula (21) may be obtained by hydrogenation of a compound of formula (22)

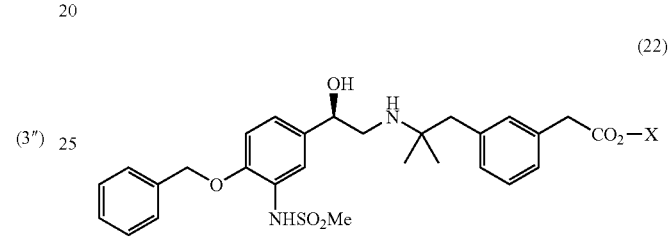
(22)

wherein X is H, Na, Li or K and an potentially an organic amine or other metal salts, in the presence of a suitable solvent such as methanol, IPA, THF and water and in the presence of a suitable catalyst such as palladium hydroxide on carbon or palladium on carbon.

Said compound of formula (22) may be obtained by reacting a compound of formula (23)

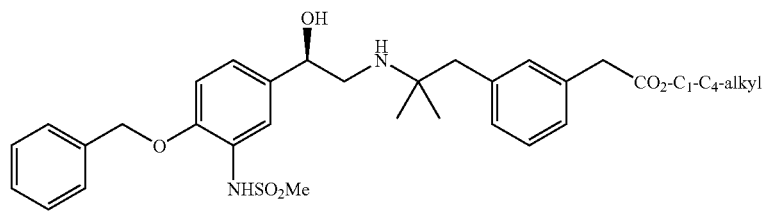
(23)

with M—OH wherein M is selected from Na, K or Li, optionally in the presence of a suitable solvent such as propionitrile, tetrahydrofuran or dioxane, preferably propionitrile.

Said compound of formula (23) may be obtained by deprotecting a compound of formula (24)

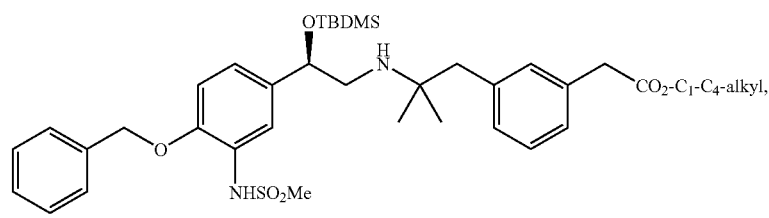
(24)

using a deprotecting agent such as tetrabutylammonium fluoride, HF, or triethylamine trihydrofluoride in the presence of a suitable solvent such as propionitrile.

Said compound of formula (24) may be obtained by reacting a compound of formula

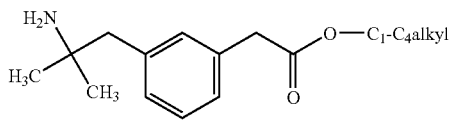

with a compound of formula

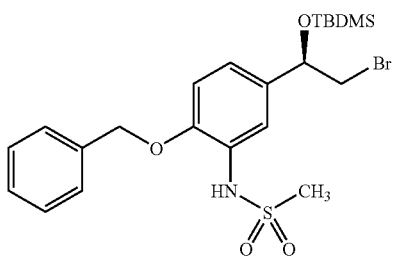

in the presence of a suitable solvent such as propionitrile, THF, toluene, ethyl acetate, acetonitrile, propionitrile, dioxane, DMF, DMSO, and optionally in the presence of a base such as sodium hydrogen carbonate, potassium hydrogen carbonate, Hunig's base or triethylamine, at a temperature between 50° C. and 150° C. for 12 to 36 hours.

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

Preferably $Q^2$ is —$CH_2$—, —$(CH_2)_2$—, —$(CH_2)_3$—, —$C(CH_3)_2$—, —$(CH_2)_4$— or —$(CH(CH_2OH))$—.

Preferably, $Q^1$ is

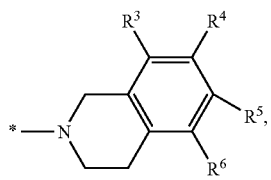

wherein one of $R_3$, $R_4$, $R_5$ and $R_6$ is OH and the others are H.

Preferably $Q^1$ is

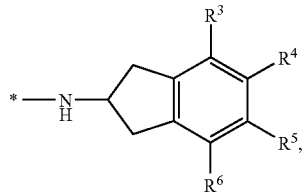

wherein one of $R_3$, $R_4$, $R_5$ and $R_6$ is OH and the others are H.

Preferably $Q^1$ is a group *—$NR^8$-$Q^2$-A, wherein $R^8$ is H, $CH_3$ or $CH_2CH_3$, $Q^2$ is a $C_1$-$C_4$ alkylene and A is naphtyl substituted by one hydroxy.

Preferably, $Q^1$ is a group *—$NR^8$-$Q^2$-A, wherein $R^8$ is H, $CH_3$ or $CH_2CH_3$, $Q^2$ is a $C_1$-$C_4$ alkylene and A is a group

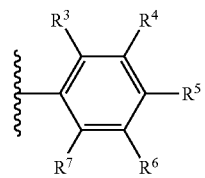

wherein one of $R^3$, $R^4$, $R^5$, $R^6$ and $R^7$ is OH and the others are the same or different and are selected from H, $C_1$-$C_4$ alkyl, $OR^9$, $SR^9$, halo, $CF_3$, $OCF_3$, $SO_2NR^9R^{10}$, $CONR^9R^{10}$, $NR^9R^{10}$, $NHCOR^{10}$, provided at least 2 of $R^3$ to $R^7$ are equal to H;

wherein $R^9$ and $R^{10}$ are the same or different and are selected from H or $C_1$-$C_4$ alkyl.

More preferably, $Q^1$ is a group *—NH-$Q^2$-A, wherein $Q^2$ is a —$CH_2$—, —$(CH_2)_2$—, —$(CH_2)_4$—, —$CH_2$—$C(CH_3)_2$— preferably —$CH_2$—, and A is a group

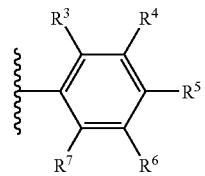

wherein one of $R^3$, $R^4$, $R^5$, $R^5$ and $R^7$ is OH and the others are the same or different and are selected from H, OH, $CH_3$, $OCH_2$—$CH_3$, $SCH_3$, halo, $CF_3$, $OCF_3$, provided at least 2 of $R^3$ to $R^7$ are equal to H.

Preferably, $Q^1$ is a group *—$NR^8$-$Q^2$-A, wherein $R^8$ is H, $CH_3$ or $CH_2CH_3$, $Q^2$ is a $C_1$-$C_4$ alkylene and A is a group

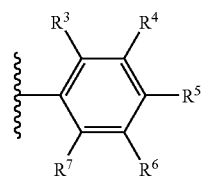

wherein one of $R^3$, $R^4$, $R^5$, $R^6$ and $R^7$ is phenyl substituted by OH and the others are H.

In the above groups of compounds, the following substituents are particularly preferred:

$R^1$ is H or $C_1$-$C_4$ alkyl and $R^2$ is $C_1$-$C_4$ alkyl. More preferably, $R^1$ is H or $CH_3$ and $R^2$ is $CH_3$.

n is 0 or 1. More preferably n is 1.

$R^1$ is H and $R^2$ is $CH_3$ and n is 1.

$R^1$ is $CH_3$, $R^2$ is $CH_3$ and n is 1.

Particularly preferred are the compounds of the formula (1) as described in the Examples section hereafter, i.e.:

2-(3-{2-[((2R)-2-Hydroxy-2-{4-hydroxy-3-[(methylsulfonyl)amino]phenyl}ethyl)amino]-2-methylpropyl}phenyl)-N-(4-hydroxy-3-methoxybenzyl)acetamide;

N-[(4'-Hydroxybiphenyl-4-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-(4-Chloro-2-hydroxybenzyl)-2-(3-{2-[((2R)-2-hydroxy-2-{4-hydroxy-3-[(methylsulfonyl)amino]phenyl}ethyl)amino]-2-methylpropyl}phenyl)acetamide;

N-(4-Hydroxy-3,5-dimethylbenzyl)-2-(3-{2-[((2R)-2-hydroxy-2-{4-hydroxy-3-[(methylsulfonyl)amino]phenyl}ethyl)amino]-2-methylpropyl}phenyl)acetamide;

2-(3-{2-[((2R)-2-Hydroxy-2-{4-hydroxy-3-[(methylsulfonyl)amino]phenyl}ethyl)amino]-2-methylpropyl}phenyl)-N-[(2-hydroxy-1-naphthyl)methyl]acetamide;

2-(3-{2-[((2R)-2-Hydroxy-2-{4-hydroxy-3-[(methylsulfonyl)amino]phenyl}ethyl)amino]-2-methylpropyl}phenyl)-N-[(6-hydroxy-2-naphthyl)methyl]acetamide;

N-[(4'-Hydroxybiphenyl-3-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-[(3'-Hydroxybiphenyl-3-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

2-(3-{2-[((2R)-2-Hydroxy-2-{4-hydroxy-3-[(methylsulfonyl)amino]phenyl}ethyl)amino]-2-methylpropyl}phenyl)-N-[2-(4-hydroxyphenyl)-2-methylpropyl]acetamide;

N-(3,5-Dichloro-2-hydroxybenzyl)-N-ethyl-2-(3-{2-[((2R)-2-hydroxy-2-{4-hydroxy-3-[(methylsulfonyl)amino]phenyl}ethyl)amino]-2-methylpropyl}phenyl)acetamide;

2-(3-{2-[((2R)-2-Hydroxy-2-{4-hydroxy-3-[(methylsulfonyl)amino]phenyl}ethyl)amino]-2-methylpropyl}phenyl)-N-[(6-hydroxy-1-naphthyl)methyl]-N-methylacetamide;

N-[(2'-Hydroxybiphenyl-3-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-(2-Hydroxy-5-{(1R)-1-hydroxy-2-[(2-{3-[2-(6-hydroxy-3,4-dihydroisoquinolin-2(1H)-yl)-2-oxoethyl]phenyl}-1,1-dimethylethyl)amino]ethyl}phenyl)methanesulfonamide;

2-(3-{2-[((2R)-2-Hydroxy-2-{4-hydroxy-3-[(methylsulfonyl)amino]phenyl}ethyl)amino]-2-methylpropyl}phenyl)-N-[4-(4-hydroxyphenyl)butyl]acetamide;

2-(3-{2-[((2R)-2-Hydroxy-2-{4-hydroxy-3-[(methylsulfonyl)amino]phenyl}ethyl)amino]-2-methylpropyl}phenyl)-N-[2-(4-hydroxyphenyl)ethyl]acetamide;

N-(2-Chloro-4-hydroxybenzyl)-2-(3-{2-[((2R)-2-hydroxy-2-{4-hydroxy-3-[(methylsulfonyl)amino]phenyl}ethyl)amino]-2-methylpropyl}phenyl)acetamide N-(3,5-Dichloro-4-hydroxybenzyl)-2-(3-{2-[((2R)-2-hydroxy-2-{4-hydroxy-3-[(methylsulfonyl)amino]phenyl}ethyl)amino]-2-methylpropyl}phenyl)acetamide;

N-(2,3-Dichloro-4-hydroxybenzyl)-2-(3-{2-[((2R)-2-hydroxy-2-{4-hydroxy-3-[(methylsulfonyl)amino]phenyl}ethyl)amino]-2-methylpropyl}phenyl)acetamide;

2-(3-{2-[((2R)-2-Hydroxy-2-{4-hydroxy-3-[(methylsulfonyl)amino]phenyl}ethyl)amino]-2-methylpropyl}phenyl)-N-[(4-hydroxy-1-naphthyl)methyl]acetamide;

2-(3-{2-[((2R)-2-Hydroxy-2-{4-hydroxy-3-[(methylsulfonyl)amino]phenyl}ethyl)amino]-2-methylpropyl}phenyl)-N-[3-hydroxy-5-(trifluoromethyl)benzyl]acetamide;

N-(2-Chloro-4-hydroxybenzyl)-N-ethyl-2-(3-{2-[((2R)-2-hydroxy-2-{4-hydroxy-3-[(methylsulfonyl)amino]phenyl}ethyl)amino]-2-methylpropyl}phenyl)acetamide;

N-(2-Chloro-4-hydroxybenzyl)-2-(3-{2-[((2R)-2-hydroxy-2-{4-hydroxy-3-[(methylsulfonyl)amino]phenyl}ethyl)amino]-2-methylpropyl}phenyl)-N-methylacetamide;

N-(3-Fluoro-5-hydroxybenzyl)-2-(3-{2-[((2R)-2-hydroxy-2-{4-hydroxy-3-[(methylsulfonyl)amino]phenyl}ethyl)amino]-2-methylpropyl}phenyl)-N-methylacetamide;

N-[(2'-Hydroxybiphenyl-2-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-[(3'-Hydroxybiphenyl-2-yl)methyl]-2-(3-{2-[((2R)-2-hydroxy-2-{-hydroxy-3-[(methylsulfonyl)amino]phenyl}ethyl)amino]-2-methylpropyl}phenyl)acetamide;

N-(4-Hydroxy-2,6-dimethylbenzyl)-2-(3-{2-[((2R)-2-hydroxy-2-{4-hydroxy-3-[(methylsulfonyl)amino]phenyl}ethyl)amino]-2-methylpropyl}phenyl)acetamide;

N-(2-Hydroxy-5-{(1R)-1-hydroxy-2-[(2-{3-[2-(7-hydroxy-3,4-dihydroisoquinolin-2(1H)-yl)-2-oxoethyl]phenyl}-1,1-dimethylethyl)amino]ethyl}phenyl)methanesulfonamide;

N-(2-Hydroxy-5-{(1R)-1-hydroxy-2-[(2-{3-[2-(5-hydroxy-3,4-dihydroisoquinolin-2(1H)-yl)-2-oxoethyl]phenyl}-1,1-dimethylethyl)amino]ethyl}phenyl)methanesulfonamide;

2-(3-{2-[((2R)-2-Hydroxy-2-{4-hydroxy-3-[(methylsulfonyl)amino]phenyl}ethyl)amino]-2-methylpropyl}phenyl)-N-[(1R)-2-hydroxy-1-phenylethyl]acetamide;

2-(3-{2-[((2R)-2-Hydroxy-2-{4-hydroxy-3-[(methylsulfonyl)amino]phenyl}ethyl)amino]-2-methylpropyl}phenyl)-N-[(1S)-2-hydroxy-1-phenylethyl]acetamide;

N-[(3'-Hydroxybiphenyl-4-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-[(2'-Hydroxybiphenyl-4-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide;

N-[(4'-Hydroxybiphenyl-4-yl)methyl]-3-{2-[((2R)-2-hydroxy-2-{4-hydroxy-3-[(methylsulfonyl)amino]phenyl}ethyl)amino]-2-methylpropyl}benzamide;

3-{2-[((2R)-2-Hydroxy-2-{4-hydroxy-3-[(methylsulfonyl)amino]phenyl}ethyl)amino]-2-methylpropyl}-N-[2-(4-hydroxyphenyl)-2-methylpropyl]benzamide;

N-[(4'-Hydroxybiphenyl-3-yl)methyl]-3-{2-[((2R)-2-hydroxy-2-{4-hydroxy-3-[(methylsulfonyl)amino]phenyl}ethyl)amino]-2-methylpropyl}benzamide;

N-[2-(4-Hydroxy-2,5-dimethylphenyl)ethyl]-3-{2-[((2R)-2-hydroxy-2-{4-hydroxy-3-[(methylsulfonyl)amino]phenyl}ethyl)amino]-2-methylpropyl}benzamide;

N-[2-(4-Hydroxy-2,3-dimethylphenyl)ethyl]-3-{2-[((2R)-2-hydroxy-2-{4-hydroxy-3-[(methylsulfonyl)amino]phenyl}ethyl)amino]-2-methylpropyl}benzamide; and, 3-{2-[((2R)-2-Hydroxy-2-{4-hydroxy-3-[(methylsulfonyl)amino]phenyl}ethyl) amino]-2-methylpropyl}-N-[2-(4-hydroxy-3-methylphenyl)ethyl]benzamide.

According to one aspect of the present invention, the compounds of formula (I) wherein the $(CH_2)_n$—C(=O)Q$^1$ group is in the meta position are generally preferred.

Pharmaceutically acceptable salts of the compounds of formula (1) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:

(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:

(i) where the compound of formula (1) contains a carboxylic acid functionality (—COOH), an ester thereof, for example, a compound wherein the hydrogen of the carboxylic acid functionality of the compound of formula (1) is replaced by $(C_1-C_8)$alkyl;
(ii) where the compound of formula (1) contains an alcohol functionality (—OH), an ether thereof, for example, a compound wherein the hydrogen of the alcohol functionality of the compound of formula (1) is replaced by $(C_1-C_6)$alkanoyloxymethyl; and
(iii) where the compound of formula (1) contains a primary or secondary amino functionality (—NH$_2$ or —NHR where R≠H), an amide thereof, for example, a compound wherein, as the case may be, one or both hydrogens of the amino functionality of the compound of formula (1) is/are replaced by $(C_1-C_{10})$alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include (i) where the compound of formula (1) contains a methyl group, an hydroxymethyl derivative thereof (—CH$_3$→—CH$_2$OH):
(ii) where the compound of formula (1) contains an alkoxy group, an hydroxy derivative thereof (—OR→—OH);
(iii) where the compound of formula (1) contains a tertiary amino group, a secondary amino derivative thereof (—NR$^1$R$^2$→—NHR$^1$ or —NHR$^2$);
(iv) where the compound of formula (1) contains a secondary amino group, a primary derivative thereof (—NHR$^1$→—NH$_2$);

(v) where the compound of formula (1) contains a phenyl moiety, a phenol derivative thereof (-Ph→-PhOH); and
(vi) where the compound of formula (1) contains an amide group, a carboxylic acid derivative thereof (—CONH$_2$→COOH).

Compounds of formula (1) containing one or more asymmetric carbon atoms can exist as two or more stereoisomers. Where a compound of formula (1) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

According to one aspect of the present invention, the (R,R)-stereoisomer of the formula below, wherein R$^1$ is hydrogen and R$^2$ is C$_1$-C$_4$ alkyl, preferably methyl, and n and Q$^1$ are as defined above, is generally preferred:

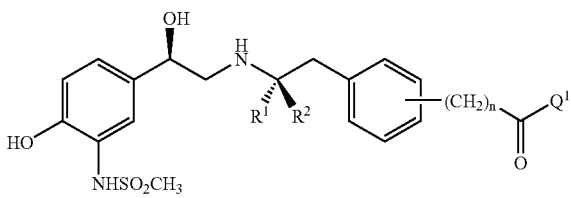

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (1), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the_effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more $\beta 2$ agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists, (b) Leukotriene antagonists (LTRAs) including antagonists of $LTB_4$, $LTC_4$, $LTD_4$, and $LTE_4$, (c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids, such as DAGR (dissociated agonists of the corticoid receptor)
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the $NF_{\kappa\beta}$ pathway, e.g. IKK inhibitors,
(w) modulators of cytokine signalling pathways such as p38 MAP kinase, syk kinase or JAK kinase inhibitor
(x) Agents that can be classed as mucolytics or anti-tussive, and
(y) Antibiotics.

According to the present invention, combination of the compounds of formula (1) with:
H3 antagonists,
Muscarinic M3 receptor antagonists,
PDE4 inhibitors,
glucocorticosteroids,
Adenosine A2a receptor agonists,
Modulators of cytokine signalling pathways such as p38 MAP kinase or syk kinase, or,
Leukotriene antagonists (LTRAs) including antagonists of $LTB_4$, $LTC_4$, $LTD_4$, and $LTE_4$, are further preferred.

According to the present invention, combination of the compounds of formula (1) with:
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine, are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the $\beta 2$ receptor and thereby have a wide range of therapeutic applications, as described further below, because of the essential role which the $\beta 2$ receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the $\beta 2$ receptor is involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a $\beta 2$ agonist activity. In particular, the present inventions concerns the use of the compounds of formula (1), or pharmaceutically acceptable salts, derived forms or compositions thereof, for the manufacture of a drug for the treatment of $\beta 2$-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a $\beta 2$-mediated diseases and/or conditions in a mammal, including a human being, in particular the diseases and/or conditions listed above, comprising administering said mammal with an effective amount of a compound of formula (1), its pharmaceutically acceptable salts and/or derived forms.

The following examples illustrate the preparation of the compounds of the formula (1):

Preparation 1: Diethyl 2,2'-(1,3-phenylene)diacetate

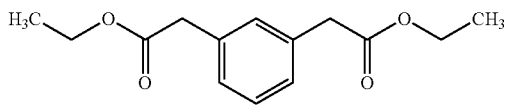

Acetyl chloride (12.5 ml, 175 mmol) was added to a suspension of 2,2'-(1,3-phenylene)diacetic acid (50.0 g, 260 mmol) in ethanol (500 ml) and the resulting solution heated to reflux for 16 hours. The reaction was cooled to room temperature and the solvent removed in vacuo. The residue was partitioned between saturated aqueous sodium hydrogencarbonate (300 ml) and ethyl acetate (500 ml). The organic phase was washed with water (200 ml), sat. aq. sodium chloride (300 ml), dried (sodium sulfate) and the solvent removed in vacuo to give the title compound as a pale yellow oil (63.5 g).
$^1$HNMR (CDCl$_3$, 400 MHz) δ: 1.31 (t, 6H), 3.65 (s, 4H), 4.20 (q, 4H), 7.24-7.36 (m, 4H) ppm.
MS (electrospray): m/z 251 [M+H]$^+$ Preparation 2: [3-(2-Oxo-propyl)-phenyl]-acetic acid ethyl ester

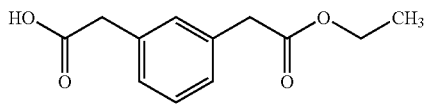

A solution of the diester from preparation 1 (44.3 g, 177 mmol) and 2,2'-(1,3-phenylene)diacetic acid (59.2, 308 mmol) in ethanol (24 ml) and dioxan (290 ml) was treated dropwise with 12M hydrochloric acid (4.9 ml, 58.8 mmol). The reaction mixture was stirred at reflux for 18 hours before being allowed to cool and concentrated to low volume. The reaction mixture was diluted with toluene (125 ml) and the resulting slurry filtered. The filtrate was concentrated in vacuo and the residue taken up in water and basified with sodium bicarbonate until pH neutral. The mixture was diluted with ethyl acetate (200 ml) and the organic layer was separated and washed with sodium bicarbonate solution (5×30 ml) and saturated aqueous sodium chloride (50 ml). The combined aqueous extracts were acidified to pH 3 with 6M hydrochloric acid and extracted with ether (3×30 ml). The organics were combined, dried (magnesium sulphate) and concentrated in vacuo. The residue was triturated with pentane giving the title compound as a colourless solid 10.8 g.
$^1$HNMR (CD$_3$OD, 400 MHz) δ: 1.25 (t, 3H), 3.60 (m, 2H), 3.63 (m, 2H), 4.15 (q, 2H), 7.18-7.32 (m, 4H) ppm.
MS (electrospray): m/z 245 [MNa]$^+$ Preparation 3: [3-(2-Hydroxy-2-methyl-propyl)-phenyl]-acetic acid

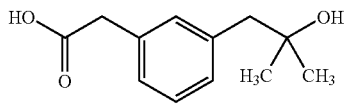

Methyl magnesium chloride (51 ml of a 3M solution in tetrahydrofuran, 153 mmol) was added dropwise to a stirred solution of the preparation 2 (11.6 g, 51 mmol) (International Journal of Peptide and Protein Research, 1987, 29(3), 331) in tetrahydrofuran (300 ml) at 0° C. under nitrogen. The reaction was allowed to warm to room temperature overnight with the formation of a thick white precipitate and then water (50 ml) and 2N hydrochloric acid (80 ml) were cautiously added. The aqueous was extracted with ethyl acetate (2×300 ml) and the combined organics washed with brine (50 ml), dried (sodium sulfate), and the solvent removed in vacuo to furnish the title compound as a golden oil (11.2 g).
$^1$HNMR (CDC$_3$, 400 MHz) δ: 1.22 (6H, s), 2.75 (2H, s), 3.63 (2H, s), 7.12-7.30 (4H, m).
MS (ESI): m/z 209 [M+H]$^+$ Preparation 4: {3-[2-(2-Chloro-acetylamino)-2-methyl-propyl]-phenyl}-acetic acid

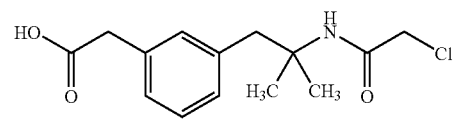

2-Chloroacetonitrile (8.8 ml, 140 mmol) was added to a solution of the alcohol from preparation 3 (16.0 g, 70 mmol), in acetic acid (33 ml). The resulting solution was cooled to 0° C., treated with concentrated sulphuric add (33 ml), and the reaction mixture allowed to warm gradually to room temperature. After 4 hours the reaction mixture was poured onto ice and basified with solid sodium carbonate. The solution was extracted with ethyl acetate (2×500 ml) and the combined organic extracts dried (magnesium sulphate) and concentrated in vacuo to give the title product as a colourless solid (19.0 g).
$^1$HNMR (CDCl$_3$, 400 MHz) δ: 1.36 (s, 6H), 3.02 (s, 2H), 3.62 (s, 2H), 3.95 (s, 2H), 6.19 (m, 1H), 7.06-7.31 (m, 4H) ppm.
MS (electrospray): m/z 282 [M–H]$^-$ Preparation 5:
[3-(2-Amino-2-methyl-propyl)-phenyl]-acetic acid methyl ester

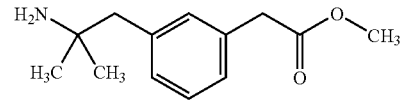

A solution of the amide from preparation 4 (5.1 g, 18 mmol), thiourea (1.6 g, 21 mmol) and acetic acid (18 ml) in ethanol (80 ml) was heated to reflux under a nitrogen atmosphere for 16 hours. The reaction mixture was allowed to cool to room temperature and filtered. The filtrate was concentrated in vacuo, the residue dissolved in methanol (150 ml), saturated with hydrogen chloride gas and the resulting solution heated to reflux for 16 hours. The mixture was concentrated in vacuo and the residue partitioned between ethyl acetate (200 ml) and 5% aqueous sodium carbonate solution (200 ml). The organic phase was washed with brine (100 ml), dried (magnesium sulphate) and concentrated in vacuo. The residue was purified by strong cation exchange resin, eluting with methanol and then a 2M solution of ammonia in methanol, to elute the product. The eluent was concentrated in vacuo giving the title compound as a yellow oil, 2.68 g.
$^1$HNMR (CDCl$_3$, 400 MHz) δ: 1.14 (s, 6H), 2.68 (s, 2H), 3.62 (s, 2H), 3.69 (s, 3H), 7.08-7.16 (m, 3H), 7.23-7.27 (m, 1H) ppm.
MS (electrospray): m/z 222 [M+H]$^+$ Preparation 6: N-{2-(benzyloxy)-5-[(1R)-2-bromo-1-hydroxyethyl]phenyl}methanesulfonamide

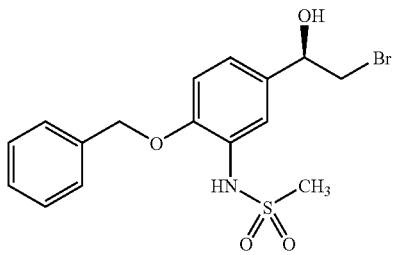

A solution of (1R)-1-[3-amino-4-(benzyloxy)phenyl]-2-bromoethanol (Org. Process Research and Development, 1998, 2, 96) (30.8 g, 95.6 mmol) in dichloromethane (300 ml) was treated with pyridine (9.3 ml, 115 mmol). The resulting solution was cooled to 5° C. and a solution of methanesulfonyl chloride (7.8 ml, 100.7 mmol) in dichloromethane (10 ml) added dropwise. The mixture was stirred at 5° C. for a further 30 minutes and then allowed to warm gradually to room temperature over a period of 16 hours. The reaction mixture was washed with 2N hydrochloric acid (110 ml) and the organic phase separated, dried (magnesium sulfate) and the solvent removed in vacuo to give an orange oil. The residue was crystallized from hot toluene (100 ml) to give the title compound as a pale pink solid (33.7 g).

$^1$HNMR (DMSOd$_6$, 400 MHz) δ: 2.93 (s, 3H), 3.52-3.66 (m, 2H), 4.74 (m, 1H), 5.19 (s, 2H), 7.11 (d, 1H), 7.19-7.22 (m, 1H), 7.33-7.36 (m, 2H), 7.40-7.43 (m, 2H), 7.56 (d, 2H), 8.95 (s, 1H) ppm.

MS (electrospray): m/z 398/400 [M−H]−

Preparation 7: N-[2-(benzyloxy)-5-((1R)-2-bromo-1-{[tert-butyl(dimethyl) silyl]oxy}ethyl)phenyl]methanesulfonamide

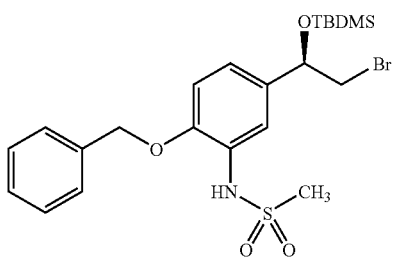

A solution of the bromide of preparation 6 (21.5 g, 53.7 mmol) in N,N-dimethylformamide (125 ml) was treated with imidazole (4.16 g, 75.2 mmol) and tert-butyl(dimethyl)silylchloride (9.73 g, 64.5 mmol) and the resulting solution left to stir at room temperature for 16 hours. The reaction mixture was diluted with ethyl acetate (200 ml) and washed with water (2×100 ml). The aqueous phases were combined and extracted with ethyl acetate (100 ml). The combined organic extracts were washed with 2N hydrochloric acid (100 ml), dried (magnesium sulphate) and reduced in vacuo. The residue was suspended in pentane:ethyl acetate (200 ml, 1:1 by volume) and the solvent evaporated. The residue was triturated with further pentane:ethyl acetate (200 ml, 1:1 by volume) and the resulting solid filtered off and dried in vacuo to give the title compound as a colourless solid (23.7 g).

$^1$HNMR (CDCl$_3$, 400 MHz) δ: −0.07 (s, 3H), 0.11 (s, 3H), 0.89 (s, 9H), 2.91 (s, 3H0, 4.80-4.83 (m, 1H), 6.80 (bs, 1H), 6.98 (d, 1H), 7.12 (d, 1H), 7.36-7.44 (m, 5H), 7.52-7.54 (m, 1H) ppm.

Alternative Process for the Preparation of Preparation 7:

A solution of the bromide of preparation 6 (10 g, 24.98 mmol) was dissolved in DCM (20 ml, 2 ml/g) and then imidazole (4.58 g, 37.47 mmol, 1.5 eq) was added followed by TBDMSiCl (5.27 g, 34.97 mmol, 1.4 eq). The reaction mixture was heated to reflux for 1 hour and then allowed to cool to 30° C. The mixture was diluted with isopropyl acetate (80 ml, 8 ml/g) and then quenched with 2M HCl (50, 5 ml/g) and stirred vigorously for 10 minutes. The phases were separated and the organic phase was washed with water (50 ml, 5 ml/g). The organic phase was then reduced in volume under reduced pressure at 45° C. to 25-30 ml. The solution was then cooled to room temperature and a suspension quickly formed and was stirred at room temperature for 30 minutes. Heptane (20 ml, 2 ml/g) was then added over 10 minutes and the suspension was cooled to 5-10° C. and stirred for 1 hour. The suspension was then filtered and washed on the filter paper with heptane (2×10 ml). The resulting filter cake was dried in a vacuum oven at 50° C. for 12 hours to give the title compound as a white solid (11.05 g, 86% yield).

$^1$HNMR (CDCl$_3$, 400 MHz) δ: −0.07 (s, 3H), 0.11 (s, 3H), 0.89 (s. 9H), 2.91 (s, 3H0, 4.80-4.83 (m, 1H), 6.80 (bs, 1H). 6.98 (d, 1H), 7.12 (d, 1H), 7.36-7.44 (m, 5H), 7.52-7.54 (m, 1H) ppm.

Preparation 8: Methyl (3-{2-[((2R)-2-{4-(benzyloxy)-3-[(methylsulfonyl)amino]phenyl}-2-hydroxyethyl)amino]-2-methylpropyl}phenyl)acetate

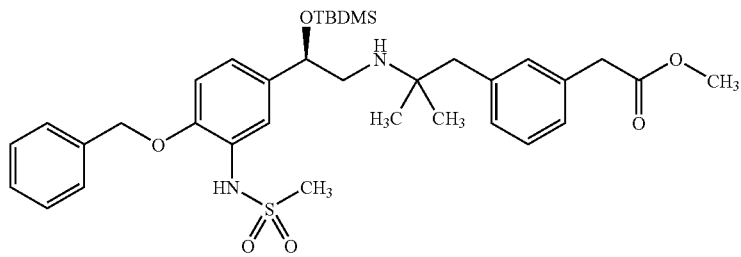

The bromide of preparation 7 (36.0 g, 70.8 mmol) and the amine of preparation 5 (36.0 g, 153 mmol) were heated at 85° C. for 72 hours. The reaction mixture was cooled to room temperature and purified by column chromatography on silica gel eluting with pentane:ethyl acetate (50:50 by volume) to yield the title product as a pale yellow oil (37.2 g).

$^1$HNMR (CDCl$_3$, 400 MHz) δ: −0.15 (s, 3H), 0.00 (s, 3H), 0.83 (s, 9H), 1.01 (s, 3H), 1.04 (s, 3H), 2.57-2.97 (m, 7H), 3.59 (s, 2H), 3.68 (s, 3H), 4.68-4.72 (m, 1H), 5.09 (s, 2H), 6.79 (bs, 1H), 6.95 (d, 1H), 7.04-7.21 (m, 7H), 7.37-7.44 (m, 5H), 7.56 (d, 1H) ppm.

MS (APCI): m/z 655 [M+H]+

Preparation 9: methyl (3-{2-[((2R)-2-{[tert-butyl(dimethyl)silyl]oxy}-2-{4-hydroxy-3-[(methylsulfonyl)amino]phenyl}ethyl)amino]-2-methylpropyl}phenyl)acetate

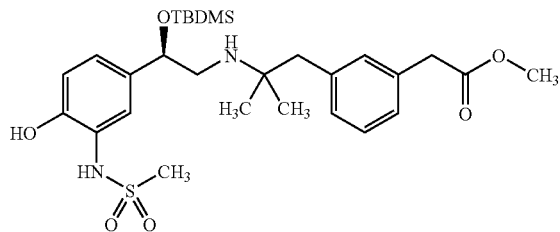

A solution of the benzyl protected alcohol of preparation 8 (36.8 g, 56 mmol) in ethanol (550 ml) was treated with ammonium formate (16.0 g, 254 mmol) and 20% palladium hydroxide on carbon (1.5 g). The resulting suspension heated to 85° C. for 2 hours. After 2 hours further 20% palladium hydroxide on carbon (1.0 g) was added and heating continued for 1 hour. The reaction mixture was cooled to room temperature, filtered and the solvent removed in vacuo. The residue was partitioned between ethyl acetate (500 ml) and 2N aqueous ammonia (100 ml). The organic phase was separated, dried (magnesium sulfate) and the solvent removed in vacuo. The residue was purified by column chromatography on silica gel eluting with dichloromethane:methanol:0.88:ammonia (95:5:0.5 by volume) to yield the title product as a pale yellow oil (20.6 g).

$^1$HNMR (400 MHz, CDCl$_3$) δ: −0.17 (s, 3H), −0.05 (s, 3H), 0.80 (s, 9H), 1.07 (s, 3H), 1.09 (s, 3H), 2.66-2.91 (m, 7H), 3.62 (d, 2H), 3.69 (s, 3H), 4.71-4.74 (m, 1H), 6.58 (d, 1H), 6.88 (dd, 1H), 7.05-7.14 (m, 3H), 7.21-7.25 (m, 1H), 7.30 (s, 1H) ppm.

MS (electrospray): m/z 565 [M+H]$^+$

Preparation 10: (3-{2-[(2R)-2-(tert-Butyl-dimethyl-silanyloxy)-2-(4-hydroxy-3-methanesulfonylamino-phenyl)-thylamino]-2-methyl-propyl}-phenyl)-acetic acid

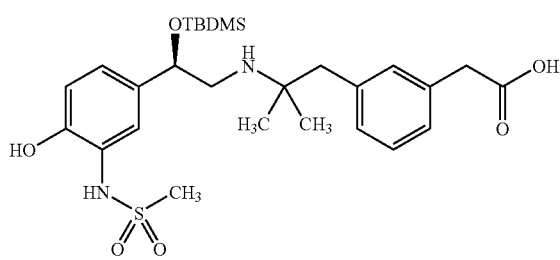

The ester of preparation 9 (20.6, 36 mmol) was dissolved in tetrahydrofuran (150 ml) and the solution treated dropwise with 1M aqueous lithium hydroxide (72 ml, 72 mmol). The reaction mixture was stirred at room temperature for 72 hours. The reaction mixture was neutralised by addition of 1M hydrochloric acid (72 ml, 72 mmol) and concentrated to low volume. The aqueous phase was decanted and the residue washed with water (2×50 ml). The residue was redicolved in tetrahydrofuran (50 ml) and toluene (50 ml) and the solvent removed in vacuo to give the title compound as a pale brown foam (20.179).

$^1$HNMR (400 MHz, CD$_3$OD): −0.14 (s, 3H), 0.07 (s, 3H), 0.83 (s, 9H), 1.32 (m, 6H), 2.93 (m, 5H), 3.23 (m, 2H), 3.54 (m, 2H), 4.94 (m, 1H), 6.91 (d, 1H), 7.03-7.16 (m, 3H), 7.26 (m, 2H), 7.60 (m, 1H) ppm.

MS (electrospray): m/z 236 [M+H]$^+$

Preparation 5a:
[3-(2-amino-2-methyl-propyl)-phenyl]-acetic acid ethyl ester

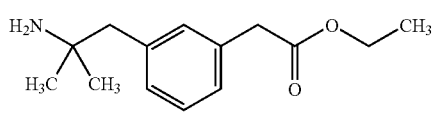

A mixture of the amide from preparation 4 (151.4 g, 534 mmol), thiourea (48.7 g, 640 mmol) and acetic acid (303 ml) in ethanol (1.5 L) was heated to reflux under a nitrogen atmosphere for 5 hours. The reaction mixture was allowed to cool to room temperature and the suspension concentrated in vacuo. The residues were azeotroped with toluene (2×900 mL) then treated with ethanol (1.5 L) and stirred for 1 hour. The solid precipitate was removed by filtration, and the filtrate cooled in an ice bath, treated with 98% sulphuric acid (227 mL) and stirred for 1 hour at ambient temperature. The solution was concentrated in vacuo to remove most of the ethanol and adjusted to pH9 using aqueous sodium bicarbonate. The solid precipitate was removed by filtration and washed with water (300 mL) then ethyl acetate (1.0 L). The layers of the combined biphasic filtrate and washes were separated and the aqueous layer re-extracted with ethyl acetate (1.0 L+500 mL). The combined ethyl acetate extracts were dried over magnesium sulphate, filtered and concentrated in vacuo to give the title compound as a brown oil (89.5 g).

$^1$H NMR (d$_6$-DMSO, 400 MHz) δ: 0.99 (s, 6H), 1.16 (t, 3H), 2.59 (s, 2H), 3.61 (s, 2H), 4.06 (q, 2H), 7.06 (m, 3H), 7.21 (m, 1H)

Preparation 5b: [3-(2-amino-2-methyl-propyl)-phenyl]-acetic acid ethyl ester, dl-p-toluoyl-L-tartrate

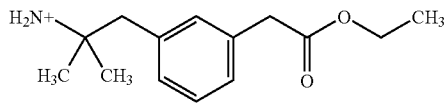

-continued

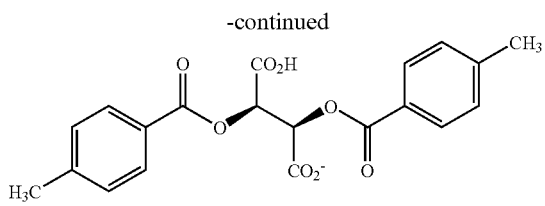

A solution of the amine from preparation 5a (124.9 g, 531 mmol) in acetonitrile (1.0 L) was treated with a solution of di-p-toluoyl-L-tartaric acid (194.8 g, 504 mmol) in acetonitrile (750 mL). The resulting slurry was stirred for 3 hours and the solid precipitate isolated by filtration and washed with acetonitrile (2×250 mL) to give the title compound as an off-white solid (210 g).

$^1$H NMR ($d_6$-DMSO, 400 MHz) δ: 1.13 (s, 6H), 1.17 (t, 3H), 2.34 (s, 6H), 2.78 (s, 2H), 3.63 (s, 2H), 4.06 (q, 2H), 5.61 (s, 2H), 7.02 (d, 2H), 7.15 (d, 1H), 7.25 (m, 5H), 7.80 (d, 4H)

Preparation 5c:
[3-(2-Amino-2-methyl-propyl)-phenyl]-acetic acid ethyl ester

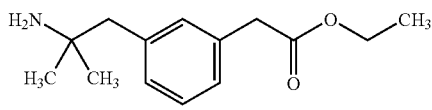

A solution of potassium carbonate (37.90 g, 274.22 mmol) in water (213 ml) was added to a suspension of preparation 5b (42.62 g, 68.56 mmol) in propionitrile (213 ml) and stirred until all solid had dissolved. The phases were then separated and the propionitrile phase washed with water (107 ml). The solution was reduced in volume under reduced pressure to approximately 30 ml to give the title compound as a propionitrile solution. A sample was removed and concentrated to dryness to obtain a weight assay and yield was shown to be 81%.

$^1$H NMR ($d_6$-DMSO, 400 MHz) δ: 0.99 (s, 6H), 1.16 (t, 3H), 2.59 (s, 2H), 3.61 (s, 2H), 4.06 (q, 2H), 7.06 (m, 3H), 7.21 (m, 1H)

Preparation 8a: Ethyl (3-{2-[((2R)-2-{[tert-butyl (dimethyl)silyl]oxy}-2-{4-benzyloxy-3-[(methylsulfonyl)amino]phenyl}ethyl)amino]-2-methylpropyl}phenyl)acetate

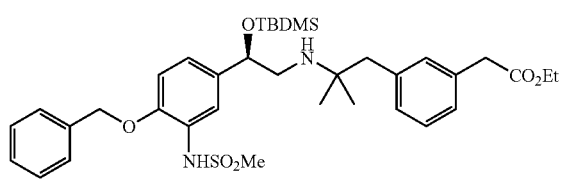

N-[2-(benzyloxy)-5-((1R)-2-bromo-1-{[tert-butyl(dimethyl)silyl]oxy}ethyl)phenyl]methanesulfonamide (14.34 g, 27.88 mmol) was added to the solution of preparation 5c (13.12 g, 55.75 mmol) in propionitrile (15 ml). The mixture was then heated at reflux for 3 days. The solution was diluted with propionitrile (55 ml) and cooled to 20-25° C. The solution was washed with 1 M HCl$_{(aq)}$ (70 ml) then water (35 ml) and the solution carried directly into the next step assuming 100% yield.

Preparation 9a: Ethyl (R)-2-(3-{2-[2-hydroxy-2-(4-benzyloxy-3-methanesulfonamidophenyl)ethylamino]-2-methylpropyl}phenyl)acetate

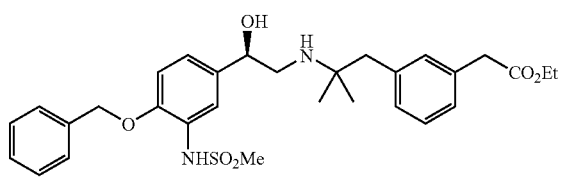

Triethylamine trihydrofluoride (9.1 ml, 8.99 g, 55.76 mmol) was added to the solution of preparation 8a (18.64 g, 27.88 mmol) in propionitrile (72 ml). The solution was stirred at 20-25° C. for 3 hours. The solution was then quenched with 5M NH$_{3(aq)}$ (72 ml) stirred for 10 minutes and the phases separated. The propionitrile solution was then washed with water (72 ml) and the solution carried directly into the next step assuming 100% yield.

Preparation 10a: (R)-2-(3-{2-[2-hydroxy-2-(4-benzyloxy-3-methanesulfonamidophenyl)ethylamino]-2-methylpropyl}phenyl)acetic acid

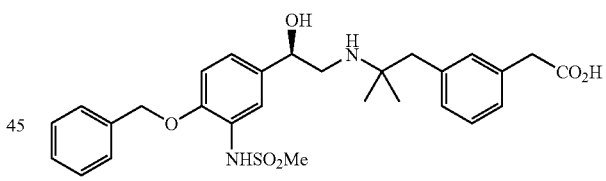

A solution of sodium hydroxide (6.69 g, 167.28 mmol) in water (72 ml) was added to the solution of preparation 9a (15.47 g, 27.88 mmol) in propionitrile (72 ml). The two phase mixture was then stirred vigorously for 3 hours. The phases were allowed to separate and the aqueous phase washed with fresh propionitrile (72 ml), then diluted with 1,4-dioxane (72 ml). The pH of the solution was then adjusted to pH 6-7 by the addition of 37% w/w HCl$_{(aq)}$ and the resulting suspension was stirred for one hour. The suspension was then filtered and washed on the filter paper with water then dried giving the title compound as an off white solid (13.55 g, 92% over 3 steps).

$^1$HNMR (400 MHz, CD$_3$OD) δ: 1.33 (s, 3H), 1.35 (s, 3H), 2.89 (s, 3H), 2.96 (s, 2H), 3.06-3.19 (m, 2H), 3.50 (s, 2H), 4.50 (m, 1H). 5.22 (s, 2H), 7.08 (d, 1H), 7.13 (d, 1H), 7.19 (s, 1H), 7.24 (t, 2H), 7.27 (d, 1H), 7.31 (d, 1H), 7.38 (t, 2H), 7.48 (d, 2H), 7.49 (s, 1H) ppm.

Preparation 10b: (R)-2-(3-{2-[2-hydroxy-2-(4-hydroxy-3-methanesulfonamidophenyl)ethylamino]-2-methylpropyl}phenyl)acetic acid sodium salt

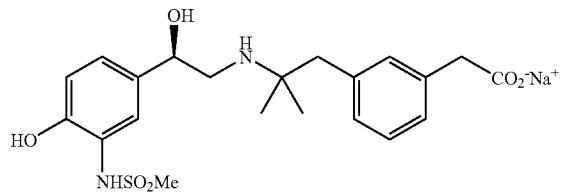

A solution of sodium hydroxide (1.40 g, 35.05 mmol) in water (100 ml) was added to a suspension of preparation 10a (18.46 g, 35.05 mmol) in methanol (600 ml). The mixture was hydrogenated over 20 wt % Palladium hydroxide on carbon at 150 psi and 60° C. for 5 hours. The mixture was filtered to remove catalyst residues and then reduced in volume at reduced pressure to 100 ml. The mixture was distilled and replaced at reduced pressure to acetonitrile at constant volume. The resulting suspension was filtered and washed on the paper with acetonitrile then dried to provide the title compound as an off white solid (15.34 g, 95%).

$^1$HNMR (400 MHz, CD$_3$OD) δ: 1.07 (s, 3H), 1.09 (s, 3H), 2.70 (s, 2H), 2.73-2.81 (m, 2H), 2.87 (s, 3H), 3.44 (s, 2H), 4.60-4.63 (m, 1H), 6.84 (d, 1H), 6.92 (d, 1H), 7.04 (d, 1H), 7.11 (s, 1H), 7.14 (d, 1H), 7.15 (t, 1H), 7.34 (s, 1H) ppm.

Said compounds of formula 10b can then be reacted with a suitable amine of formula NHR$^8$-Q$^2$-A (3)

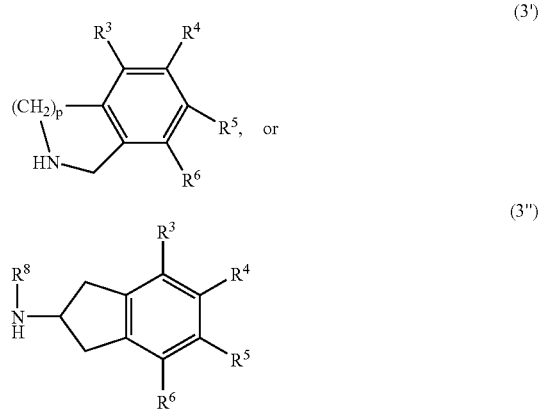

in the presence of a conventional coupling agent such as 1-(3-dimethylaminopropyl)-3-ethylcarbodiimide hydrochloride or dicyclohexylcarbodiimide in a suitable solvent such as pyridine, dimethylformamide or dimethylacetamide.

in order to obtain a compound of formula (1):

(1)

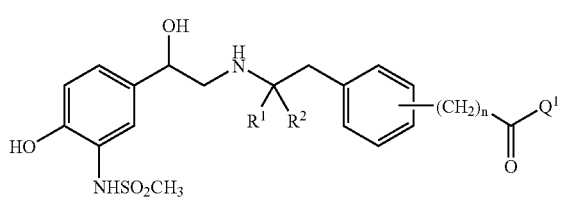

wherein R$^1$ and R$^2$ are methyl and n is 1.

Preparation 11: 1-(3-Bromophenyl)-2-methylpropan-2-ol

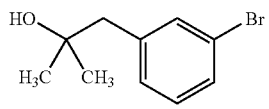

Methylmagnesium bromide (3M solution in diethylether, 51.6 ml, 155 mmol) was slowly added to a solution of 1-(3-bromo-phenyl)propan-2-one (15.0 g, 70 mmol) in dry diethylether (200 ml) at 0° C. The resulting mixture was left for 3 hours, then cooled to 0° C. and slowly quenched with saturated aqueous ammonium chloride solution. The organic phase was washed with brine, dried (sodium sulfate). The yellow oil was then purified by column chromatography on silica gel eluting with dichloromethane:pentane:methanol (90:5:5 by volume to afford a pale yellow oil (13.26 g).

$^1$H NMR (400 MHz, CDCl$_3$): δ 1.22 (s, 6H), 1.42 (bs, 1H), 2.74 (s, 2H), 7.15 (m, 2H), 7.40 (m, 2H) ppm.

Preparation 12: N-[2-(3-Bromophenyl)-1,1-dimethylethyl]-2-chloroacetamide

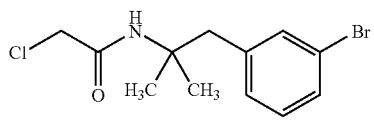

Chloroacetonitrile (6.63 ml, 105 mmol) was added to a stirred solution of the alcohol of preparation 11 (12.0 g, 52.0 mmol) in acetic acid (25 ml) at room temperature. The resulting solution was cooled to 0° C. and concentrated sulfuric acid (25 ml) was added keeping the temperature <10° C. The resulting solution was left to stir for 1 hour and then poured onto ice and basified by the addition of solid potassium carbonate. The product was extracted with ethyl acetate (2×500 ml), the organics combined and washed with water (50 ml), dried (sodium sulfate) and the solvent removed in vacuo to afford the title compound as an orange solid (16.08 g).

$^1$H NMR (400 MHz, CDCl$_3$): δ 1.37 (s, 6H), 3.02 (s, 2H), 3.94 (s, 2H), 6.17 (bs, 1H), 7.03-7.08 (d, 1H), 7.11-7.13 (t, 1H), 7.26 (s, 1H), 7.32-7.39 (d, 1H) ppm.

LRMS (electrospray) m/z 306 [M+H]$^+$

Preparation 13: [2-(3-Bromophenyl)-1,1-dimethylethyl]amine

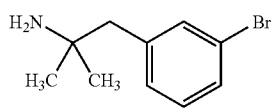

A solution of the amide from preparation 12 (32.0 g, 105 mmol), thiourea (9.60 g, 126 mmol) and acetic acid (50 ml) in ethanol (250 ml) was heated to reflux overnight. The reaction mixture was cooled to room temperature and filtered, the filtrate was concentrated in vacuo and basified using aqueous sodium hydroxide solution (1M, 450 ml). The product was extracted with dichloromethane (2×500 ml) and the combined organics washed with brine (50 ml), dried (sodium sulfate) and the solvent removed in vacuo to afford the title compound as a black oil (23 g).

$^1$H NMR (400 MHz, CDCl$_3$): δ 1.12 (s, 6H), 1.84 (bs, 2H), 2.62 (s, 2H), 7.08-7.16 (m, 2H), 7.32-7.36 (m, 2H)) pm.

LRMS (electrospray) m/z 228 [M+H]$^+$

Preparation 14: N-[2-(Benzyloxy)-5-((1R)-2-{[2-(3-bromophenyl)-1,1-dimethylethyl]amino}-1-hydroxyethyl)phenyl]methanesulfonamide

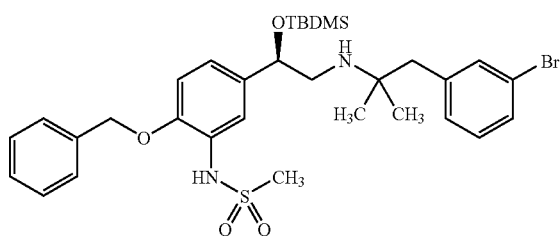

The amine of preparation 13 (5.04 g, 22.3 mmol) was dissolved in dichloromethane (20 ml) and treated with N-[2-(Benzyloxy)-5-((1S)-2-bromo-{[tert-butyl(dimethyl)silyl]oxy}ethyl)-phenyl]methanesulphonamide (WO 02/06258, pg. 36, example 14a) (11.90 g, 45.0 mmol). The resulting solution heated at 90° C. until the solvent evaporated and then stirred at 90° C. for a further 16 hours. The reaction mixture was cooled to room temperature and the residue was purified by column chromatography on silica gel eluting with pentane:ethyl acetate (90:10) to yield the title product as a brown oil (8.36 g).

$^1$HNMR (CD$_3$OD, 400 MHz) δ: −0.14 (s, 3H), 0.04 (s, 3H), 0.84 (s, 9H), 1.10 (s, 3H), 1.13 (s, 3H), 2.87 (s, 3H), 2.67-2.90 (m, 4H), 4.73-4.77 (m, 1H), 5.25 (s, 2H), 7.12-7.23 (m, 4H), 7.36-7.48 (m, 6H), 7.53-7.55 (m, 2H) ppm.

MS (electrospray): m/z 661/663 [M+H]$^+$, 683/685 [M+H]$^+$

Preparation 15: Methyl 3-{2-[((2R)-2-{4-(benzyloxy)-3-[(methylsulfonyl)amino]phenyl}-2-{[tert-butyl(dimethyl)silyl]oxy}ethyl)amino]-2-methylpropyl}benzoate

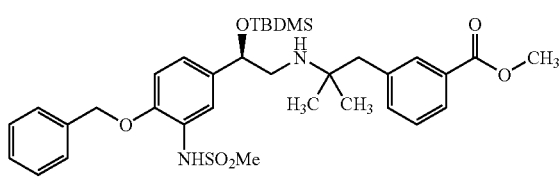

A solution of the bromide of preparation 14 (8.36 g, 12.6 mmol), (1,1'-bis(diphenylphosphino)ferrocene)dichloropalladium(II) (1.03 g, 1.26 mmol) and triethylamine (3.5 ml, 25.1 mmol) in methanol was heated at 100° C. under 100 psi carbon monoxide for 16 hours. The reaction mixture was cooled to room temperature, filtered and the solvent removed in vacuo. Purification by column chromatography on silica gel eluting with dichloromethane:methanol: 0.880 ammonia (90:10:1) gave the title compound as an orange oil, 7.79 g (trace contamination with catalyst residues).

$^1$HNMR (400 MHz, CD$_3$OD) δ: −0.17 (s, 3H), 0.00 (s, 3H), 0.80 (s, 9H), 1.12 (s, 3H), 1.15 (s, 3H), 2.67-2.92 (m, 3H), 3.96 (s, 3H), 4.73-4.77 (m, 1H), 5.24 (s, 2H), 7.11 (d, 1H), 7.19 (dd, 1H), 7.36-7.48 (m, 6H), 7.54 (d, 2H), 7.91-7.93 (m, 2H) ppm.

MS (electrospray) m/z 641 [M+H]$^+$, 663 [M+Na]$^+$

Preparation 16: Methyl 3-{2-[((2R)-2-{[tert-butyl(dimethyl)silyl]oxy}-2-{4-hydroxy-3-[(methylsulfonyl)amino]phenyl}ethyl)amino]-2-methylpropyl}benzoate

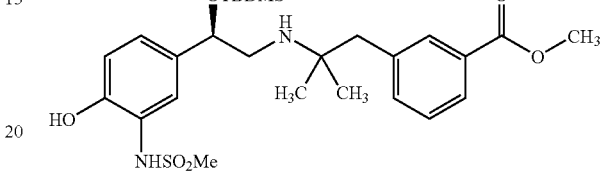

Prepared from the ester of preparation 15 using the method of preparation 7 to give the title compound as a colourless oil.

$^1$HNMR (400 MHz, CD$_3$OD) δ: −0.21 (s, 3H), −0.05 (s, 3H), 0.75 (s, 9H), 1.08 (s, 3H), 1.12 (s, 3H), 2.62-2.88 (m, 7H), 3.92 (s, 3H), 4.64-4.69 (m, 1H), 6.84 (d, 1H), 7.03 (dd, 1H), 7.35-7.36 (m, 1H), 7.39-7.42 (m, 2H), 7.87-7.89 (m, 2H) ppm.

MS (electrospray) m/z 551 [M+H]$^+$, 573 [M+Na]$^+$

Preparation 17: 3-{2-[((2R)-2-{[tert-Butyl(dimethyl)silyl]oxy}-2-{4-hydroxy-3-[(methylsulfonyl)amino]phenyl}ethyl)amino]-2-methylpropyl}benzoic acid

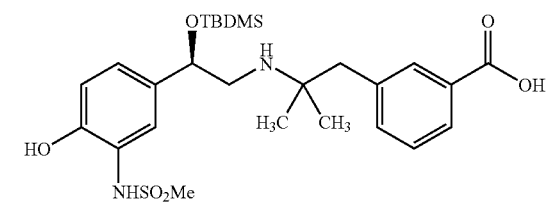

Prepared from the ester of preparation 16 to using the method of preparation 8 to give the title compound as a colourless solid.

$^1$HNMR (400 MHz, CD$_3$OD) δ: −0.14 (s, 3H), 0.04 (s, 3H), 0.82 (s, 9H), 1.23 (s, 3H), 1.24 (s, 3H), 2.88-2.96 (m, 5H), 3.00-3.14 (m, 2H), 4.83-4.87 (m, 1H), 6.89 (d, 1H), 7.07 (dd, 1H), 7.24-7.26 (m, 1H), 7.32 (t, 1H), 7.37 (s, 1H), 7.82 (s, 1H), 7.86 (d, 1H) ppm.

MS (electrospray) m/z 537 [M+H]$^+$, 559 [M+Na]$^+$

Preparation 18-53

A solution of the appropriate carboxylic acid (preparation 10 or 17) (0.15 mmol), 1-hydroxybenzotriazole hydrate (22 mg, 0.16 mmol), 1-(3-dimethylaminopropyl)-3-ethylcarbodiimide hydrochloride (34 mg, 0.18 mmol) and N-ethyldiisopropylamine (130 μL, 0.73 mmol) in N,N-dimethylformamide (2 ml) was treated with the appropriate amine (0.23 mmol) and the reaction mixture shaken at room temperature for 18 hours. The reaction mixture was concentrated in vacuo and the residue partitioned between dichloromethane (3 ml) and water (1 ml). The phases were separated and the organic layer washed with brine (1 ml), dried (sodium sulphate) and concentrated in vacuo. The residue was purified by column chromatography on silica gel eluting with dichloromethane: methanol:0.88 ammonia (98:2:0 changing to 94:6:0.5 by volume) to yield the desired product.

Alternatively, the following process can be used for the synthesis of preparations 18 to 53:

A solution of appropriate carboxylic acid from preparation 10 or 17 (5.08 mmol) in N,N-dimethylformamide (60 ml) is treated with 1-hydroxybenzotriazole hydrate (0.755 g, 5.59 mmol), the appropriate amine (5.08 mmol), 1-(3-dimethylaminopropyl)-3-ethylcarbodiimide hydrochloride (1.07 g, 5.59 mmol) and triethlyamine (1.49 ml, 10.67 mmol). The resulting suspension is left to stir at room temperature for 18 hours. The solvent is removed in vacuo and the residue partitioned between dichloromethane (100 ml) and sat. aq. sodium bicarbonate (50 ml). The organic phase is separated and the aqueous phase extracted with dichloromethane: methanol (95:5 by volume, 2×20 ml). The combined organic extracts are separated, washed with saturated aqueous sodium chloride (100 ml), dried (sodium sulfate) and the solvent removed in vacuo. The residue is purified by column chromatography on silica gel eluting with dichloromethane: methanol: 0.88 ammonia (95:5:0.5 by volume) to yield the desired compound.

Preparations 18 to 47

| No | Q¹ | Data |
|---|---|---|
| 18 | (4-hydroxy-3-methoxybenzyl)aminomethyl | ¹HNMR (CDCl₃, 400 MHz) δ: −0.19 (s, 3 H), −0.11 (s, 3 H), 0.75 (s, 9 H), 1.03 (s, 3 H), 1.05 (s, 3 H), 2.57-2.85 (m, 7 H), 3.57 (m, 2 H), 3.74 (s, 3 H), 4.31 (m, 2 H), 4.65 (m, 1 H). 6.22 (m, 1 H), 6.63 (d, 1 H), 6.67 (m, 1 H), 6.76 (m, 1 H), 6.82 (d, 1 H), 7.03 (m, 2 H), 7.12 (m, 1 H), 7.22 (m, 1 H), 7.34 (m, 1 H)<br>MS (electrospray) m/z 686 [M + H]⁺ |
| 19 | (4'-hydroxybiphenyl-4-yl)methylamino | ¹HNMR (400 MHz, CD₃OD) δ: −0.19 (s, 3 H), −0.02 (s, 3 H), 0.79 (s, 9 H), 1.02 (s, 3 H), 1.04 (s, 3 H), 2.60-2.71 (m, 3 H), 2.82-2.87 (4 H, m), 3.52 (s, 2 H), 4.36 (s, 2 H), 4.65-4.68 (m, 1 H), 6.81-6.85 (m, 3 H), 6.99-7.03 (m, 2 H), 7.10 (s, 1 H), 7.16-7.22 (m, 2 H), 7.24-7.26 (d, 2 H), 7.35 (d, 1 H), 7.40 (d, 2 H), 7.45 (d, 2 H).<br>MS (electrospray) m/z 730 [M − H]⁻, 732 [M + H]⁺ |
| 20 | (5-chloro-2-hydroxybenzyl)amino | ¹HNMR (400 MHz, CD₃OD) δ: −0.19 (s, 3 H), −0.02 (s, 3 H), 0.80 (s, 9 H), 1.02 (s, 3 H), 1.05 (s, 3 H), 2.61-2.71 (m, 3 H), 2.83-2.87 (4 H, m), 3.52 (s, 2 H), 4.29 (s, 2 H), 4.66-4.69 (m, 1 H), 6.72 (d, 1 H), 6.84 (d, 1 H), 7.00-7.05 (m, 4 H), 7.08 (s, 1 H), 7.14-7.22 (m, 2 H), 7.35 (s, 1 H)<br>MS (APCI) m/z 688 [M-H]⁻, 690 [M + H]⁺ |
| 21 | (4-hydroxy-3,5-dimethylbenzyl)amino | ¹HNMR (400 MHz, CD₃OD) δ: −0.19 (s, 3 H), −0.02 (s, 3 H), 0.79 (s, 9 H), 1.01 (s, 3 H), 1.04 (s, 3 H), 2.14 (s, 6 H), 2.60-2.70 (m, 3 H), 2.82-2.87 (4 H, m) 3.48 (s, 2 H), 4.18 (s, 2 H), 4.65-4.68 (m, 1 H), 6.77 (s, 2 H), 6.83 (d, 1 H), 6.98-7.02 (m, 2 H), 7.08 (s, 1 H), 7.14-7.21 (m, 2 H), 7.35 (s, 1 H).<br>MS (APCI) m/z 684 [M + H]⁺ |

-continued

Preparations 18 to 47

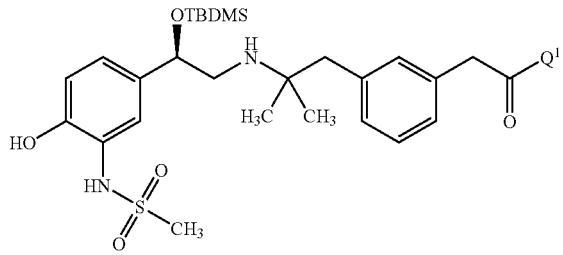

| No | Q$^1$ | Data |
|---|---|---|
| 22 | (naphthalen-1-ylmethyl with 2-OH)-NH- | $^1$HNMR (400 MHz, CD$_3$OD) δ: −0.19 (s, 3 H), −0.03 (s, 3 H), 0.79 (s, 9 H), 0.89 (s, 3 H), 0.91 (s, 3 H), 2.50-2.60 (m, 3 H), 2.76-2.81 (m, 1 H), 2.85 (s, 3 H), 3.48 (s, 2 H), 4.64 (dd, 1 H), 4.78 (s, 2 H), 6.85 (d, 1 H), 6.95-6.97 (m, 2 H), 7.01 (d, 1 H), 7.09-7.14 (m, 3 H), 7.26 (dd, 1 H), 7.35 (s, 1 H), 7.39 (dd, 1 H), 7.68 (d, 1 H), 7.72 (d, 1 H), 7.89 (d, 1 H).<br>MS (electrospray) m/z 706 [M + H]$^+$, 704 [M − H]$^−$ |
| 23 | (6-hydroxynaphthalen-2-ylmethyl)-NH- | $^1$HNMR (400 MHz, CD$_3$OD) δ: −0.19 (s, 3 H), −0.02 (s, 3 H), 0.79 (s, 9 H), 1.00 (s, 3 H), 1.02 (s, 3 H), 2.60-2.71 (m, 3 H), 2.82-2.86 (m, 1 H), 2.86 (s, 3 H), 3.54 (s, 2 H), 4.45 (s, 2 H), 4.68 (dd, 1 H), 6.85 (d, 1 H), 7.03 (m, 4 H), 7.09 (s, 1 H), 7.17-7.27 (m, 3 H), 7.35 (s, 1 H), 7.54-7.61 (m, 3 H).<br>MS (electrospray) m/z 704 [M − H]$^−$ |
| 24 | (4'-hydroxybiphenyl-3-ylmethyl)-NH- | $^1$HNMR (400 MHz, CD$_3$OD) δ: −0.19 (s, 3 H), −0.02 (s, 3 H), 0.79 (s, 9 H), 0.99 (s, 3 H), 1.02 (s, 3 H), 2.56-2.66 (m, 3 H), 2.80-2.83 (m, 1 H), 2.85 (s, 3 H), 3.53 (s, 2 H), 4.40 (s, 2 H), 4.67 (dd, 1 H), 6.81 (d, 2 H), 6.84 (d, 1 H), 7.01 (d, 2 H), 7.09 (s, 1 H), 7.13 (d, 1 H), 7.18-7.20 (m, 2 H), 7.29 (dd, 1 H), 7.33-7.40 (m, 5 H).<br>MS (electrospray) m/z 730 [M − H]$^−$, 732 [M + H]$^+$, 754 [M + Na]$^+$ |
| 25 | (3'-hydroxybiphenyl-3-ylmethyl)-NH- | $^1$HNMR (400 MHz, CD$_3$OD) δ: −0.18 (s, 3 H), −0.01 (s, 3 H), 0.80 (s, 9 H), 1.01 (s, 3 H), 1.04 (s, 3 H), 2.58-2.68 (m, 2 H), 2.86 (s, 3 H), 3.34 (s, 2 H), 3.53 (s, 2 H), 4.41 (s, 2 H), 4.66-4.69 (m, 1 H), 6.73 (dd, 1 H), 6.84 (d, 1 H), 6.94-6.97 (m, 2 H), 6.99-7.02 (m, 2 H), 7.08 (s, 1 H), 7.16-7.21 (m, 4 H), 7.31 (t, 1 H), 7.34 (d, 1 H), 7.40-7.42 (m, 2 H) ppm.<br>MS (electrospray) m/z 730 [M − H]$^−$ |
| 26 | (2-methyl-2-(4-OTBDMS-phenyl)propyl)-NH- | $^1$HNMR (400 MHz, CD$_3$OD) δ: −0.17 (s, 3 H), 0.00 (s, 3 H), 0.17 (s, 6 H), 0.80 (s, 9 H), 0.98 (s, 9 H), 1.09 (s, 3 H), 1.12 (s, 3 H), 1.21 (s, 6 H), 2.67-2.78 (m, 3 H), 2.87 (s, 3 H), 2.91-2.96 (m, 1 H), 3.36 (s, 2 H), 3.43 (s, 2 H), 4.71-4.75 (m, 1 H), 6.73 (d, 2 H), 6.86 (d, 1 H), 7.03-7.06 (m, 4 H), 7.15-7.22 (m, 3 H), 7.37 (d, 1 H).<br>MS (APCI) m/z 812 [M + H]$^+$ |
| 27 | (3,5-dichloro-4-hydroxy-substituted benzyl)-N(Et)- | $^1$HNMR (400 MHz, CD$_3$OD) δ: −0.18 (s, 3 H), −0.01 (s, 3 H), 0.80 (s, 9 H), 1.03 and 1.08 (2 s, 3 H), 1.01 and 1.07 (2 s, 3 H), 1.25-1.29 (2 t, 3 H), 2.65-2.69 (m, 2 H), 2.87 and 2.88 (2 s, 3 H), 2.92 (q, 2 H), 3.75 and 3.82 (2 s, 2 H), 4.04 (s, 2 H), 4.55 and 4.57 (2 s, 2 H), 4.68-4.71 (m, 1 H), 6.86 (dd, 1 H), 6.98 (d, 2 H), 7.03 (dd, 1 H), 7.10 (d, 1 H), 7.13-7.15 (m, 1 H), 7.20 (d, 1 H), 7.24 (dd, 1 H), 7.36 (dd, 1 H).<br>MS (electrospray) m/z 750/752 [M − H]$^−$ |

Preparations 18 to 47

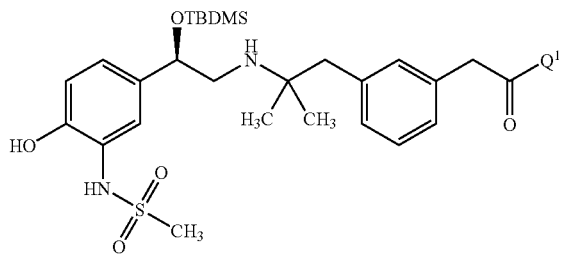

| No | Q¹ | Data |
|---|---|---|
| 28 | [structure: N-methyl-aminomethyl-naphthol] | ¹HNMR (400 MHz, CD₃OD) δ: −0.21 and −0.19 (2 s, 3 H), −0.05 and −0.03 (2 s, 3 H), 0.76 and 0.78 (2 s, 9 H), 0.96 and 0.98 (2 s, 3 H), 0.93 and 0.97 (2 s, 3 H), 2.52-2.56 (m, 2 H), 2.60-2.64 (m, 2 H), 2.86 (s, 3 H), 2.85 and 3.02 (2 s, 2 H), 3.34 (s, 3 H), 3.84 (s, 2 H), 6.84 (d, 2 H), 6.97-7.01 (m, 1 H), 7.02-7.03 (m, 1 H), 7.05 (d, 1 H), 7.11 (d, 1 H), 7.13-7.15 (m, 1 H), 7.17-7.20 (m, 1 H), 7.27-7.31 (m, 1 H), 7.35-7.36 (m, 1 H), 7.56-7.60 (m, 2 H), 7.65-7.68 (m, 1 H), 7.97 (d, 1 H). MS (electrospray) m/z 750/752 [M − H]⁻ |
| 29 | [structure: aminomethyl-biphenyl-ol] | ¹HNMR (400 MHz, CD₃OD) δ: −0.18 (s, 3 H), −0.01 (s, 3 H), 0.80 (s, 9 H), 1.02 (s, 3 H), 1.04 (s, 3 H), 2.58-2.68 (m, 2 H), 2.86 (s, 3 H), 3.34 (s, 2 H), 3.52 (s, 2 H), 4.40 (s, 2 H), 4.66-4.69 (m, 1 H), 6.84 (m, 3 H), 6.97-7.02 (m, 2 H), 7.07-7.18 (m, 6 H), 7.28 (t, 1 H), 7.34 (d, 1 H), 7.38 (s, 1 H), 7.40-7.42 (m, 1 H). MS (electrospray) m/z 730 [M − H]⁻ |
| 30 | [structure: tetrahydroisoquinolinol] | ¹HNMR (400 MHz, CD₃OD) δ: −0.18 (s, 3 H), 0.00 (s, 3 H), 0.80 (s, 9 H), 0.95-1.05 (m, 6 H), 2.50-2.90 (m, 9 H), 3.68 and 3.74 (2 t, 2 H), 3.82 (s. 2 H), 4.57 and 4.59 (2 s, 2 H), 4.62-4.69 (m, 1 H), 6.50-6.62 (m, 2 H), 6.78-7.23 (m, 7 H), 7.37-7.39 (m, 1 H). MS (APCI) m/z 680 [M − H]⁻ |
| 31 | [structure: aminobutyl-phenol] | ¹HNMR (400 MHz, CD₃OD) δ: −0.18 (s, 3 H), 0.01 (s, 3 H), 0.81 (s, 9 H), 1.07 (s, 3 H), 1.10 (s, 3 H), 1.45-1.62 (m, 6 H), 2.45-2.54 (m, 2 H), 2.62-2.76 (2 H, m), 2.86 (s, 3 H), 3.15-3.22 (m, 2 H), 3.44 (s, 2 H), 4.65-4.70 (m, 1 H), 6.62-6.65 (m, 2 H), 6.83 (d, 1 H), 6.93 (d, 1 H), 6.96-7.22 (m, 6 H), 7.36 (s, 1 H). MS (electrospray) m/z 698 [M + H]⁺, 696 [M − H]⁻ |
| 32 | [structure: aminoethyl-phenol] | ¹HNMR (400 MHz, CD₃OD) δ: −0.94 (s, 3 H), 0.00 (s, 3 H), 0.80 (s, 9 H), 1.08 (s, 3 H), 1.12 (s, 3 H), 2.62-2.77 (m, 6 H), 2.85 (s, 3 H), 3.36 (t, 2 H), 3.42 (s, 2 H), 4.64-4.70 (m, 1 H), 6.63 (d, 2 H), 6.84 (d, 1 H), 9.95 (d, 2 H), 7.00-7.06 (3 H, m), 7.09 (d, 1 H), 7.69 (t, 1 H), 7.37 (s, 1 H). MS (electrospray) m/z 668 [M − H]⁻ |
| 33 | [structure: chloro-hydroxy-benzylamine] | ¹HNMR (400 MHz, CD₃OD) δ: −0.16 (s, 3 H), 0.01 (s, 3 H), 0.82 (s, 9 H), 1.05 (s, 3 H), 1.08 (s, 3 H), 2.64-2.74 (m, 3 H), 2.85-2.90 (m, 4 H), 3.52 (s, 2 H), 4.36 (s, 2 H), 4.68-4.70 (m, 1 H), 6.65 (d, 1 H), 6.80-6.81 (m, 1 H), 6.86 (d, 1 H), 7.04 (d, 2 H), 7.10-7.12 (m, 2 H), 7.16-7.23 (m, 2 H), 7.37-7.38 (m, 1 H). MS (electrospray) m/z 688 [M − H]⁻ |

-continued

Preparations 18 to 47

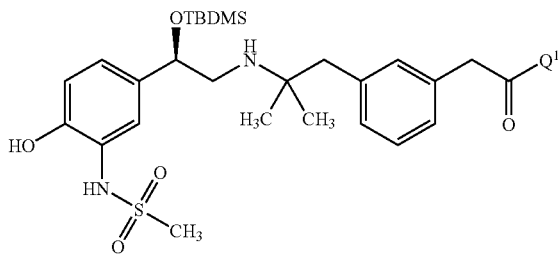

| No | Q¹ | Data |
|---|---|---|
| 34 | 4-hydroxy-3,5-dichlorobenzyl-NH- | $^1$HNMR (400 MHz, CD$_3$OD) δ: −0.16 (s, 3 H), 0.02 (s, 3 H), 0.82 (s, 9 H), 1.08 (s, 3 H), 1.11 (s, 3 H), 2.68-2.78 (m, 3 H), 2.89-2.96 (m, 4 H), 3.52 (s, 2 H), 4.21 (s, 2 H), 4.71-4.74 (m, 1 H), 6.86 (d, 1 H), 7.03-7.07 (m, 3 H), 7.11 (s, 2 H), 7.15-7.24 (m, 2 H), 7.36-7.37 (m, 1 H). MS (APCI) m/z 724/726 [M + H]$^+$, 722/724 [M − H]$^-$ |
| 35 | 4-hydroxy-2,3-dichlorobenzyl-NH- | $^1$HNMR (400 MHz, CD$_3$OD) δ: −0.16 (s, 3 H), 0.01 (s, 3 H), 0.82 (s, 9 H), 1.09 (s, 3 H), 1.11 (s, 3 H), 2.68-2.78 (m, 3 H), 2.89-2.96 (m, 4 H), 3.53 (s, 2 H), 4.21 (s, 2 H), 4.71-4.74 (m, 1 H), 6.79 (d, 1 H), 6.84-6.87 (m, 2 H), 7.04-7.11 (m, 3 H), 7.17-7.25 (m, 2 H), 7.39 (s, 1 H). MS (APCI) m/z 724/726 [M + H]$^+$, 722/724 [M − H]$^-$ |
| 36 | (4-hydroxynaphth-1-yl)methyl-NH- | $^1$HNMR (400 MHz, CD$_3$OD) δ: −0.20 (s, 3 H), −0.04 (s, 3 H), 0.78 (s, 9 H), 0.93 (s, 3 H), 0.95 (s, 3 H), 2.54-2.63 (m, 4 H), 2.84 (s, 3 H), 3.46 (s, 2 H), 4.63-4.67 (m, 3 H), 6.72 (d, 1 H), 6.84 (d, 1 H), 6.95-7.02 (m, 2 H), 7.10-7.14 (m, 2 H), 7.20 (d, 1 H), 7.35-7.39 (m, 4 H), 7.82-7.85 (m, 1 H), 7.92 (s, 1 H), 8.20-8.22 (m, 1 H). MS (APCI) m/z 706 [M + H]$^+$, 728 [M + Na]$^+$, 704 [M − H]$^-$ |
| 37 | 3-hydroxy-5-trifluoromethylbenzyl-NH- | $^1$HNMR (400 MHz, CD$_3$OD) δ: −0.19 (s, 3 H), −0.02 (s, 3 H), 0.80 (s, 9 H), 1.03 (s, 3 H), 1.06 (s, 3 H), 2.63-2.73 (m, 2 H), 2.86 (s, 3 H), 3.34 (s, 2 H), 3.53 (s, 2 H), 4.34 (s, 2 H), 4.66-4.69 (m, 1 H), 6.84 (d, 1 H), 6.87-6.90 (m, 2 H), 6.96 (s, 1 H), 7.01-7.04 (m, 2 H), 7.09 (s, 1 H), 7.15-7.22 (m, 2 H). 7.35 (d, 1 H) ppm. MS (APCI) m/z 724 [M + H]$^+$, 746 [M + Na]$^+$ |
| 38 | 3-hydroxy-5-chloro-N-ethylbenzyl-N- | $^1$HNMR (400 MHz, CD$_3$OD) δ: −0.19 and −0.18 (2 s, 3 H), −0.02 and −0.01 (2 s, 3 H), 0.80 (s, 9 H), 1.03-1.07 (m, 6 H), 1.09 (t, 3 H), 2.64-2.71 (m, 2 H), 2.87 (s, 3 H), 3.37 (q, 2 H), 3.61 and 3.69 (2 s, 2 H), 3.80 and 3.82 (2 s, 2 H), 4.50 and 4.53 (2 s, 1 H), 4.67-4.71 (m, 1 H), 6.46-6.51 (m, 1 H), 6.62-6.67 (m, 1 H), 6.69-6.74 (m, 1 H), 6.84 (dd, 1 H), 6.97-7.25 (m, 5 H), 7.35 (d, 1 H) ppm. MS (APCI) m/z 718/720 [M + H]$^+$ |
| 39 | 4-hydroxy-3-chloro-N-methylbenzyl-N- | $^1$H NMR (400 MHz, CDCl$_3$) δ: (rotamers) −0.21 and −0.18 (2 s, 3 H), −0.02 and −0.01 (2 s, 3 H), 0.76 (s, 9 H), 1.24 (s, 6 H), 2.88 (m, 3 H), 2.94 and 2.95 (2 s, 3 H), 2.98 (m, 4 H), 3.69 and 3.76 (2 s, 2 H), 4.53 (s, 2 H), 4.62-4.70 (m, 1 H), 6.60-7.23 (m, 10 H). LRMS (electrospray): m/z [M + H]$^+$ 704, [M + Na]$^+$ 726. |

-continued

Preparations 18 to 47

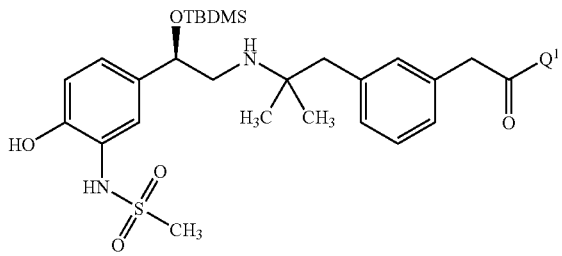

| No | Q¹ | Data |
|---|---|---|
| 40 | (3-hydroxy-5-trifluoromethylbenzyl)methylamino- | $^1$H NMR (400 MHz, CD$_3$OD) δ: (rotamers) −0.18 and −0.19 (2 s, 3 H), −0.03 and −0.02 (2 s, 3 H), 0.79 (s, 9 H), 1.00-1.05 (m, 6 H), 2.61-2.66 (m, 2 H), 2.87 (s, 3 H), 2.92 and 2.97 (2 s, 3 H), 3.77 and 3.82 (2 s, 2 H), 4.58 and 4.65 (2 s, 2 H), 4.66-4.69 (m, 1 H), 4.80 (s, 2 H), 6.71 (d, 1 H), 6.84 (d, 1 H), 6.91 (s, 2 H), 6.96-7.03 (m, 2 H), 7.05 (s, 1 H), 7.12 (d, 1 H), 7.19-7.24 (m, 1 H), 7.35 (s, 1 H) ppm.<br>LRMS (electrospray): m/z 738 [M − H]$^+$ |
| 41 | (2'-hydroxybiphenyl-2-ylmethyl)amino- | $^1$H NMR (400 MHz, CD$_3$OD): δ −0.13 (s, 3 H), 0.04 (s, 3 H), 0.85 (s, 9 H), 1.10 (s, 3 H), 1.12 (s, 3 H), 2.69-2.78 (m, 3 H), 2.89-2.94 (m, 4 H), 3.50 (s, 2 H), 4.28-4.29 (m, 2 H), 4.71-4.74 (m, 1 H), 6.87-6.92 (m, 3 H), 7.04-7.09 (m, 3 H), 7.10 (s, 1 H), 7.13-7.26 (m, 4 H), 7.27-7.32 (m, 3 H), 7.39 (d, 1 H) ppm.<br>LRMS (electrospray): m/z [M + H]$^+$ 733, [M − H]$^−$ 731. |
| 42 | (3'-hydroxybiphenyl-2-ylmethyl)amino- | $^1$H NMR (400 MHz, CD$_3$OD): δ −0.12 (s, 3 H), 0.05 (s, 3 H), 0.85 (s, 9 H), 1.15 (s, 3 H), 1.17 (s, 3 H), 2.74-2.84 (m, 3 H), 2.92 (s, 3 H), 2.95-3.02 (m, 1 H), 3.53 (s, 2 H), 4.34 (s, 2 H), 4.75-4.79 (m, 1 H), 6.74-6.81 (m, 3 H), 6.90 (d, 1 H), 7.06-7.10 (m, 2 H), 7.14 (s, 1 H), 7.16-7.32 (m, 7 H), 7.40 (d, 1 H) ppm.<br>LRMS (APCI): m/z [M + H]$^+$ 733, [M − H]$^−$ 731. |
| 43 | (4-hydroxy-2,6-dimethylbenzyl)amino- | $^1$H NMR (400 MHz, CD$_3$OD): δ −0.19 (s, 3 H), −0.02 (s, 3 H), 0.79 (s, 9 H), 1.01 (s, 3 H), 1.04 (s, 3 H), 2.14 (s, 6 H), 2.60-2.70 (m, 3 H), 2.85 (s, 3 H), 2.82-2.87 (m, 1 H), 3.48 (s, 2 H), 4.18 (s, 2 H), 4.65-4.68 (m, 1 H), 6.77 (s, 2 H), 6.83 (d, 1 H), 6.98-7.02 (m, 2 H), 7.08 (s, 1 H), 7.14-7.21 (m, 2 H), 7.35 (d, 1 H) ppm.<br>LRMS (APCI): m/z [M + H]$^+$ 684 |
| 44 | 7-hydroxy-1,2,3,4-tetrahydroisoquinolin-2-yl- | $^1$HNMR (400 MHz, CDCl$_3$) δ: −0.81 (s, 3 H), 0.00 (d, 3 H), 0.81 (s, 9 H), 0.95-1.05 (m, 6 H), 2.50-2.90 (m, 9 H), 3.60-3.82 (m, 4 H), 4.48-4.70 (m, 3 H), 6.40-6.60 (m, 2 H), 6.80-7.41 (m, 8 H) ppm.<br>MS (electrospray) m/z 682 [M + H]$^+$, 704 [M + Na]$^+$ |
| 45 | 5-hydroxy-1,2,3,4-tetrahydroisoquinolin-2-yl- | $^1$HNMR (400 MHz, DMSO$_{d6}$) δ: −0.90 (m, 3 H), 0.05 (m, 3 H), 0.8 (m, 9 H), 1.21-1.29 (m, 6 H), 2.60-2.75 (m, 2 H), 2.92 (s, 3 H), 2.98 (m, 2 H), 3.30 (m, 2 H), 3.71-4.00 (m, 4 H), 4.61-4.81 (m, 2 H), 4.89-4.91 (m, 1 H), 6.51-6.62 (m, 2 H), 6.92-7.49 (m, 8 H), 7.72-7.80 (m, 1 H) ppm.<br>MS (electrospray) m/z 60 [M − H]$^−$ |

Preparations 18 to 47

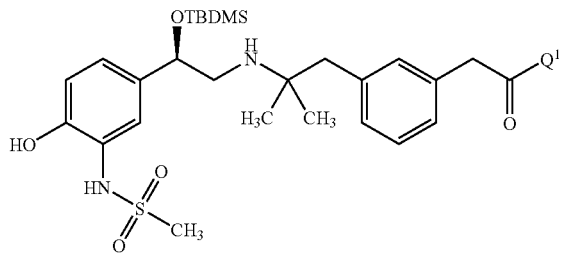

| No | Q¹ | Data |
|---|---|---|
| 46 | (structure: -NH-CH(Ph)-CH₂OH) | ¹HNMR (400 MHz, CDCl₃) δ: −0.16 (s, 3 H), −0.05 (s, 3 H), 0.80 (s, 9 H), 1.10 (s, 3 H), 1.18 (s, 3 H), 2.63 (d, 1 H), 2.78 (m, 2 H), 2.83 (m, 4 H), 3.60 (d, 1 H), 3.62 (d, 1 H), 3.80 (m, 2 H), 4.70 (m, 1 H), 5.08 (m, 1 H), 6.60 (m, 2 H), 6.81 (d, 1 H), 7.08 (m, 2 H), 7.20 (m, 7 H) ppm. MS (APCi) m/z 668 [M − H]⁻ |
| 47 | (structure: -NH-CH(Ph)-CH₂OH) | ¹HNMR (400 MHz, CDCl₃) δ: −0.18 (s, 3 H), −0.10 (s, 3 H), 0.78 (s, 9 H), 1.10 (s, 3 H), 1.18 (s, 3 H), 2.63 (d, 1 H), 2.80 (m, 6 H), 3.60 (d, 1 H), 3.78 (m, 3 H), 4.75 (m, 1 H), 5.10 (m, 1 H), 6.38 (d, 1 H), 5.78 (d, 2 H), 7.05 (m, 1 H), 7.20 (m, 8 H) ppm. MS (APCi) m/z 670 [M + H]⁺ |

Preparations 48–53

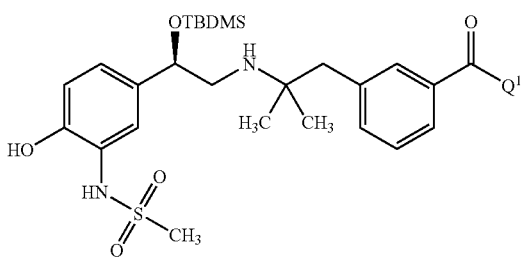

| No | Q¹ | Data |
|---|---|---|
| 48 | (biphenyl-CH₂NH– structure, OH) | ¹HNMR (400 MHz, CD₃OD) δ: −0.16 (s, 3 H), 0.00 (s, 3 H), 0.82 (s, 9 H), 1.13 (s, 3 H), 1.17 (s, 3 H), 2.68-2.93 (m, 7 H), 4.64 (s, 2 H), 4.69-4.74 (m, 1 H), 6.80-6.87 (m, 2 H), 7.05 (dd, 1 H), 7.30-7.47 (m, 7 H), 7.54 (d, 2 H), 7.75-7.78 (m, 3 H) ppm. MS (electrospray) m/z 718 [M + H]⁺ |
| 49 | (structure with H₃C, CH₃ gem-dimethyl, OTBDMS) | ¹HNMR (400 MHz, CD₃OD) δ: −0.15 (s, 3 H), −0.01 (s, 3 H), 0.22 (s, 6 H), 0.83 (s, 9 H), 1.02 (s, 9 H), 1.11 (s, 3 H), 1.13 (s, 3 H 0, 1.41 (s, 6 H), 2.67-2.92 (m, 7 H), 3.59 (s, 2 H), 4.70-4.73 (m, 1 H), 6.83-6.90 (m, 3 H), 7.07 (dd, 1 H), 7.32-7.40 (m, 5 H), 7.55-7.58 (m, 2 H) ppm. MS (electrospray) m/z 799 [M + H]⁺ |

-continued

Preparations 48-53

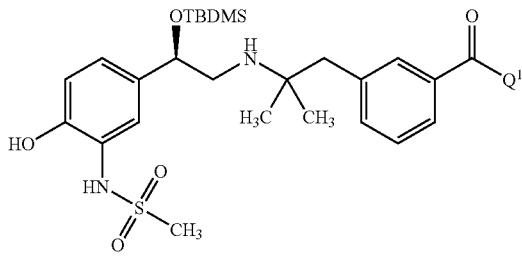

| 50 | 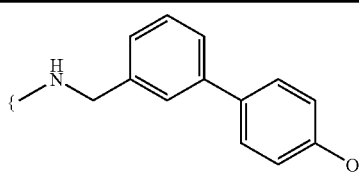 | ¹HNMR (400 MHz, CD₃OD) δ: −0.19 (s, 3 H), −0.03 (s, 3 H), 0.79 (s, 9 H), 2.67-2.92 (m, 7 H), 4.68-4.71 (m, 3 H), 6.86-6.88 (m, 3 H), 7.04 (d, 1 H), 7.31-7.33 (m, 1 H), 7.37-7.49 (m, 7 H), 7.61 (m, 1 H), 7.76-7.80 (m, 2 H) ppm. MS (electrospray) m/z 718 [M + H]⁺, 740 [M + H]⁺ |
|---|---|---|
| 51 | 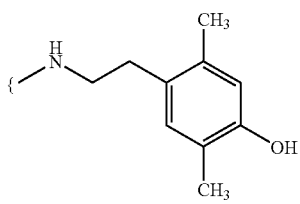 | ¹HNMR (400 MHz, CD₃OD) δ: −0.27 (s, 3 H), −0.10 (s, 3 H), 0.71 (s, 9 H), 0.99 (s, 3 H), 1.02 (s, 3 H), 2.02 (s, 3 H), 2.17 (s, 3 H), 2.56-2.81 (m, 9 H), 3.39-3.43 (m, 2 H), 4.59-4.63 (m, 1 H), 6.48 (s, 1 H), 6.77-6.79 (m, 2 H), 6.95-6.97 (m, 1 H), 7.22-7.29 (m, 3 H), 7.55-7.59 (m, 2 H) ppm. MS (electrospray) m/z 685 [M + H]⁺ |
| 52 | 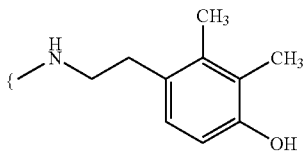 | ¹HNMR (400 MHz, CD₃OD) δ: −0.18 (s, 3 H), −0.01 (s, 3 H), 0.80 (s, 9 H), 1.09 (s, 3 H), 1.12 (s, 3 H), 2.14 (s, 3 H), 2.28 (s, 3 H), 2.65-2.92 (m, 9 H), 3.47-3.51 (m, 2 H), 4.68-4.71 (m, 1 H), 6.55 (d, 1 H), 6.83-6.87 (m, 2 H), 7.03-7.06 (m, 1 H), 7.32-7.38 (m, 3 H), 7.64-7.68 (m, 2 H) ppm. MS (electrospray) m/z 685 [M + H]⁺ |
| 53 | 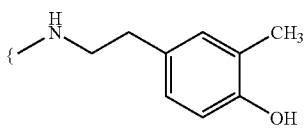 | ¹HNMR (400 MHz, CD₃OD) δ: −0.27 (s, 3 H), −0.07 (s, 3 H), 0.75 (s, 9 H), 1.03 (s, 3 H), 1.06 (s, 3 H), 2.11 (s, 3 H), 2.60-2.85 (m, 9 H), 3.47-3.51 (m, 2 H), 4.63-4.66 (m, 1 H), 6.62 (d, 1 H), 6.80-6.86 (m, 2 H), 6.92 (m, 1 H), 6.98-7.01 (m, 1 H), 7.26-7.33 (m, 3 H), 7.57-7.61 (m, 2 H) ppm. MS (electrospray) m/z 671 [M + H]⁺ |

Preparation 54: N-(4-bromobenzyl)-2-(3-{2-[((2R)-2-{[tert-butyl(dimethyl) silyl]oxy}-2-{4-hydroxy-3-[(methylsulfonyl)amino]phenyl}ethyl)amino]-2-methylpropyl}phenyl)acetamide

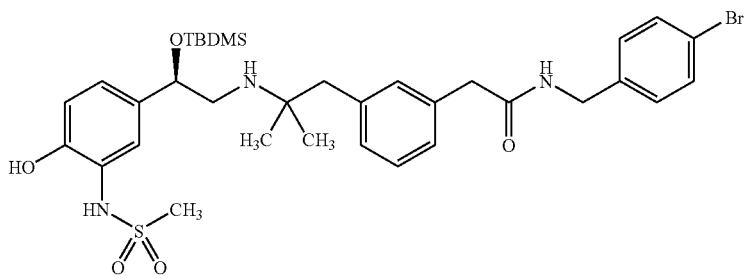

Prepared using the procedure for preparation 18 using the acid from preparation 10 and (4-bromobenzyl)amine to give the title compound as a yellow gum.

¹HNMR (400 MHz, CDCl₃): δ −0.18 (s, 3H), 0.00 (s, 3H), 0.81 (s, 9H), 1.02 (s, 3H), 1.04 (s, 3H), 2.61-2.72 (m. 4H), 2.83 (s, 3H), 3.53 (s, 2H), 4.33 (s, 2H), 4.65-4.70 (m, 1H), 6.83-6.86 (d, 1H), 7.00-7.44 (m, 10H) ppm.

MS (electrospray) m/z 720 [M+H]⁺, 742 [M+H]⁺

Preparation 55: 2-(3-{2-[((2R)-2-{[tert-butyl(dimethyl)silyl]oxy}-2-{4-hydroxy-3-[(methylsulfonyl)amino]phenyl}ethyl)amino]-2-methyl propyl}phenyl)-N-[(3'-hydroxybiphenyl-4-yl)methyl]acetamide

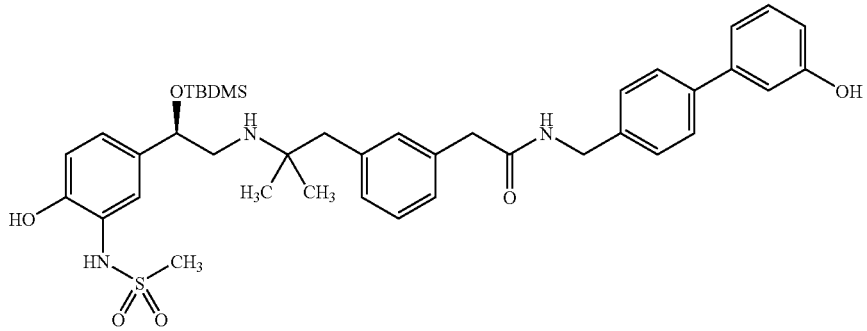

A solution of the bromide from preparation 56 (0.50 g, 0.70 mmol), (3-hydroxyphenyl)boronic acid (0.19 g, 1.4 mmol), (1,1'-bis(diphenylphosphino) ferrocene)dichloropalladium (II) (36 mg, 0.04 mmol) in N,N-dimethylformamide (8 ml) was treated with 2M aqueous sodium carbonate (2 ml) and the resulting suspension heated to 80° C. for 16 hours. The reaction mixture was cooled to room temperature and the solvent removed in vacuo. The residue was azeotroped with toluene (50 ml), redissolved in ethyl acetate (50 ml) and neutralised with 1N aqueous hydrochloric acid (to pH7). The organic layer was separated and the aqueous extracted with further ethyl acetate (2×50 ml). The combined organic extracts were washed with water (100 ml), saturated aqueous sodium chloride (100 ml), dried (sodium sulfate) and the solvent removed in vacuo to give an orange gum (515 mg) which was used without further purification.

¹HNMR (400 MHz, CD₃OD): δ −0.13 (s, 3H), 0.04 (s, 3H), 0.84 (s, 9H), 1.11 (s, 3H), 1.13 (s, 3H), 2.74-2.97 (m, 7H), 3.55-3.63 (m, 2H), 4.42-4.45 (m, 2H), 4.73-4.76 (m, 1H), 6.89-6.94 (m, 3H), 7.15-7.30 (m, 9H), 7.41 (d, 1H), 7.51 (s, 1H), 7.53 (s, 1H) ppm.

MS (electrospray) m/z 732 [M+H]⁺, 754 [M+H]⁺

Preparation 56: 2-(3-{2-[((2R)-2-{[tert-butyl(dimethyl)silyl]oxy}-2-{4-hydroxy-3-[(methylsulfonyl)amino]phenyl}ethyl)amino]-2-methyl propyl}phenyl)-N-[(2'-hydroxybiphenyl-4-yl)methyl]acetamide

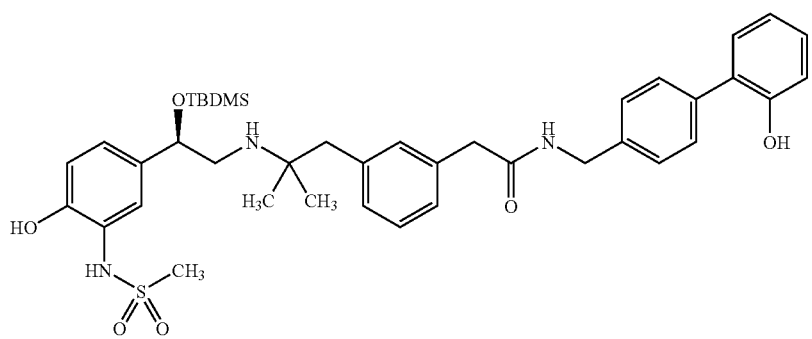

Prepared from (2-hydroxyphenyl)boronic acid using the method of preparation 55 to give the title compound as a brown oil.

¹HNMR (400 MHz, CD₃OD): δ −0.13 (s, 3H), 0.04 (s, 3H), 0.84 (s, 9H), 1.12 (s, 3H), 1.14 (s, 3H), 2.72-2.99 (m, 7H), 3.58-3.61 (m, 2H), 4.43-4.45 (m, 2H), 4.74-4.78 (m, 1H), 6.78-6.81 (m, 1H), 6.90-6.92 (m, 1H), 7.02-7.10 (m, 2H), 7.15-7.39 (m, 8H), 7.41 (d, 1H), 7.53 (s, 1H), 7.55 (s, 1H) ppm.

MS (electrospray) m/z 755 [M+H]⁺

Preparation 57: 2-Hydroxy-1-naphthamide

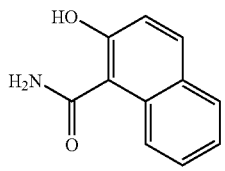

A solution of 2-hydroxy-1-napthoic acid (5.0 g, 26.6 mmol), 1-(3-dimethylaminopropyl)-3-ethylcarbodiimide hydrochloride (5.6 g, 29.2 mmol), and 1-hydroxybenzotriazole (3.95 g, 29.2 mmol) in tetrahydrofuran (70 ml) was stirred at room temperature for 30 minutes prior to the addition of 0.880 NH₃ (6 ml). The resulting suspension was stirred at room temperature for 2 hours. The reaction mixture was filtered and the filtrate diluted with water (80 ml) and extracted with ethyl acetate (4×80 ml). The combined organic extracts were washed with water (50 ml×2), saturated aqueous sodium chloride (50ml), dried (sodium sulfate) and the solvent removed in vacuo to give an orange oil. Purification by column chromatography on silica gel eluting with dichloromethane:methanol:0.880 ammonia 95:5:0.5 gave the title compound as a pink solid (1.83 g).

¹HNMR (400 MHz, CDCl₃): δ6.11-6.35 (bs, 2H), 7.17 (d, 1H), 7.36 (dd, 1H), 7.54 (dd, 1H), 7.79 (d, 1H), 7.84 (d, 1H), 8.22 (d, 1H), 11.70-11.88 (bs, 1H) ppm.

MS (electrospray) m/z 186 [M−H]⁻

Preparation 58: 6-Hydroxy-2-naphthamide

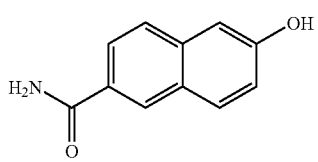

A solution of 6-hydroxy-2-napthoic acid (1.88 g, 9.99 mmol), 1-(3-dimethylaminopropyl)-3-ethylcarbodiimide hydrochloride (2.11 g, 10.98 mmol), 1-hydroxybenzotriazole (1.48 g, 10.98 mmol) and ammonium carbonate (4.80 g, 49.95 mmol) in N,N-dimethylformamide (70 ml) was left to stir at room temperature under a nitrogen atmosphere for 3 days. The solvent was removed in vacuo and the residue partitioned between saturated aqueous sodium hydrogen carbonate (50 ml) and ethyl acetate (6 ×50 ml). The combined organic extracts were washed with water (25 ml), saturated aqueous sodium chloride (25 ml), dried (sodium sulfate) and the solvent removed in vacuo. The solid was absorbed onto silica gel and purified by column chromatography on silica gel eluting with dichloromethane:methanol:0.880 ammonia (95:5:0.5 changing to 90:10:1) to give the title compound as a pale yellow solid (1.1 g).

¹HNMR (400 MHz, CD₃OD) δ: 7.14 (d, 1H), 7.15 (s, 1H), 7.79 (d, 1H), 7.83 (d, 2H), 8.32 (s, 1H) ppm.

MS (electrospray) m/z 186 [M−H]⁻

Preparation 59: 1-(Aminomethyl)-2-naphthol

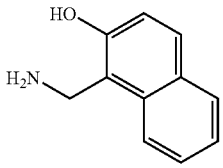

A solution of borane in tetrahydrofuran (19.23 ml of a 1M solution, 19.23 mmol) was added dropwise to a solution of the amide from preparation 57 (0.90 g, 4.81 mmol) in tetrahydrofuran (10 ml) under a nitrogen atmosphere. The reaction was then heated to reflux for 2 hours. The solution was cooled, treated with 6M hydrochloric acid (10 ml) and refluxed for a further 2 hours. The resulting suspension was cooled and the pH adjusted to pH9 by addition of 0.880 NH₃ and extracted with ethyl acetate (50 ml×3). The combined organic extracts were washed with sat. aq. sodium chloride (20 ml), dried (sodium sulfate) and the solvent removed under reduced pressure. Purification by column chromatography on silica gel eluting with dichloromethane:methanol:0.880:ammonia (95:5:0.5 changing to 90:10:1) gave the title compound as a pink solid (0.19 g).

¹HNMR (400 MHz, CD₃OD) δ: 4.41 (s, 2H), 7.07 (d, 1H), 7.23 (1H, dd), 7.43 (dd, 1H), 7.66 (d, 1H), 7.72 (d, 1H), 7.87 (d, 1H) ppm.

MS (electrospray) m/z 174 [M+H]⁺, 172 [M−H]⁻

Preparation 60: 6-(Aminomethyl)-2-naphthol

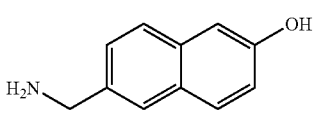

Prepared according to the method for preparation 59 using the amide from preparation 58.

¹HNMR (400 MHz, CD₃OD) δ: 3.91 (s, 2H), 7.03-7.08 (m, 2H), 7.36 (dd, 1H), 7.61 (d, 1H), 7.66 (d, 1H), 7.69 (s, 1H) ppm.

MS (electrospray) m/z 172 [M−H]⁻

Preparation 61: tert-Butyl (3-iodobenzyl)carbamate

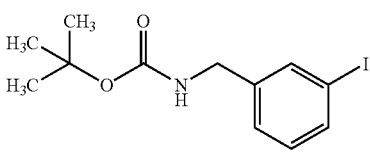

A suspension of 3-iodobenzylamine hydrochloride (4.95 g, 18.4 mmol) in dichloromethane (100 ml) was treated with triethylamine (3.1 ml, 22 mmol) and di-t-butyl dicarbonate (4.40 g, 20 mmol) and the resulting solution left to stir at room temperature under a nitrogen atmosphere for 1.5 hours. The reaction mixture was washed with 2M hydrochloric acid (30 ml), water (30 ml), dried (sodium sulfate), and the solvent removed in vacuo to give the title compound as a colourless solid (6.43 g).

$^1$HNMR (400 MHz, CDCl$_3$) δ: 1.46 (s, 9H), 4.21-4.30 (m, 2H). 4.79-4.89 (bs, 1H), 7.06 (dd, 1H), 7.25 (d, 1H), 7.60 (d, 1H), 7.63 (s, 1H) ppm.

MS (electrospray) m/z 332 [M−H]$^-$, 356 [M+Na]$^+$

Preparation 62: tert-Butyl (2-bromobenzyl)carbamate

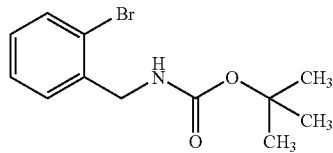

Prepared from 2-bromobenzylamine using the method of preparation 61 to give the title compound as a colourless solid.

$^1$HNMR (400 MHz, CD$_3$OD) δ: 1.50 (s, 9H), 4.33 (s, 2H), 7.18-7.22 (m, 1H), 7.35-7.38 (m, 2H). 7.59 (d, 1H) ppm.

MS (electrospray) m/z 308/310 [M+Na]$^+$

Preparation 63: tert-Butyl [(4'-hydroxybiphenyl-3-yl)methyl]carbamate

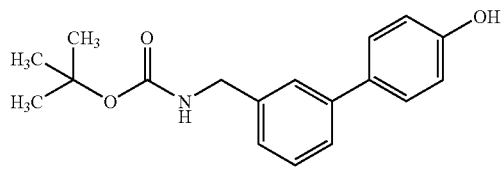

A solution of the iodide from preparation 61 (0.75 g, 2.25 mmol), 4-hydroxy phenylboronic acid (0.629, 4.50 mmol), 1,1'-bis(diphenylphosphino)ferrocenyl palladium(II) chloride (0.11 g, 0.14 mmol), in N,N-dimethylformamide (14 ml) was treated with 2M aqueous sodium carbonate (4 ml) and the resulting mixture heated at 80° C. under a nitrogen atmosphere for 16 hours. The solvent was removed in vacuo and the residue purified by column chromatography on silica gel eluting with ethyl acetate:pentane (1:3) to give the title compound as a pale pink crystalline solid (0.73 g).

$^1$HNMR (400 MHz, CDCl$_3$) δ: 1.47 (s, 9H), 4.33-4.41 (m, 2H), 4.87-4.94 (bs, 1H), 6.89 (d, 2H), 7.21 (d, 1H), 7.37 (dd, 1H), 7.43-7.45 (m, 4H) ppm.

MS (electrospray) m/z 298 [M−H]$^-$, 322 [M+Na]$^+$

Preparation 64: tert-Butyl [(2'-hydroxybiphenyl-3-yl)methyl]carbamate

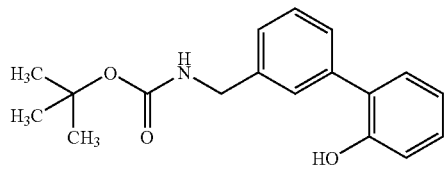

Prepared from the iodide of preparation 61 and 2-hydroxyboronic acid using the method of preparation 63 to give the title compound as a colourless solid.

$^1$HNMR (400 MHz, CDCl$_3$) δ: 1.46 (s, 9H), 4.38 (d, 2H), 4.90 (bs, 1H), 5.24 (bs, 1H), 6.97-7.01 (m, 2H), 7.22-7.47 (m, 6H) ppm.

MS (electrospray) m/z 322 [M+Na]$^+$

Preparation 65: tert-Butyl [(2'-hydroxybiphenyl-2-yl)methyl]carbamate

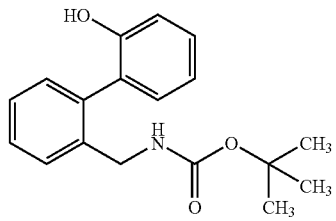

Prepared from the bromide of preparation 62 and 2-hydroxyboronic acid using the method of preparation 63 to give the title compound as a colourless solid.

$^1$HNMR (400 MHz, CD$_3$OD) δ: 1.46 (s, 9H), 4.15 (d, 2H), 6.91-6.96 (m, 2H), 7.10 (dd, 1H), 7.17-7.41 (m, 5H) ppm.

MS (electrospray) m/z 298 [M−H]$^-$

Preparation 66: tert-Butyl [(3'-hydroxybiphenyl-2-yl)methyl]carbamate

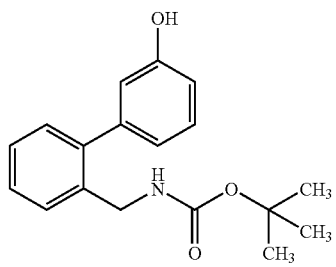

Prepared from the bromide of preparation 62 and 3-hydroxyboronic acid using the method of preparation 63 to give the title compound as a colourless solid.

$^1$HNMR (400 MHz, CD$_3$OD) δ: 1.48 (s, 9H), 4.21 (s, 2H), 6.76-6.83 (m, 3H), 7.21-7.43 (m, 5H) ppm.

MS (electrospray) m/z 298 [M−H]$^-$

Preparation 67: tert-Butyl [(3'-hydroxybiphenyl-3-yl)methyl]carbamate

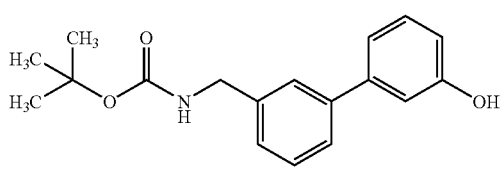

Prepared from the iodide of preparation 61 and 3-hydroxy phenylboronic acid using the method of preparation 63 to give the title compound as a brown gum.

¹HNMR (400 MHz, CDCl₃) δ: 1.48 (s, 9H), 4.37 (d, 2H), 4.86-4.91 (bs, 1H), 6.82 (dd, 1H), 7.04 (t, 1H), 7.11 (d, 1H), 7.24-7.30 (m, 2H), 7.36 (t, 1H), 7.43 (d, 1H), 7.45 (d, 1H) ppm.
MS (electrospray) m/z 298 [M−H]⁻, 597 [2M−H]⁻

Preparation 68: 3'-(Aminomethyl)biphenyl-4-ol

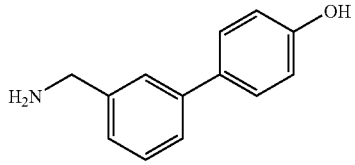

The phenol from preparation 63 (0.73 g, 2.43 mmol) was treated with 4M HCl in dioxan (6 ml, 24.3 mmol) and the resulting solution allowed to stir at room temperature for 3 hours. The solvent was removed in vacuo to give the title compound as a colourless solid.
¹HNMR (400 MHz, CD₃OD) δ: 4.17 (s, 2H), 6.87 (d, 2H), 7.34 (d, 1H), 7.45-7.50 (m, 3H), 7.61 (d, 1H), 7.65 (s, 1H) ppm.
MS (electrospray) m/z 198 [M−H]⁻, 200 [M+H]⁺

Preparation 69: 3'-(Aminomethyl)biphenyl-3-ol

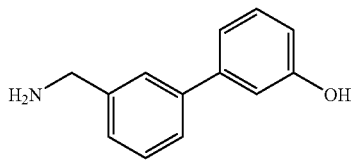

Prepared from the phenol of preparation 67 using the method of preparation 68 to give the title compound as a brown gum.
¹HNMR (400 MHz, CD₃OD) δ: 4.17 (s, 2H), 6.80 (dd, 1H), 7.04 (t, 1H), 7.08-7.11 (m, 1H), 7.26 (t, 1H), 7.41 (d, 1H), 7.50 (t, 1H), 7.63 (d, 1H), 7.69 (s, 1H) ppm.
MS (electrospray) m/z 198 [M−H]⁻, 200 [M+H]⁺

Preparation 70: 3'-(Aminomethyl)biphenyl-2-ol

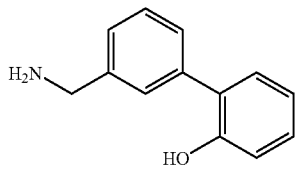

Prepared from the phenol of preparation 63 using the method of preparation 68 to give the title compound as a colourless solid.
¹HNMR (400 MHz, CD₃OD) δ: 4.19 (s, 2H), 6.93-6.97 (m, 2H), 7.19-7.23 (m, 1H), 7.31 (d, 1H), 7.41 (dd, 1H), 7.50-7.53 (m, 1H), 7.65-7.69 (m, 2H) ppm.
MS (electrospray) m/z 200 [M+H]⁺

Preparation 71: 2'-(Aminomethyl)biphenyl-2-ol

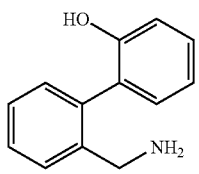

Prepared from preparation 65 using the method of preparation 68 to give the title compound as a colourless solid.
¹HNMR (400 MHz, CD₃OD) δ: 4.03 (s, 2H), 6.99-7.04 (m, 2H), 7.19 (dd, 1H), 7.30-7.34 (m, 2H), 7.50-7.58 (m, 3H) ppm.
MS (electrospray) m/z 200 [M+H]⁺

Preparation 72: 2'-(Aminomethyl)biphenyl-3-ol

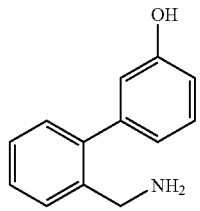

Prepared from preparation 66 using the method of preparation 68 to give the title compound as a colourless solid.
¹HNMR (400 MHz, CD₃OD): 4.15 (s, 2H), 6.79-6.84 (m, 2H), 6.88-6.91 (m, 1H), 7.31-7.35 (m, 1H), 7.37-7.40 (m, 1H), 7.48-7.54 (m, 2H), 7.56-7.60 (m, 1H) ppm.
MS (electrospray) m/z 200 [M+H]⁺

Preparation 73: (4-{[tert-Butyl(dimethyl)silyl]oxy}phenyl)acetonitrile

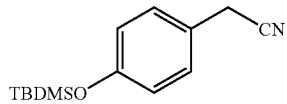

A solution of (4-hydroxyphenyl)acetonitrile (6.01 g, 45.1 mmol) in N,N-dimethylformamide (60 ml) was treated with imidazole (3.819, 58.6 mmol), tert-butyldimethylsilyl chloride (7.49 g, 49.6 mmol) and N,N-dimethylaminopyridine (20 mg) and the resulting solution left to stir at room temperature under a nitrogen atmosphere for 16 hours. The reaction mixture was diluted with water (200 ml) and extracted with ethyl acetate (200 ml×2). The combined organic extracts were washed with sat. aq. sodium chloride (200 ml), dried (sodium sulfate) and the solvent removed in vacuo. Purification by column chromatography on silica gel eluting with ethyl acetate:pentane (0:100 changing to 10:90) gave the title compound as a pale yellow oil (9.44 g).
¹HNMR (400 MHz, CDCl₃) δ: 0.19 (s, 6H), 0.97 (s, 9H), 3.66 (s, 2H), 6.82 (d, 2H), 7.17 (d, 2H) ppm.
MS (APCI) m/z 265 [M+NH₄]⁺

Preparation 74: 2-(4-{[tert-Butyl(dimethyl)silyl]oxy}phenyl)-2-methyl propanenitrile

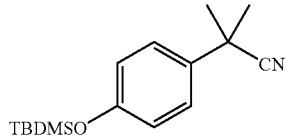

A solution of the nitrile from preparation 73 (5.62 g, 22.7 mmol), methyl iodide (3.11 ml, 50 mmol), and 18-crown-6 (1.5 g, 5.6 mmol) in dry tetrahydrofuran (300 ml) was cooled to −78° C. under a nitrogen atmosphere. Potassium tert-butoxide (50 ml of a 1 M solution in tetrahydrofuran, 50 mmol) was added dropwise over 20 minutes and the reaction mixture then allowed to warm gradually to room temperature. After 2 hours the reaction was recooled to −78° C. and quenched by addition of sat. aq. ammonium chloride (200 ml) and allowed to warm to room temperature. The resulting solution was extracted with ethyl acteate (300 ml×2), the combined organics were dried (sodium sulfate) and the solvent removed in vacuo. Purification by column chromatography on silica gel eluting with ethyl acetate:pentane (0:100 changing to 10:90) gave the title compound as a colourless oil (4.75 g).

$^1$HNMR (400 MHz, CDCl$_3$) δ: 0.19 (s, 6H), 0.97 (s, 9H), 1.68 (s, 6H), 6.82 (d, 2H), 7.30 (d, 2H) ppm.

MS (APCI) m/z 293 [M+NH$_4$]$^+$

Preparation 75: [2-(4-{[tert-Butyl(dimethyl)silyl]oxy}phenyl)-2-methyl propyl]amine

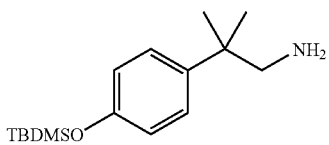

A solution of the nitrile from preparation 74 (0.75 g, 2.7 mmol) in diethyl ether (5 ml) was added dropwise to a cold (0° C.) solution of lithium aluminium hydride in diethyl ether (2.98 ml of a 1 M solution). The resulting solution was stirred at 0° C. for 3 hours and then quenched by addition of water (0.1 ml), 2N aqueous sodium chloride (0.1 ml), and further water (0.3 ml). The resulting suspension was filtered and the filtrate concentrated in vacuo. Purification by column chromatography on silica gel eluting with dichloromethane:methanol:0.880 ammonia (97:3:0.5 changing to 93:7:0.5) gave the title compound as a colourless oil (0.52 g).

$^1$HNMR (400 MHz, CDCl$_3$) δ: 0.18 (s, 6H), 0.97 (s, 9H), 1.00 (bs, 2H), 1.25 (s, 6H), 2.73 (s, 2H), 6.78 (d, 2H), 7.16 (d, 2H) ppm.

MS (APCI) m/z 280 [M+H]$^+$

Preparation 76:
4-(Aminomethyl)-2,6-dimethylphenol hydrochloride

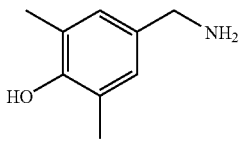

A solution of borane in tetrahydrofuran (27.1 ml of a 1M solution, 27.1 mmol) was added dropwise to a solution of 3,5-dimethyl-4-hydroxybenzonitrile (1.0 g, 6.79 mmol) in tetrahydrofuran (70 ml) and the resulting solution heated to reflux under a nitrogen atmosphere for 16 hours. The reaction was cooled to room temperature and treated with 6N hydrochloric acid (20 ml) and refluxed for a further 30 minutes. The reaction mixture was cooled to room temperature and the solvent removed in vacuo. Purification using strong cation exchange resin, eluting biproducts with methanol followed by 2M ammonia in methanol to elute the product gave the title compound as an orange oil. The oil was treated with 1M hydrogen chrloide in methanol (20 ml) and the solvent removed in vacuo to give the title compound as a pale yellow solid (1.12 g).

$^1$HNMR (400 MHz, CDCl$_3$) δ: 2.22 (s, 6H), 3.75 (s, 2H), 6.90 (s, 2H).

Preparation 77: 2-(Aminomethyl)-4-chlorophenol hydrochloride

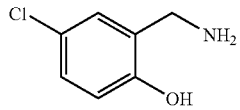

Prepared from 5-chloro-2-hydroxybenzonitrile using the procedure described in preparation 76.

$^1$HNMR (400 MHz, CDCl$_3$) δ: 4.08 (s, 2H), 6.87 (d, 1H), 7.27 (d, 1H), 7.35 (s, 1H).

MS (APCI) m/z 156 [M−H]$^-$, 158 [M+H]$^+$

Preparation 77: 4'-(Aminomethyl)biphenyl-4-ol hydrochloride

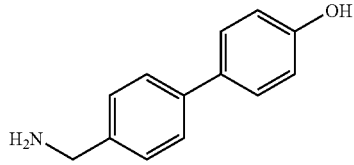

Prepared from 4'-hydroxybiphenyl-4-carbonitrile using the procedure described in preparation 76.

$^1$HNMR (400 MHz, CD$_3$OD) δ: 4.10 (s, 2H), 6.83 (d, 2H), 7.44-7.46 (m, 4H), 7.60 (d, 2H) ppm.

Preparation 79:
3,5-Dichloro-N-ethyl-2-hydroxybenzamide

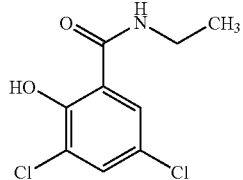

Prepared from 3,5-dichloro-2-hydroxybenzoic acid and ethylamine using the method of preparation 57 to give the title compound as a pale yellow solid.

$^1$HNMR (400 MHz, CDCl$_3$) δ: 1.28 (t, 3H), 3.47-3.54 (m, 2H), 6.29-6.36 (bs, 1H), 7.27 (d, 1H), 7.48 (d, 1H) ppm.

MS (electrospray) m/z 232 [M−H]$^{31}$

Preparation 80:
2,4-Dichloro-6-[(ethylamino)methyl]phenol

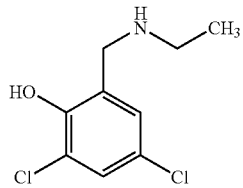

A solution of the amide from preparation 79 (0.77 g, 3.29 mmol) in tetrahydrofuran (10 ml) was cooled to 0° C. and treated with borane.tetrahydrofuran complex (9.9 ml of a 1M solution in tetrahydrofuran, 9.9 mmol). The resulting solution was allowed to warm to room temperature over 20 minutes and then heated to reflux for 16 hours. The reaction mixture was cooled to 0° C. and quenched by addition of methanol (until effervescence ceased). The resulting solution was allowed to warm to room temperature over 2 hours and then the solvent was removed in vacuo. The residue was dissolved in dichloromethane (40 ml) and washed with water (10 ml×2), sat. aq. sodium chloride (10 ml), dried (sodium sulfate) and reduced in vacuo to give a colourless oil. Purification by column chromatography on silica gel eluting with dichloromethane:methanol (98:2 changing to 95:5) gave the title compound as a colourless solid (0.53 g).

$^1$HNMR (400 MHz, CDCl$_3$) δ: 1.17 (t, 3H), 2.72 (q, 2H), 3.98 (s, 2H), 6.86 (d, 1H), 7.23 (d, 1H) ppm.

Preparation 81: 6-Hydroxy-N-methyl-1-naphthamide

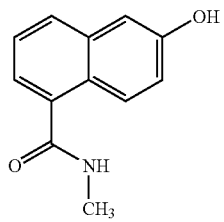

Prepared from 6-hydroxy-1-naphthoic acid and methylamine using the method of preparation 57 to give the title compound as a pale orange solid.

$^1$HNMR (400 MHz, CD$_3$OD) δ: 2.97 (s, 3H), 7.10-7.14 (m, 2H), 7.34-7.40 (m, 2H), 7.73 (dd, 1H), 8.04 (d, 1H) ppm.

Preparation 82:
5-[(Methylamino)methyl]-2-naphthol

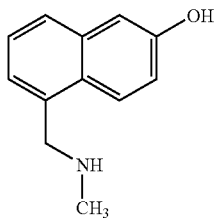

Prepared from the amide of preparation 81 using the method of preparation 80 to give the title compound as a pale pink solid.

$^1$HNMR (400 MHz, CD$_3$OD) δ: 2.48 (s, 3H), 4.14 (s, 2H), 7.11-7.14 (m, 2H), 7.25 (d, 1H), 7.33 (t, 1H), 7.59 (d, 1H), 7.94 (d, 1H) ppm.

MS (electrospray) m/z 186 [M−H]$^-$, 188 [M+H]$^+$

Preparation 83:
3-Hydroxy-5-(trifluoromethyl)benzamide

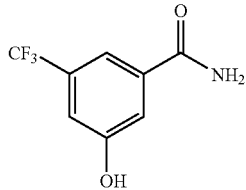

Prepared from 3-hydroxy-5-(trifluoromethyl)benzoic acid using the method of preparation 58 to give the title compound as a pale yellow solid.

$^1$HNMR (400 MHz, CD$_3$OD) δ: 7.18 (t, 1H), 7.50 (t, 1H), 7.60-7.61 (m, 1H) ppm.

MS (electrospray) m/z 204 [M−H]$^-$

Preparation 84:
3-(Aminomethyl)-5-(trifluoromethyl)phenol

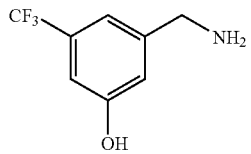

Prepared from the amide of preparation 83 using the method of preparation 80 to give the title compound as a pale yellow oil.

$^1$HNMR (400 MHz, CD$_3$OD) δ: 3.81 (s, 2H), 6.91 (s, 1H), 6.98 (s, 1H), 7.09 (s, 1H) ppm.

MS (electrospray) m/z 192 [M+H]$^+$

Preparation 85: 3-(Aminomethyl)-5-chlorophenol

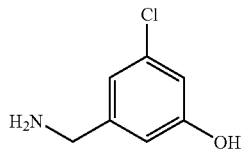

Prepared from 3-chloro-5-hydroxybenzonitrile using the method of preparation 76 to give the title compound as a pale yellow solid.

$^1$HNMR (400 MHz, CD$_3$OD) δ: 3.69 (s, 2H), 6.65 (d, 2H), 6.79 (t, 1H) ppm.

MS (electrospray) m/z 158 [M+H]$^+$

Preparation 86:
3-[(Acetylamino)methyl]-5-chlorophenyl acetate

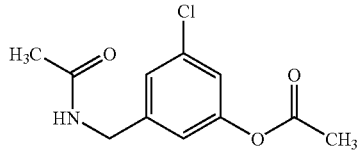

A solution of the amine of preparation 85 (700 mg, 4.46 mmol) in tetrahydrofuran (20 ml) was treated with triethylamine (1.3 ml, 8.9 mmol) and acetyl chloride (0.64 ml, 8.9 mmol). The resulting mixture was left to stir at room temperature for 1 hour. The reaction mixture was filtered and the filtrate reduced in vacuo to give the title compound as a colourless solid (1.07 g).

$^1$HNMR (400 MHz, CDCl$_3$) δ: 2.15 (s, 3H), 2.27 (s, 3H), 3.71-3.75 (m, 1H), 4.38-4.41 (m, 2H), 6.92 (s, 1H), 7.02 (s, 1H), 7.13 (s, 1H) ppm.

MS (electrospray) m/z 264 [M+Na]$^+$

Preparation 87:
N-(3-Chloro-5-hydroxybenzyl)acetamide

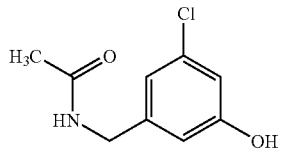

A solution of the diacetate of preparation 86 (1.07 g, 4.44 mmol) in methanol (10 ml) was treated with sodium methoxide (30 mg, 0.55 mmol) and the resulting mixture left to stir at room temperature for 6 hours. The solvent was removed in vacuo and the residue purified by column chromatography on silica gel eluting with ethyl acetate:pentane (1:1 changing to 1:0) gave the title compound as a yellow solid (0.78g).

$^1$HNMR (400 MHz, CDCl$_3$) δ: 2.05 (s, 3H), 4.33 (d, 2H), 6.08-6.14 (m, 1H), 6.73 (d, 2H), 6.79 (t, 1H) ppm.

MS (electrospray) m/z 200 [M+H]$^+$

Preparation 88:
3-Chloro-5-[(ethylamino)methyl]phenol

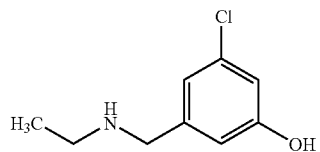

Prepared from the amide of preparation 87 (0.75 g, 3.76 mmol)) using the method of preparation 59 to give the title compound as a colourless solid (0.48 g).

$^1$HNMR (400 MHz, CD$_3$OD) δ: 1.14 (t, 3H), 2.71 (q, 2H), 3.25-3.27 (m, 1H), 3.72 (s, 2H), 6.66-6.68 (m, 2H), 6.79 (s, 1H) ppm.

MS (electrospray) m/z [M−H]$^-$

Preparation 89: 4-([tert-Butyl(dimethyl)silyl]oxy)-2-chlorobenzaldehyde

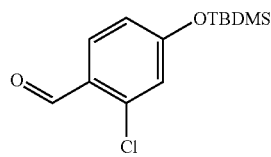

A solution of 2-chloro-4-hydroxybenzaldehyde (5.0 g, 32 mmol), tert-butyl(dimethyl)silyl chloride (5.3 g, 35 mmol), imidazole (2.9 g, 45 mmol) and N,N-dimethylaminopyridine (10 mg) in N,N-dimethylformamide (40 ml) was stirred at room temperature under a nitrogen atmosphere for 16 hours. The solvent was removed in vacuo and the residue partitioned between ethyl acteate (100 ml) and water (100 ml). The organic phase was separated, washed with sat. aq. sodium chloride (50 ml), dried (sodium sulfate) and reduced in vacuo. Further purification by column chromatography on silica gel eluting with pentane:ethyl acetate (3:1 changing to 2:1) gave the title compound as a colourless oil (6.50 g).

$^1$HNMR (400 MHz, CDCl$_3$) δ: 0.25 (s, 6H), 0.97 (s, 9H), 6.80 (dd, 1H), 6.87 (d, 1H), 7.84 (d, 1H), 10.32 (s, 1H) ppm.

Preparation 90: N-(4-{[tert-Butyl(dimethyl)silyl]oxy}-2-chlorobenzyl)prop-2-en-1-amine

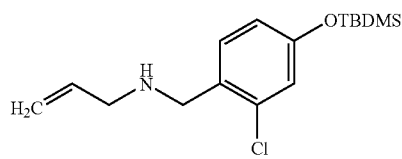

A solution of the aldehyde from preparation 89 (6.50 g, 24.0 mmol) and allylamine (1.51 g, 26.4 mmol) in dichloromethane (60 ml) was treated with sodium triacetoxyborohydride (7.6 g, 35.6 mmol) and the resulting suspension allowed to stir at room temperature for 16 hours. Sat. aq. sodium bicarbonate (50 ml) was added and the organic phase separated. The organic phase was washed with sat. aq. sodium chloride (50 ml), dried (sodium sulfate) and the solvent removed in vacuo to give a yellow oil. Purification by column chromatography on silica gel eluting with pentane:ethyl acetate (3:1 changing to 2:1) gave the title compound as a colourless oil (2.80 g).

$^1$HNMR (400 MHz, CDCl$_3$) δ: 0.19 (s, 6H), 0.97 (s, 9H), 1.84 (bs, 1H), 3.26 (d, 2H), 3.81 (s, 2H), 5.12 (dd, 1H), 5.20 (dd, 1H), 5.88-5.98 (m, 1H), 6.71 (dd, 1H), 6.85-6.86 (d, 1H), 7.24 (d, 1H) ppm.

MS (electrospray) m/z 312 [M+H]$^+$

Preparation 91:
4-[(Allylamino)methyl]-2,6-dichlorophenol

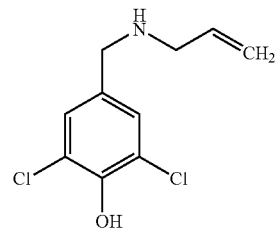

Prepared from 3,5-dichloro-4-hydroxybenzaldehyde and allylamine using the method of preparation 90 to give the title compound as a colourless oil.

$^1$HNMR (400 MHz, DMSO$_{d6}$) δ: 3.11 (d, 2H), 3.50 (s, 2H), 5.06 (d, 1H), 5.16 (d, 1H), 5.77-5.90 (m, 1H), 7.10 (s, 2H) ppm.

MS (electrospray) m/z 232/234 [M+H]$^+$

Preparation 92: (4-{[tert-Butyl(dimethyl)silyl]oxy}-2-chlorobenzyl)amine

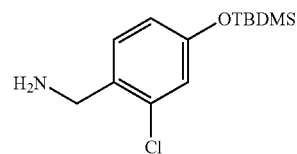

A solution of the amine from preparation 91 (2.8 g, 9.0 mmol), dimethyl barbituric acid (7.0 g, 45 mmol) and tetrakis (triphenylphosphine) palladium(0) (0.10 g, 0.08 mmol) in dichloromethane (80 ml) was heated to reflux for 4 hours. The cooled solution was reduced in vacuo and the residue partitioned between ethyl acetate (50 ml) and 1N aqueous sodium hydroxide (50 ml). The organic phase was separated, washed with sat. aq. sodium chloride (50 ml), dried (sodium sulfate) and reduced in vacuo. Further purification by column chromatography on silica gel eluting with dichloromethane: methanol:0.880 ammonia (98:2:0 changing to 95:5:0.5) gave the title compound as a colourless oil (1.70 g).

$^1$HNMR (400 MHz, CDCl$_3$) δ: 0.19 (s, 6H), 0.97 (s, 9H), 1.89 (s, 2H), 3.85 (s, 2H), 6.70 (dd, 1H), 6.85-6.86 (dd, 1H), 7.21 (d, 1H) ppm.

Preparation 93: (4-{[tert-Butyl(dimethyl)silyl]oxy}benzyl)methylamine

Prepared from the aldehyde of preparation 89 and methylamine using the method of preparation 90 to give the title compound as a yellow oil.

$^1$HNMR (400 MHz, CDCl$_3$) δ: 0.23 (s, 6H), 1.00 (s, 9H), 2.50 (s, 3H), 3.93 (s, 2H), 6.70-6.73 (m, 1H), 6.76 (d, 1H), 7.20 (d, 1H) ppm.

MS (electrospray) m/z 286/288 [M+H]$^+$

Preparation 94: 4-(Aminomethyl)-2,6-dichlorophenol barbiturate

Prepared from the amine from preparation 91 using the method of preparation 92 to give the title compound as the barbituric acid salt.

$^1$HNMR (400 MHz, DMSO$_{d6}$) δ: 2.60-4.40 (broad multiplet, 2H), 3.03 (s, 6H), 3.93 (s, 2H), 7.49 (s, 2H) ppm.

MS (electrospray) m/z 192/194[M+H]$^+$

Preparation 95: 4-{[tert-Butyl(dimethyl)silyl]oxy}-2,3-dichloro benzaldehyde Prepared from 2,3-dichloro-4-hydroxybenzaldehyde according to the method for preparation 89 to give the title compound as yellow oil.

$^1$HNMR (400 MHz, CDCl$_3$) δ: 0.29 (s, 6H), 1.04 (s, 9H), 6.88 (d, 1H), 7.76 (d, 1H), 10.32 (s, 1H) ppm.

Preparation 96: N-(4-{[tert-Butyl(dimethyl)silyl]oxy}-2,3-dichlorobenzyl)prop-2-en-1-amine Prepared according to preparation 90 using allylamine and the aldehyde from preparation 95 to give the title compound as a colourless oil.

$^1$HNMR (400 MHz, CDCl$_3$) δ: 0.20 (s, 6H), 1.01 (s, 9H), 3.25 (d, 2H), 3.82 (s, 2H), 5.10 (dd, 1H), 5.18 (dd, 1H), 5.85-5.93 (m, 1H), 6.76 (d, 1H), 7.13 (d, 1H) ppm.

MS (electrospray) m/z 346/348 [M+H]$^+$

Preparation 97: (4-{[tert-Butyl(dimethyl)silyl]oxy}-2,3-dichlorobenzyl)amine Prepared according to preparation 92 using amine from preparation 96 to give the title compound as a colourless oil.

$^1$HNMR (400 MHz, CD$_3$OD) δ: 0.23 (s, 6H), 1.03 (s, 9H), 3.92 (s, 2H), 6.77 (d, 1H), 7.12 (d, 1H) ppm.

Preparation 98: 4-{[tert-Butyl(dimethyl)silyl]oxy}-1-naphthaldehyde

Prepared from 2,3-dichloro-4-hydroxybenzaldehyde according to the method for preparation 89 to give the title compound as brown solid.

$^1$HNMR (400 MHz, CDCl$_3$) δ: 0.36 (s, 6H), 1.10 (s, 9H), 6.94 (d, 1H), 7.56 (dd, 1H), 7.68 (dd, 1H), 7.86 (d, 1H), 8.27 (dd, 1H), 9.30 (dd, 1H), 10.21 (s, 1H) ppm.

Preparation 99: N-[(4-{[tert-Butyl(dimethyl)silyl]oxy}-1-naphthyl)methyl]prop-2-en-1-amine

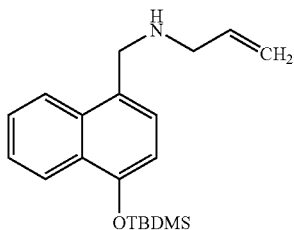

Prepared according to preparation 90 using allylamine and the aldehyde from preparation 98 to give the title compound as a yellow oil.

$^1$HNMR (400 MHz, CDCl$_3$) δ: 0.30 (s, 6H), 1.11 (s, 9H), 1.97 (bs, 1H), 3.39 (d, 2H), 4.17 (s, 2H), 5.16 (dd, 1H), 5.25 (dd, 1H), 5.95-6.05 (m, 1H), 6.82 (d, 1H), 7.32 (d, 1H), 7.47-7.57 (m, 2H), 8.07 (d, 1H), 8.25 (d, 1H) ppm.

MS (electrospray) m/z 328 [M+H]$^+$, 655 [2M+H]$^+$

Preparation 100: [(4-{[tert-butyl(dimethyl)silyl]oxy}-1-naphthyl)methyl]amine

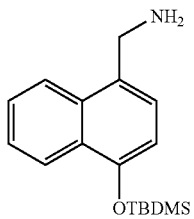

Prepared according to preparation 92 using amine from preparation 99 to give the title compound as a colourless oil.

$^1$HNMR (400 MHz, CDCl$_3$) δ: 0.28 (s, 6H), 1.09 (s, 9H), 2.31 (bs, 2H), 4.24 (s, 2H), 6.80 (d, 1H), 7.27 (t, 1H), 7.46-7.55 (m, 4H), 8.00 (d, 1H), 8.25 (d, 1H).

Preparation 101: 3-Hydroxy-N-methyl-5-(trifluoromethyl)benzamide

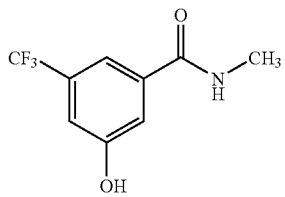

Prepared from 3-hydroxy-5-(trifluoromethyl)benzoic acid and methylamine using the method of preparation 58 to give the title compound as a pale orange solid.

$^1$HNMR (400 MHz, CD$_3$OD) δ: 2.99 (s, 3H), 7.14 (s, 1H), 7.43 (s, 1H), 7.52 (s, 1H) ppm.

MS (electrospray) m/z 218 [M−H]$^−$

Preparation 102: 3-[(Methylamino)methyl]-5-(trifluoromethyl)phenol

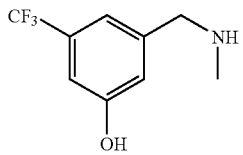

Prepared from the amide of preparation 101 using the method of preparation 59 to give the title compound as a colourless solid.

$^1$HNMR (400 MHz, CD$_3$OD) δ: 2.41 (s, 3H), 3.75 (s, 2H), 6.93 (s, 1H), 6.98 (s, 1H), 7.09 (s, 1H) ppm.

MS (electrospray) m/z 206 [M+H]$^+$

Preparation 103: 4-(Aminomethyl)-3,5-dimethylphenol

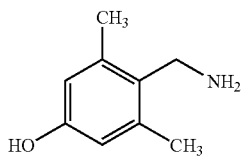

Prepared from 4-hydroxy-2,6-dimethylbenzonitrile using the method of preparation 76 to give the title compound as a colourless solid.

$^1$HNMR (400 MHz, D$_2$O) δ: 2.09 (s, 6H), 3.90 (s, 2H), 6.95 (s, 2H) ppm.

Preparation 104: (4-Hydroxy-2,5-dimethylphenyl)acetonitrile

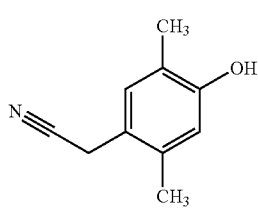

A solution of (4-methoxy-2,5-dimethylphenyl)acetonitrile (0.5 g, 2.9 mmol) in dichloromethane (10 ml) was cooled to −80° C. and treated with a solution of boron tribromide in dichloromethane (14.3 ml of a 1M solution, 14.3 mmol). The reaction mixture was stirred at −80° C. for a further 30 minutes and then gradually allowed to warm to room temperature over a period of 2 hours. The reaction mixture was quenched with saturated aqueous sodium bicarbonate (20 ml) and the organic phase separated. The organic phase was washed with saturated aqueous sodium chloride (20 ml), dried (sodium sulfate) and the solvent removed in vacuo to give a pale brown solid. Purification by column chromatography on silica gel eluting with ethyl acetate:pentane (1:4 changing to 1:2) gave the title compound as a colourless solid (0.28 g).

$^1$HNMR (400 MHz, CD$_3$OD) δ: 2.13 (s, 3H), 2.23 (s, 3H), 3.66 (s, 2H), 6.60 (s, 1H), 6.98 (s, 1H) ppm.

MS (electrospray) m/z 160 [M−H]$^-$

Preparation 105:
(4-Hydroxy-2,3-dimethylphenyl)acetonitrile

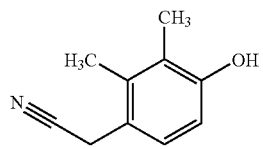

Prepared from (4-methoxy-2,3-dimethylphenyl)acetonitrile using the method from preparation 104 to give the title compound as a pale yellow solid.

$^1$HNMR (400 MHz, CDCl$_3$) δ: 2.20 (s, 3H), 2.24 (s, 3H), 3.62 (s, 2H), 4.91 (bs, 1H), 6.64 (d, 1H), 7.03 (d, 1H) ppm.

MS (electrospray) m/z 160 [M−H]$^-$

Preparation 106:
(4-Hydroxy-3-methylphenyl)acetonitrile

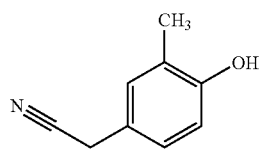

Prepared from (4-methoxy-3-methylphenyl)acetonitrile using the method from preparation 104 to give the title compound as a pale yellow solid.

$^1$HNMR (400 MHz, CDCl$_3$) δ: 2.25 (s, 3H), 3.65 (s, 2H), 4.98 (bs, 1H), 6.76 (d, 1H), 7.01 (d, 1H), 7.07 (s, 1H) ppm.

MS (electrospray) m/z 146 [M−H]$^-$

Preparation 107:
4-(2-Aminoethyl)-2,5-dimethylphenol

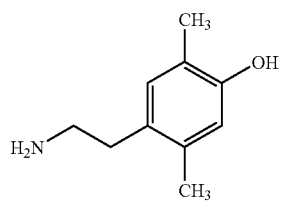

A solution of the nitrile from preparation 104 (0.28 g, 1.74 mmol) in ethanol (15 ml) was hydrogenated at 60 psi over Raney Nickel (0.1 g, 50% w/w) for 16 hours. The reaction mixture was filtered and the solvent removed in vacuo. The residue was purified by strong cation exchange resin eluting non-basic impurities with methanol and then 1M ammonia in methanol to give the title compound as a colourless oil.

$^1$HNMR (400 MHz, CD$_3$OD) δ: 2.11 (s, 3H), 2.19 (s, 3H), 2.63-2.67 (m, 2H), 2.72-2.76 (m, 2H), 6.54 (s, 1H), 6.81 (s, 1H) ppm.

MS (electrospray) m/z 166 [M+H]$^+$

Preparation 108:
4-(2-Aminoethyl)-2,3-dimethylphenol

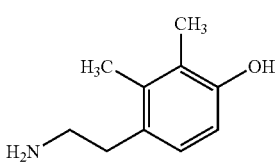

Prepared from the nitrile of preparation 105 using the method of preparation 107 to give the title compound as a colourless oil.

$^1$HNMR (400 MHz, CD$_3$OD) δ: 2.12 (s, 3H), 2.19 (s, 3H), 2.68-2.75 (m, 4H), 6.55 (d, 1H), 6.78 (d, 1H) ppm.

MS (electrospray) m/z 166 [M+H]$^+$

Preparation 109: 4-(2-Aminoethyl)-2-methylphenol

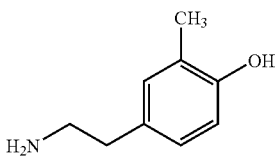

Prepared from the nitrile of preparation 106 using the method of preparation 107 to give the title compound as a colourless oil.

$^1$HNMR (400 MHz, CD$_3$OD) δ: 2.15 (s, 3H), 2.60-2.64 (m, 2H), 2.79-2.83 (m, 2H), 6.66 (d, 1H), 6.82 (d, 1H), 6.90 (s, 1H) ppm.

MS (electrospray) m/z 152 [M+H]$^+$

EXAMPLES 1-38

The appropriate protected alcohol (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. If a solid product precipitated the reaction mixture was filtered and washed with methanol:water (2 ml, 1:1 by volume) to give the title compound. If no product precipitated the reaction mixture was concentrated in vacuo and the residue purified by column chromatography on silica gel eluting with dichloromethane:methanol:0.88 ammonia 98:2:0 to 95:5:0.5 to 90:10:1 to yield the title product.

Alternatively, the following process can be used for the synthesis of examples 1 to 38: A solution of the appropriate protected alcohol (2.87 mmol) in methanol (80 ml) is treated with a solution of ammonium fluoride (1.06 g, 28.7 mmol) in water (53 ml) and the resulting mixture heated at 40° C. for 16 hours. The reaction is cooled to room temperature and filtered, washing with a mixture of water and methanol (1:1 by volume, 3×10 ml), methanol (2×10 ml). The solid is dried in vacuo to give the desired compound.

EXAMPLE 1

2-(3-{2-[((2R)-2-Hydroxy-2-{4-hydroxy-3-[(methyl-sulfonyl)amino]phenyl}ethyl)amino]-2-methylpropyl}phenyl)-N-(4-hydroxy-3-methoxyben-zyl)acetamide

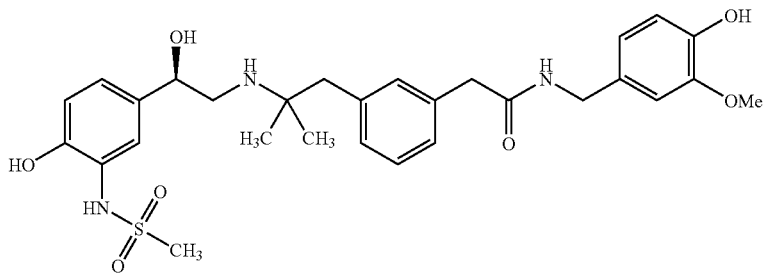

Preparation 18 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was concentrated in vacuo and the residue purified by column chromatography on silica gel eluting with dichloromethane:methanol:0.88 ammonia 98:2:0 to 95:5:0.5 to 90:10:1 to yield the title product as a colourless solid.

$^1$HNMR (CD$_3$OD, 400 MHz) δ: 1.04 (s, 3H), 1.06 (s, 3H), 2.68-2.90 (m, 7H), 3.53 (s, 2H), 3.74 (s, 3H), 4.23 (m, 2H), 4.62 (m, 1H), 6.67 (m, 2H), 6.77 (m, 1H), 6.85 (d, 1H), 7.01-7.22 (m, 6H), 7.37 (m, 1H) ppm.

MS (electrospray) m/z 572 [M+H]$^+$

EXAMPLE 2

N-[(4'-Hydroxybiphenyl-4-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide

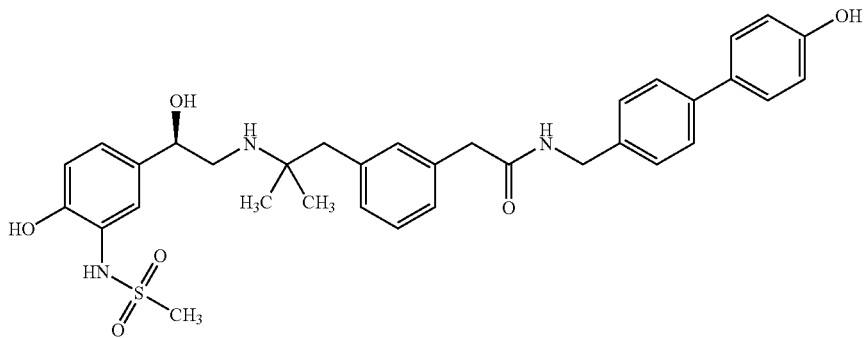

Preparation 19 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was filtered and the solid washed with methanol:water (2 ml, 1:1 by volume) to give the title compound as a colourless solid.

$^1$HNMR (400 MHz, DMSO$_{d6}$) δ: 0.90 (s, 3H), 0.92 (s, 3H), 2.56 (s, 2H), 2.62-2.65 (m, 2H), 2.88 (s, 3H), 3.43 (s, 2H), 4.25 (2H, d), 4.40-4.43 (m, 1H), 6.80-6.82 (m, 3H), 6.96-7.01 (m, 2H), 7.07-7.10 (m, 2H), 7.14-7.18 (m, 2H), 7.23 (d, 2H), 7.42-7.48 (m, 4H), 8.47 (t, 1H).

MS (electrospray) m/z 618 [M+H]$^+$

EXAMPLE 3

N-(4-Chloro-2-hydroxybenzyl)-2-(3-{2-[((2R)-2-hydroxy-2-{4-hydroxy-3-[(methylsulfonyl)amino]phenyl}ethyl)amino]-2-methylpropyl}phenyl)acetamide

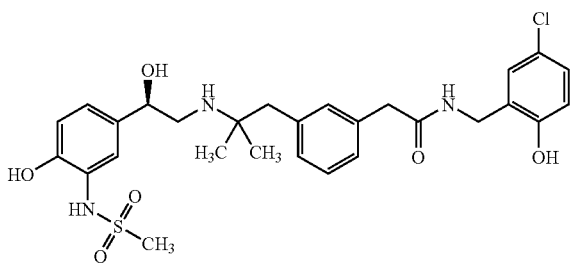

Preparation 20 (0.075 mmol) was dissolved in ethanol (4 ml) and the solution treated with a solution of ammonium fluoride (16 mg, 0.43 mmol) in water (300 µL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, DMSO$_{d6}$) δ: 0.90 (s, 3H), 0.91 (s, 3H), 2.56 (s, 2H), 2.59-2.67 (m, 2H), 2.88 (s, 3H), 3.44 (s, 2H), 4.16 (s, 2H), 4.40-4.43 (m, 1H), 6.76-6.81 (m, 2H), 6.96-7.18 (m, 8H), 8.42 (s, 1H).

MS (electrospray) m/z 574 [M−H]$^-$, 576 [M+H]$^+$

EXAMPLE 4

N-(4-Hydroxy-3,5-dimethylbenzyl)-2-(3-{2-[((2R)-2-hydroxy-2-{4-hydroxy-3-[(methylsulfonyl)amino]phenyl}ethyl)amino]-2-methylpropyl}phenyl)acetamide

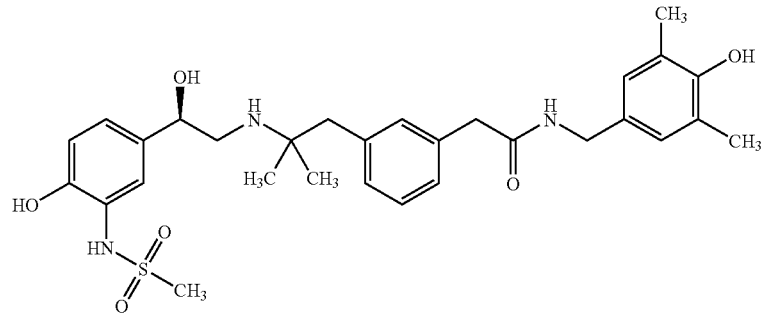

Preparation 21 (0.075 mmol) was dissolved in ethanol (4 ml) and the solution treated with a solution of ammonium fluoride (16 mg, 0.43 mmol) in water (300 µL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, DMSO$_{d6}$) δ: 0.90 (s, 3H), 0.91 (s, 3H), 2.08 (s, 6H), 2.55 (s, 2H), 2.62-2.65 (m, 2H), 2.88 (s, 3H), 3.38 (s, 2H partially obscured by H$_2$O), 4.05 (d, 2H), 4.40-4.43 (m, 1H), 6.71 (s, 2H), 6.81 (d, 1H), 6.95-7.01 (m, 2H), 7.05-7.09 (m, 2H), 7.13-7.18 (m, 2H), 8.28-8.31 (t, 1H).

EXAMPLE 5

2-(3-{2-[((2R)-2-Hydroxy-2-{4-hydroxy-3-[(methylsulfonyl)amino]phenyl}ethyl)amino]-2-methylpropyl}phenyl)-N-[(2-hydroxy-1-naphthyl)methyl]acetamide

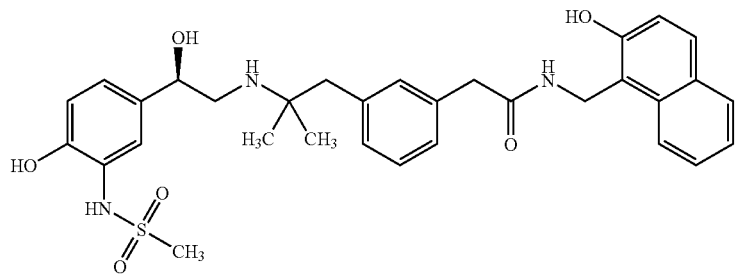

Preparation 22 (0.075 mmol) was dissolved in ethanol (4 ml) and the solution treated with a solution of ammonium fluoride (16 mg, 0.43 mmol) in water (300 L). The reaction mixture was then stirred at 50° C. for 18 hours before being allowed to cool to room temperature. The reaction mixture was concentrated in vacuo and the residue purified by column chromatography on silica gel eluting with dichloromethane: methanol:0.88 ammonia 98:2:0 to 95:5:0.5 to 90:10:1 to yield the title product as a colourless solid.

$^1$HNMR (400 MHz, DMSO$_{d6}$) δ: 0.86 (s, 3H), 0.87 (s, 3H), 2.46-2.68 (m, 4H), 2.90 (s, 3H), 3.40 (s, 2H), 4.41-4.47 (m, 1H), 4.63 (d, 2H), 6.83 (d, 1H), 6.94-7.05 (m, 4H), 7.11-7.16 (m, 2H), 7.19 (s, 1H), 7.27 (t, 1H), 7.40 (t, 1H), 7.72 (d, 1H), 7.79 (d, 1H), 7.88 (d, 1H), 8.48-8.52 (bs, 1H).

MS (electrospray) m/z 590 [M–H]$^-$

EXAMPLE 6

2-(3-{(2-[((2R)-2-Hydroxy-2-{4-hydroxy-3-[(methylsulfonyl)amino]phenyl}ethyl)amino]-2-methylpropyl)phenyl)-N-[(6-hydroxy-2-naphthyl)methyl]acetamide

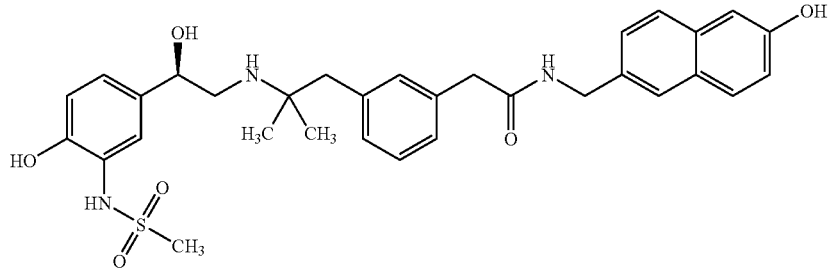

Preparation 23 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, DMSO-d$_6$) δ: 0.90 (s, 3H), 0.92 (s, 3H), 2.49-2.68 (m, 4H), 2.89 (s, 3H), 3.44 (s, 2H), 4.34 (d, 2H), 4.40-4.43 (m, 1H), 6.80 (d, 1H), 6.96-7.17 (m, 7H), 7.23 (d, 1H), 7.51 (s, 1H), 7.58 (d. 1H), 7.61 (d, 1H), 8.50 (dd, 1H).

MS (electrospray) m/z 590 [M–H]$^-$, 592 [M+H]$^+$, 614 [M+Na]$^+$

EXAMPLE 7

N-[(4'-Hydroxybiphenyl-3-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide

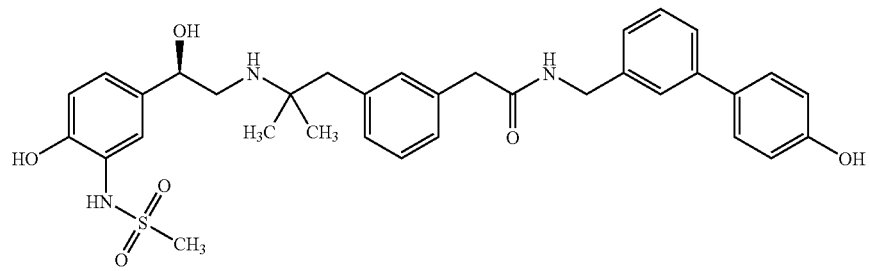

Preparation 24 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, DMSO$_{d6}$) δ: 0.88 (s, 3H), 0.90 (s, 3H), 2.66-2.54 (m, 4H), 2.88 (s, 3H), 3.43 (s, 2H), 4.29 (d, 2H), 4.39-4.43 (m, 1H), 6.79-6.82 (m, 3H), 6.96-7.01 (dd, 2H), 7.07-7.17 (m, 5H), 7.27-7.31 (dd, 1H), 7.36-7.41 (m, 4H), 8.52 (dd, 1H) ppm.

MS (electrospray) m/z 618 [M+H]$^+$

EXAMPLE 8

N-[(3'-Hydroxybiphenyl-3-yl)methyl]-2-(3-{2-[((2R)-2-hydroxy-2-{4-hydroxy-3-[(methylsulfonyl)amino]phenyl}ethyl)amino]-2-methylpropyl}phenyl)acetamide

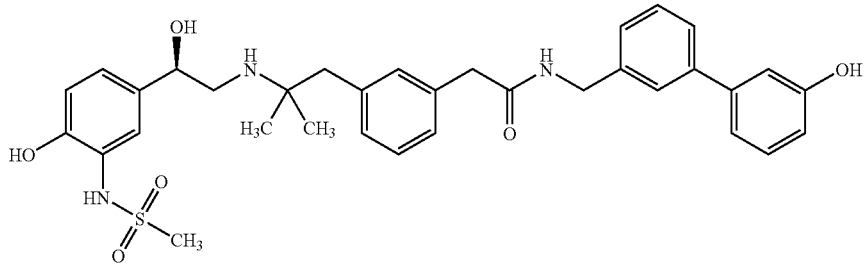

Preparation 25 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, DMSO$_{d6}$) δ: 1.16 (s, 6H), 2.85 (s, 2H), 2.92 (s, 3H), 2.96-3.03 (m, 2H), 3.57 (s, 2H), 4.42 (s, 2H), 4.77-4.79 (m, 1H), 6.74 (d, 1H), 6.90 (d, 1H), 6.95-6.97 (m, 2H), 7.09-7.27 (m, 7H), 7.32 (t, 1H), 7.41-7.42 (m, 3H) ppm.

MS (electrospray) m/z 618 [M+H]$^+$, 6401[M+Na]$^+$, 616 [M−H]$^-$

EXAMPLE 9

2-(3-{2-[((2R)-2-Hydroxy-2-(4-hydroxy-3-[(methylsulfonyl)amino]phenyl)ethyl)amino]-2-methylpropyl}phenyl)-N-[2-(4-hydroxyphenyl)-2-methylpropyl]acetamide

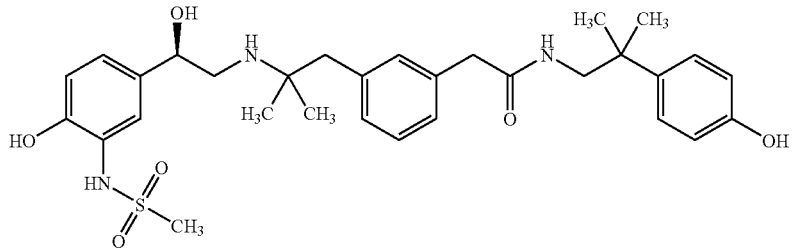

Preparation 26 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was concentrated in vacuo and the residue purified by column chromatography on silica gel eluting with dichloromethane: methanol:0.88 ammonia 98:2:0 to 95:5:0.5 to 90:10:1 to yield the title product as a colourless solid.

$^1$HNMR (400 MHz, DMSO$_{d6}$) δ: 0.91 (s, 3H), 0.92 (s, 3H), 1.11 (s, 6H), 2.56 (s, 2H), 2.64-2.66 (m, 2H), 2.89 (s, 3H), 3.15 (s, 2H), 3.35 (s, 2H), 4.42-4.45 (m, 1H), 6.65 (d, 2H), 6.81 (d, 1H), 6.94-7.03 (m, 4H), 7.07-7.14 (m, 3H), 7.18 (s, 1H), 7.60 (t, 1H).

MS (APCI) m/z 582 [M−H]$^-$, 584 [M+H]$^+$

EXAMPLE 10

N-(3,5-Dichloro-2-hydroxybenzyl)-N-ethyl-2-(3-{2-[((2R)-2-hydroxy-2-{4-hydroxy-3-[(methylsulfonyl)amino]phenyl}ethyl)amino]-2-methylpropyl}phenyl)acetamide

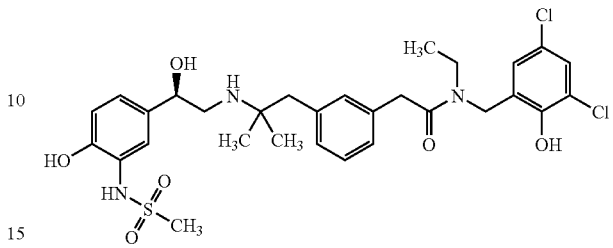

Preparation 27 (0.075 mmol) was dissolved in ethanol (4 ml) and the solution treated with a solution of ammonium fluoride (16 mg, 0.43 mmol) in water (300 μL). The reaction mixture was then stirred at 50° C. for 18 hours before being allowed to cool to room temperature. The reaction mixture was filtered and washed with methanol:water (2 ml, 1:1 by volume) to give the title compound as a colourless solid.

$^1$HNMR (400 MHz, CD$_3$OD) δ: 1.05-1.16 (m, 9H), 2.70-2.96 (m, 7H), 3.32 and 3.34 (2t, 2H), 3.74 and 3.83 (2s, 2H), 4.56 and 4.58 (2s, 2H), 4.64-4.66 (m, 1H), 6.85 (dd, 1H), 7.01-7.26 (m, 7H), 7.36 (dd, 1H).

MS (electrospray) m/z 637 [M−H]$^-$

Examples 11 to 32

| No | Q$^1$ | Data |
|---|---|---|
| 11 | ![structure: N-methyl aminomethyl naphthol] | $^1$HNMR (400 MHz, DMSO$_{d6}$) δ: 0.85 (s, 3 H), 0.86 (s, 3 H), 2.47 (s, 3 H), 2.60-2.63 (m, 2 H), 2.84 (s, 2 H), 2.88 (s, 3 H), 3.61 and 3.75 (2 s, 2 H), 4.38-4.41 (m, 1 H), 4.89 and 5.03 (2 s, 2 H), 6.80 (d, 1 H), 6.93-7.18 (m, 9 H), 7.28 and 7.33 (2 t, 1 H), 7.59 (d, 1 H), 7.92 and 7.74 (2 d, 1 H). MS (electrospray) m/z 604 (M − H)$^-$ |
| 12 | ![structure: biphenyl hydroxy aminomethyl] | $^1$HNMR (400 MHz, DMSO$_{d6}$) δ: 0.88 (s, 3 H), 0.90 (s, 3 H), 2.53 (s, 2 H), 2.61-2.63 (m, 2 H), 2.88 (s, 3 H), 3.42 (s, 2 H), 4.28 (d, 1 H), 4.40-4.43 (m, 2 H), 6.82 (t, 1 H), 6.85 (s, 1 H), 6.91 (d, 1 H), 6.95 (d, 1 H), 7.00 (d, 1 H), 7.05 (s, 1 H), 7.07-7.15 (m, 4 H), 7.17 (d, 1 H), 7.28 (t, 1 H), 7.36-7.40 (m, 2 H) ppm. MS (electrospray) m/z 616 [M − H]$^-$ |
| 13 | ![structure: tetrahydroisoquinoline hydroxy] | $^1$HNMR (400 MHz, DMSO$_{d6}$) δ: 0.89-0.93 (m, 6 H), 2.51-2.54 (m, 2 H, partially obscured by solvent), 2.58 (s, 2 H), 2.64-2.69 (m, 2 H), 2.92 (s, 3 H), 3.62-3.66 (m, 2 H), 3.75 (s, 2 H), 4.43-4.46 (m, 1 H), 4.50 and 4.56 (2 s, 2 H), 6.51-6.60 (m, 2 H), 6.73-7.21 (m, 8 H) ppm. MS (electrospray) m/z 568 [M + H]$^+$ |

| | | |
|---|---|---|
| 14 | 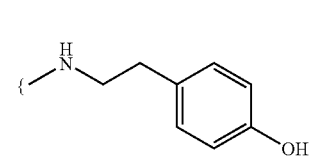 | ¹HNMR (400 MHz, DMSO$_{d6}$) δ: 0.90 (s, 3 H), 0.96 (s, 3 H), 1.30-1.50 (m, 4 H), 2.40 (t, 2 H), 2.46 (s, 2 H), 2.60-2.65 (m, 2 H), 3.89 (s, 3 H), 2.95-3.08 (m, 2 H), 3.25-3.30 (m, 2 H), 4.40-4.44 (m, 1 H), 6.62 (d, 2 H), 6.81 (d, 2 H), 6.91 (d, 2 H), 6.90-7.06 (m, 4 H), 7.15 (t, 1 H), 7.18 (s, 1 H), 7.94 (t, 1 H). MS (electrospray) m/z 582 [M − H]⁻, 584 [M + H]⁺ |
| 15 | 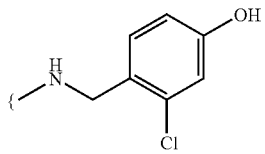 | ¹HNMR (400 MHz, DMSO$_{d6}$) δ: 0.90 (s, 3 H), 0.96 (s, 3 H), 2.48-2.64 (m, 4 H), 2.87 (s, 3 H), 3.17 (q, 2 H), 3.30 (s, 2 H), 4.40-4.43 (m, 1 H), 6.61 (d, 2 H), 6.80 (d, 1 H), 6.85 (d, 2 H), 6.90-7.05 (m, 4 H), 7.16 (t, 1 H), 7.18 (s, 1 H), 7.98 (t, 1 H). MS (electrospray) m/z 554 [M − H]⁻ |
| 16 | 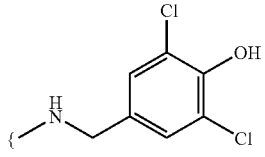 | ¹HNMR (400 MHZ, CD$_3$OD) δ: 1.06 (s, 3 H), 1.08 (s, 3 H), 2.68-2.92 (m, 7 H), 3.51 (s, 2 H), 4.34 (s, 2 H), 4.64-4.66 (m, 1 H), 6.63 (d, 1 H), 6.78-6.79 (m, 1 H), 6.86 (d, 1 H), 7.03-7.22 (m, 6 H), 7.36-7.37 (m, 1 H). MS (electrospray) m/z 574 [M − H]⁻, 576 [M + H]⁺, 598 [M + Na]⁺ |
| 17 | 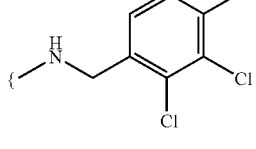 | ¹HNMR (400 MHz, CD$_3$OD) δ: 1.12 (s, 3 H), 1.13 (s, 3 H), 2.79 (s, 2 H), 2.92 (s, 3 H), 3.00 (d, 2 H), 3.51 (s, 2 H), 4.18 (s, 2 H), 4.77-4.80 (m, 1 H), 6.89 (d, 1 H), 6.97 (s, 1 H), 7.05-7.18 (m, 5 H), 7.22-7.26 (m, 1 H), 7.40 (s, 1 H). MS (electrospray) m/z 610/612 [M + H]⁺, 608/610 [M − H]⁻ |
| 18 | 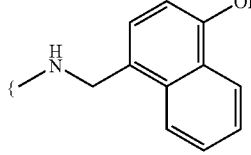 | ¹HNMR (400 MHz, CD$_3$OD) δ: 1.12 (s, 3 H), 1.13 (s, 3 H), 2.77-2.81 (m, 2 H), 2.90 (s, 3 H), 2.91-2.97 (m, 2 H), 3.53 (s, 2 H), 4.36 (s, 2 H), 4.69-4.72 (m, 1 H), 6.74 (d, 1 H), 6.88 (d, 1 H), 7.01-7.06 (m, 2 H), 7.10-7.12 (m, 2 H), 7.16-7.25 (m, 2 H), 7.38-7.39 (m, 1 H) MS (electrospray) m/z 610/612 [M + H]⁺, 632/634 [M + Na]⁺, 608/610 [M − H]⁻ |
| 19 | 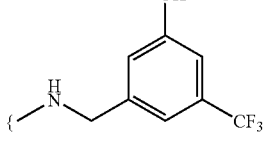 | ¹HNMR (400 MHz, DMSO$_{d6}$) δ: 1.12 (s, 6 H), 2.91-2.98 (m, 7 H), 3.43 (s, 2 H), 4.56 (s, 2 H), 4.75-4.78 (m, 1 H), 6.76 (d, 1 H), 6.91 (d, 1 H), 7.04 (d, 1 H), 7.09-7.24 (m, 5 H), 7.30 (s, 1 H), 7.39-7.45 (m, 2 H), 7.85-7.87 (m, 1 H), 8.13-8.15 (m, 1 H) ppm. MS (electrospray) m/z 592 [M + H]⁺, 614 [M + Na]⁺, 590 [M − H]⁻ |
| 20 | 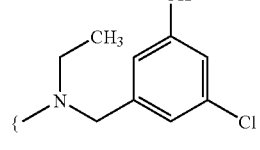 | ¹HNMR (400 MHz, DMSO$_{d6}$) δ: 0.93 (s, 3 H), 0.95 (s, 3 H), 2.58 (s, 2 H), 2.65-2.66 (m, 2 H), 2.91 (s, 3 H), 3.46 (s, 2 H), 4.26-4.27 (m, 2 H), 4.42-4.46 (m, 1 H), 6.82 (d, 1 H), 6.89-6.93 (m, 2 H), 6.96-7.01 (m, 3 H), 7.05 (s, 1 H), 7.06-7.10 (m, 1 H), 7.15-7.19 (m, 2 H) ppm. MS (electrospray) m/z 610 [M + H]⁺, 632 [M + Na]⁺, 608 [M − H]⁻ |
| 21 | 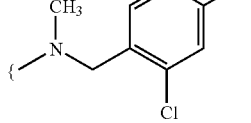 | ¹HNMR (400 MHz, DMSO$_{d6}$) δ: 0.88–0.91 (m, 6 H), 0.95-0.98 (m, 3 H), 2.50-2.63 (m, 4 H), 2.86 (s, 3 H), 3.23-3.28 (m, 2 H), 3.58 and 3.72 (2 s, 2 H), 4.39 and 4.47 (2 s, 3 H), 6.54 (s, 1 H), 6.61-6.67 (m, 2 H), 6.78 (d, 1 H), 6.92-7.02 (m, 3 H), 7.08 (2, 1 H), 7.13-7.15 (m, 2 H) ppm. MS (electrospray) m/z 604 [M + H]⁺, 626 [M + Na]⁺ |
| 22 | | ¹H NMR (400 MHz, CD$_3$OD): rotamers δ 1.16-1.25 (m, 6 H), 2.85-3.10 (m, 10 H), 3.79 and 3.84 (2 s, 2 H), 4.62 and 4.63 (2 s, 2 H), 4.78-4.82 (m, 1 H), 6.65-6.70 (m, 2 H), 6.80-6.84 (m, 2 H), 6.88 (d, 1 H), 7.01 (d, 1 H), 7.08-7.31 (m, 4 H). LRMS (electrospray): m/z [M + H]⁺ 590, [M + Na]⁺ 612. |

| | | |
|---|---|---|
| 23 | 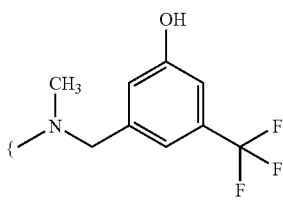 | $^1$H NMR (400 MHz, DMSO$_{d6}$) δ: (rotamers) 0.86-0.90 (m, 6 H), 2.51 and 2.55 (2 s, 2 H), 2.58-2.65 (m, 2 H), 2.87 (s, 3 H), 2.77 and 2.90 (2 s, 3 H), 3.66 and 3.73 (2 s, 2 H), 4.38-4.42 (m, 1 H), 4.48 and 4.61 (2 s, 2 H), 6.77-6.80 (m, 2 H), 6.89-6.91 (m, 2 H), 6.93-6.99 (m, 3 H), 7.03-7.06 (m, 1 H), 7.13-7.18 (m, 2 H) ppm.<br>LRMS (electrospray) : m/z 624 [M + H]$^+$. |
| 24 | 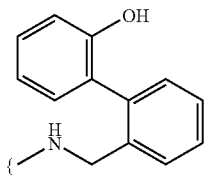 | $^1$H NMR (400 MHz, CD$_3$OD): δ = 1.32 (s, 6 H), 2.97 (s, 3 H), 2.99 (s, 2 H), 3.11-3.23 (m, 2 H), 3.54 (s, 2 H), 4.29-4.31 (m, 2 H), 4.82-4.86 (m, 1 H), 6.89-6.92 (m, 2 H), 6.95 (d, 1 H), 7.08 (dd, 1 H), 7.17-7.24 (m, 6 H), 7.29-7.35 (m, 4 H), 7.46 (d, 1 H) ppm.<br>LRMS (electrospray): m/z [M + H]$^+$ 618, [M + Na]$^+$ 640, [M − H]$^−$ 616. |
| 25 | 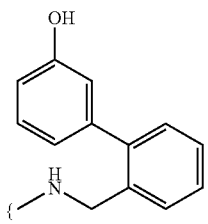 | $^1$H NMR (400 MHz, CD$_3$OD): δ = 1.33 (s, 3 H), 1.34 (s, 3 H), 2.98 (s, 3 H), 3.01 (m, 2 H), 3.21-3.25 (m, 2 H), 3.56 (s, 2 H), 4.35 (s, 2 H), 4.83-4.86 (dd, 1 H), 6.75-6.81 (m, 3 H), 6.95 (d, 1 H), 7.18-7.25 (m, 6 H), 7.28-7.36 (m, 4 H), 7.45 (d, 1 H) ppm.<br>LRMS (Electrospray): m/z [M + H]$^+$ 618, [M + Na]$^+$ 640. |
| 26 | 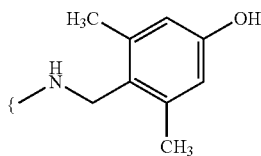 | $^1$H NMR (400 MHz, DMSO$_{d6}$) δ: 0.91 (s, 3 H), 0.93 (s, 3 H), 2.08 (s, 6 H), 2.57 (s, 2 H), 2.65-2.66 (m, 2 H), 2.89 (s, 3 H), 3.38 (s, 2 H), 4.06-4.07 (m, 2 H), 4.33-4.46 (m, 1 H), 6.71 (s, 2 H), 6.81 (d, 1 H), 6.97 (d, 1 H), 7.01 (d, 1 H), 7.05-7.09 (m, 2 H), 7.13-7.19 (m, 2 H), 8.28-8.31 (m, 1 H) ppm.<br>LRMS (APCl): m/z 570 [M + H]$^+$ |
| 27 | 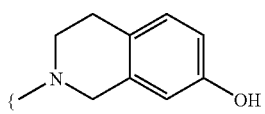 | $^1$HNMR (400 MHz, DMSO$_{d6}$) δ: 0.90 (m, 6 H), 2.41-2.72 (m, 6 H), 2.91 (s, 3 H), 3.60 (m, 2 H), 3.75 (s, 2 H), 4.40-4.60 (m, 3 H), 6.41-6.59 (m, 2 H), 6.81-7.18 (m, 8 H) ppm.<br>MS (electrospray) m/z 590 [M + Na]$^+$, 566 [M − Na]$^−$ |
| 28 | 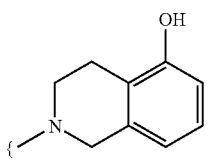 | $^1$HNMR (400 MHz, DMSO$_{d6}$) δ: 0.9 (m, 6 H), 2.41 -2.46 (2 H, m), 2.54-2.58 (2 H, m), 2.60-2.67 (2 H, m), 2.85 (s, 3 H). 3.61 (m, 2 H), 3.70 (m, 2 H), 4.38-4.41 (m, 1 H), 4.61 (m, 2 H), 6.50-6.61 (m, 2 H), 6.81 (d, 1 H), 6.91-7.23 (m, 7 H) ppm.<br>MS (electrospray) m/z 568 [M + H]$^+$, 590 [M + Na]$^+$ |
| 29 | 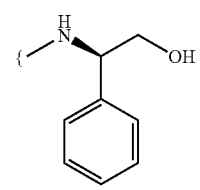 | $^1$HNMR (400 MHz, DMSO$_{d6}$) δ: 0.81 (s, 3 H), 0.85 (s, 3 H), 2.58 (m, 2 H), 2.62 (m, 2 H), 2.89 (s, 3 H), 3.41 (d, 1 H), 3.45 (d, 1 H), 3.58 (d, 2 H), 4.40 (m, 1 H), 4.80 (m, 1 H), 6.80-7.20 (m, 11 H), 8.40 (d, 1 H) ppm.<br>MS (APCl) m/z 578 [M + Na]$^+$ |
| 30 | 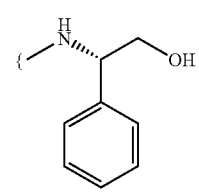 | $^1$HNMR (400 MHz, DMSO$_{d6}$) δ: 0.81 (s, 3 H), 0.84 (s, 3 H), 2.50 (m, 2 H), 2.63 (m, 2 H), 2.85 (s, 3 H), 3.40 (m, 2 H), 3.57 (m, 2 H), 4.40 (m, 1 H), 4.80 (m, 1 H), 6.80 (d, 1 H), 6.98 (m, 1 H), 7.00 (m, 9 H), 8.40 (d, 1 H) ppm.<br>MS (APCl) m/z 554 [M − H]$^−$ |

-continued

| | | |
|---|---|---|
| 31 | 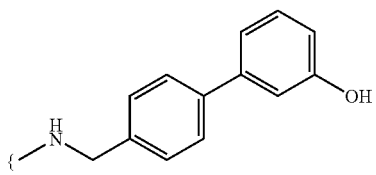 | $^1$H NMR (400 MHz, CD$_3$OD): δ 1.25 (s, 3 H), 1.26 (s, 3 H), 2.93 (s, 2 H), 2.96 (s, 3 H), 3.07-3.09 (m, 2 H), 3.62 (s, 2 H), 4.44 (s, 2 H), 4.77-4.80 (m, 1 H), 6.77-6.79 (m, 1 H), 6.93 (d, 1 H), 7.01-7.02 (m, 1 H), 7.05-7.07 (m, 1 H), 7.14-7.18 (m, 2 H), 7.20-7.27 (m, 3 H), 7.29-7.34 (m, 3 H), 7.43 (d, 1 H), 7.51 (s, 1 H), 7.54 (s, 1 H) ppm. LRMS (Electrospray): m/z [M + H]$^+$ 618, [M + Na]$^+$ 640. |
| 32 | 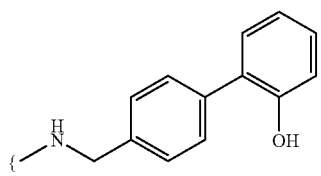 | $^1$H NMR (400 MHz, CD$_3$OD): δ 1.14 (s, 3 h), 1.16 (s, 3 H), 2.77-3.00 (m, 7 H), 3.60 (s, 2 H), 4.44 (s, 2 H), 4.69-4.72 (dd, 1 H), 6.89-6.93 (m, 3 H), 7.09-7.30 (m, 9 H), 7.43 (d, 1 H), 7.50 (s, 1 H), 7.52 (s, 1 H) ppm. LRMS (Electrospray): m/z [M − H]$^-$ 616 |

Examples 34-38

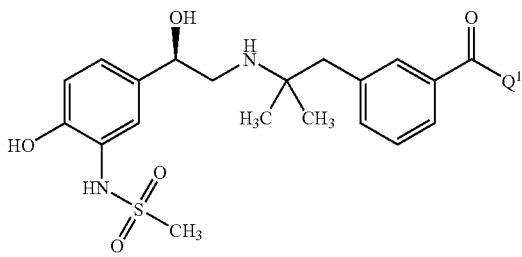

| | | |
|---|---|---|
| 33 | 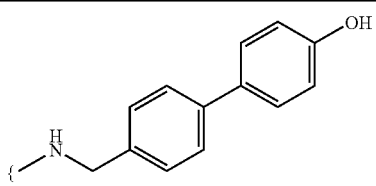 | $^1$HNMR (400 MHz, DMSO$_{d6}$) δ: 0.95 (s, 3 H), 0.98 (s, 3 H), 2.65-2.71 (m, 4 H), 2.93 (s, 3 H), 4.46-4.52 (m, 3 H), 6.83-6.86 (m, 3 H), 7.03-7.06 (m, 1 H), 7.22-7.23 (m, 1 H), 7.30-7.38 (m, 4 H), 7.47 (d, 2 H), 7.54 (d, 2 H), 7.73-7.76 (m, 2 H), 8.96-8.99 (m, 1 H) ppm. MS (electrospray) m/z 604 [M + H]$^+$ |
| 34 | 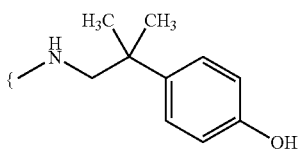 | $^1$HNMR (400 MHz, DMSO$_{d6}$) δ: 0.95 (s, 3 H), 0.97 (s, 3 H), 1.26 (s, 6 H), 2.63-2.70 (m, 4 H), 2.93 (s, 3 H), 3.39-3.40 (m, 2 H), 4.44-4.48 (m, 1 H), 6.71 (d, 2 H), 6.84 (d, 1 H), 7.05 (d, 1 H), 7.20-7.34 (m, 4 H), 7.58-7.60 (m, 2 H), 8.02-8.06 (m, 1 H) ppm. MS (electrospray) m/z 570 [M + H]$^+$ |
| 35 | 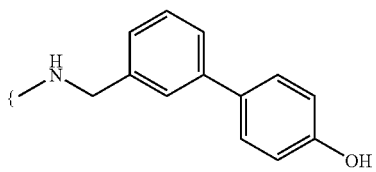 | $^1$HNMR (400 MHz, DMSO$_{d6}$) δ: 0.95 (s, 3 H), 0.98 (s, 3 H), 2.64-2.71 (m, 4 H), 2.93 (s, 3 H), 4.45-4.48 (m, 1 H), 4.54-4.56 (m, 2 H), 6.82-6.86 (m, 3 H), 7.04 (d, 1 H), 7.22-7.40 (m, 5 H), 7.45-7.48 (m, 3 H), 7.54 (s, 1 H), 7.73-7.75 (m, 2 H), 8.98-9.01 (m, 1 H) ppm. MS (electrospray) m/z 604 [M + H]$^+$ |
| 36 | 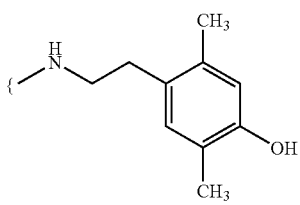 | $^1$HNMR (400 MHz, CD$_3$OD) δ: 1.05 (s, 3 H), 1.12 (s, 3 H), 2.08 (s, 3 H), 2.22 (s, 3 H), 2.70-2.97 (m, 9 H), 3.46-3.50 (m, 2 H), 4.63-4.66 (m, 1 H), 6.54 (s, 1 H), 6.86 (d, 1 H), 6.88 (s, 1 H), 7.09-7.11 (m, 1 H), 7.30-7.38 (m, 3 H), 7.61 (m, 1 H), 7.66 (d, 1 H) ppm. MS (electrospray) m/z 570 [M + H]$^+$ |
| 37 | 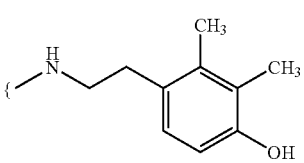 | $^1$HNMR (400 MHz, CD$_3$OD) δ: 1.05 (s, 3 H), 1.12 (s, 3 H), 2.11 (s, 3 H), 2.23 (s, 3 H), 2.70-2.97 (m, 9 H), 3.45-3.49 (m, 2 H), 4.63-4.66 (m, 1 H), 6.54 (d, 1 H), 6.81 (d, 1 H), 6.87 (d, 1 H), 7.09-7.12 (m, 1 H), 7.30-7.38 (m, 3 H), 7.61 (m, 1 H), 7.66 (d, 1 H) ppm. MS (electrospray) m/z 570 [M + H]$^+$, 569 [M − H]$^-$ |

| 38 | 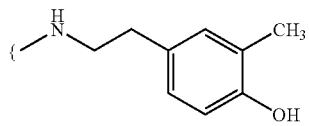 | $^1$HNMR (400 MHz, CD$_3$OD) δ: 1.04 (s, 3 H), 1.11 (s, 3 H), 2.12 (s, 3 H), 2.70-2.96 (m, 9 H), 3.51-3.54 (m, 2 H), 4.63-4.66 (m, 1 H), 6.64 (d, 1 H), 6.86 (d, 2 H), 6.94 (m, 1 H), 7.09 (d, 1 H), 7.30-7.38 (m, 3 H), 7.59 (m, 1 H), 7.64 (d, 1 H) ppm. MS (electrospray) m/z 556 [M + H]$^+$ |
|---|---|---|

Unless otherwise stated all reactions were carried out under a nitrogen atmosphere.
Abbreviations
TBDMS = tert-butyl(dimethyl)silyl
IPA: isopropyl alcohol
THF: Tetrahydrofuran
s = singlet
d = doublet
dd = double doublet
t = triplet
q = quartet
m = multiplet
bs = broad singlet e.g. NH, or OH The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-Pig Trachea

Male, Dunkin-Hartley guinea pigs (475-525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3-4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma I7378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30-45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma I5627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The EC$_{50}$ value for beta-2 agonist according to the present invention refers to the concentration of compound required to produce half maximal effect. Data for beta-2 agonists according to the present invention are then expressed as relative potency to isoprenaline defined by the ratio (EC$_{50}$ beta-2 agonist)/(EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β$_2$ antagonist) which results in the case of a beta-2 mediated effect in a rightward-shift of the test compound dose response curve.

According to another alternative, the agonist potency for the β2 receptor of the compounds of the formula (1) may also be determined by the measure of the concentration of compound according to the present invention required to produce half maximal effect (EC$_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, 1-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46-50, 1987 and Bouvier et al., Mol Pharmacol 33: 133-139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040-174) and resuspended in stimulation buffer (NEN, SMP004B) to give $1 \times 10^6$ cells/ml CHOhB2. Compounds were incubated with 50 µl/well cells for 1 hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit. It has thus been found that the compounds of formula (1) according to the present invention that are illustrated in examples 1 to 38 above show a β2 CAMP $EC_{50}$ between 0.02 nM and 3.03 nM. The following table illustrate the activity of the compounds of the invention:

| Example | $EC_{50}$ (nM) |
| --- | --- |
| 1 | 0.03 |
| 2 | 0.24 |
| 3 | 0.02 |
| 6 | 0.16 |
| 7 | 0.26 |
| 9 | 0.45 |
| 13 | 0.08 |
| 15 | 0.09 |
| 20 | 0.29 |

The invention claimed is:

1. A method of treating a disease in a mammal, said method comprising administering to said mammal an effective amount of a compound of the formula (I):

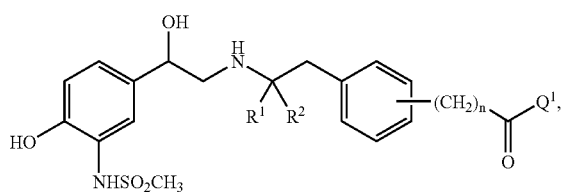

(1)

or a pharmaceutically acceptable salt, isomer or tautomer thereof, wherein:

the $(CH_2)_n$—C(=O)$Q^1$ group is in the meta or para position;

$R^1$ and $R^2$ are independently selected from H and $C_1$-$C_4$ alkyl;

n is 0, 1 or 2; and $Q^1$ is selected from:

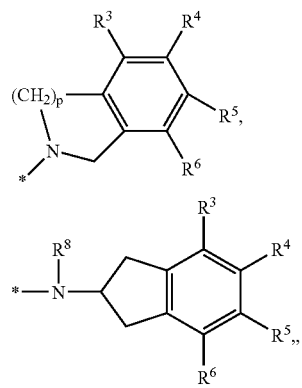

and *—$NR^8$-$Q^2$-A;

p is 1 or 2;

$Q^2$ is $C_1$-$C_4$ alkylenyl optionally substituted with one hydroxy group;

$R^8$ is H or $C_1$-$C_4$alkyl;

A is pyridyl optionally substituted with OH, $C_3$-$C_7$ cycloalkyl optionally substituted with OH, or

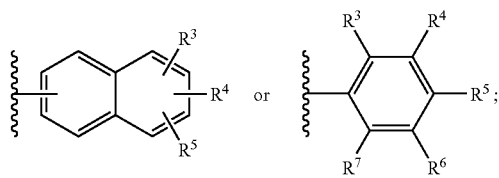

$R^3$, $R^4$, $R^5$, $R^6$ and $R^7$ are independently H, $C_1$-$C_4$ alkyl, $OR^9$, $SR^9$, halo, CN, $CF_3$, $OCF_3$, $COOR^9$, $SO_2NR^9R^{10}$, $CONR^9R^{10}$, $NR^9R^{10}$, $NHCOR^{10}$ or phenyl optionally substituted with 1 to 3 $OR^9$, halo or $C_1$-$C_4$ alkyl;

$R^9$ and $R^{10}$ are independently H or $C_1$-$C_4$ alkyl; and the * represents the attachment point to the carbonyl group of formula (1);

provided that the group $Q^1$ is substituted with at least one hydroxy group, or a pharmaceutical composition comprising said compound of formula (1), an isomer or tautomer thereof, or a pharmaceutically acceptable salt of said compound, isomer or tautomer, and a pharmaceutically acceptable excipient or additive, wherein said disease is selected from the group consisting of: asthma, acute bronchoconstriction, small airways obstruction and chronic obstructive pulmonary disease.

2. A method of claim 1 wherein said asthma is selected from the group consisting of: atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

* * * * *